(12) United States Patent
Cameron et al.

(10) Patent No.: US 7,758,868 B2
(45) Date of Patent: Jul. 20, 2010

(54) MODIFIED POLYMERASES AND ATTENUATED VIRUSES AND METHODS OF USE THEREOF

(75) Inventors: Craig E. Cameron, State College, PA (US); Christian Castro, State College, PA (US); Jamie J. Arnold, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 11/963,930

(22) Filed: Dec. 24, 2007

(65) Prior Publication Data

US 2008/0175861 A1 Jul. 24, 2008

Related U.S. Application Data

(60) Provisional application No. 60/871,570, filed on Dec. 22, 2006, provisional application No. 60/892,086, filed on Feb. 28, 2007.

(51) Int. Cl.
*A61K 39/13* (2006.01)
*C12N 7/00* (2006.01)
*C12N 7/04* (2006.01)
(52) U.S. Cl. .................. 424/217.1; 435/235.1; 435/236
(58) Field of Classification Search ........................ None
See application file for complete search history.

(56) References Cited

U.S. PATENT DOCUMENTS 6,541,003 B1 4/2003 Smith

FOREIGN PATENT DOCUMENTS

WO WO 98/13501 4/1998

OTHER PUBLICATIONS

Centers for Disease Control, 2008, Parents' Guide to Childhood Immunization.*
Castro and Cameron, The FASEB Journal, Mar. 2006, 20(4):A512.*
Arnold, Jamie J., et al., Remote Site Control of an Active Site Fidelity Checkpoint in a Viral RNA-dependent RNA Polymerase, Journal of Biological Chemistry, vol. 280, No. 27, Issue Jul. 8, 2005, pp. 25706-25716.
Castro, Christian, et al., Two Proton Transfers in the Transition State for Nucleotidyl Transfer Catalyzed by RNA- and DNA-dependent RNA and DNA Polymerases, PNAS, Mar. 13, 2007, vol. 104 No. 11, pp. 4267-4272.
Arnold, Jamie J., et al., Poliovirus RNA-Dependent RNA Polymerase (3Dpol): Pre-Steady-State Kinetic Analysis of Ribonucleotide Incorporation in the Presence of Mn2+Δ, Biochemistry, May 11, 2004, 43(18), pp. 5138-5148.
Arnold, Jamie J., et al., Poliovirus RNA-Dependent RNA Polymerase (3Dpol): Pre-Steady-State Kinetic Analysis of Ribonucleotide Incorporation in the Presence of Mg2+†, Biochemistry, May 11, 2004; 43 (18); pp. 5126-5137.
Arnold, Jamie J., et al., Poliovirus RNA-dependent RNA Polymerase (3Dpol) Assembly of Stable, Elongation-Competent Complexes by Using a Symmetrical Primer-Template Substrate (sym/sub), Journal of Biological Chemistry, Feb. 25, 2000; pp. 5329-5336.
Shah, et al., "Differential Influence of Nucleoside Analog-Resistance Mutations K65R . . . ," The Journal of Biological Chemistry, May 31, 2000, 275(35); pp. 27037-27044.
Sousa, "Structural and Mechanistic Relationships Between Nucleic Acid Polymerases," Elsevier Science Ltd 21, May 1996, SO968-0004(96) 10023-2, p. 186-187.
Hansen, et al., "Structure of the RNA-Dependent RNA Polymerase of Poliovirus," Current Biology Ltd, Aug. 15, 1997, 5;1109-1122, p. 1109.
Poyry, et al., "Genetic and Phylogenetic Clustering of Enteroviruses," Journal of General Virology, 1996, 77: 1699-1717, Table 1.
Asano, et al., "Identification of Two Nucleotide-Binding Domains on the PB1 Subunit of Influenza Virus RNA Polymerase," Journal of Biochemistry, Apr. 30, 1997, 122: p. 627.
Ghedin, et al., Large-Scale Sequencing of Human Influenza Reveals the Dynamic Nature of Viral Genome Evolution, Nature, Oct. 20, 2005, 437(7062), p. 1163.
Huang, et al., "Structure of a Covalently Trapped Catalytic Complex of HIV-1 Reverse Transcriptase: Implications for Drug Resistance," Science, Nov. 27, 1998, 282(5394).
http://www.ncbi.nlm.nih.gov/entrez/viewer.fcgi?db=protein&id=4139739, (2008) 2 pages.
http://www.ncbi.nlm.nih.gov/entrez/viewer.fcgi?db=protein&id=66353884, (2008) 4 pages.

\* cited by examiner

*Primary Examiner*—Stacy B Chen
(74) *Attorney, Agent, or Firm*—Novak Druce + Quigg

(57) ABSTRACT

The invention encompasses compositions and methods relating to viral polymerases having one or more substitutions of different amino acids at conserved regions of the polymerase yields enzymes with varying rates and fidelity of replication. A universally applicable, polymerase-mechanism-based strategy for production of attenuated viruses and anti-viral vaccines is disclosed.

11 Claims, 20 Drawing Sheets

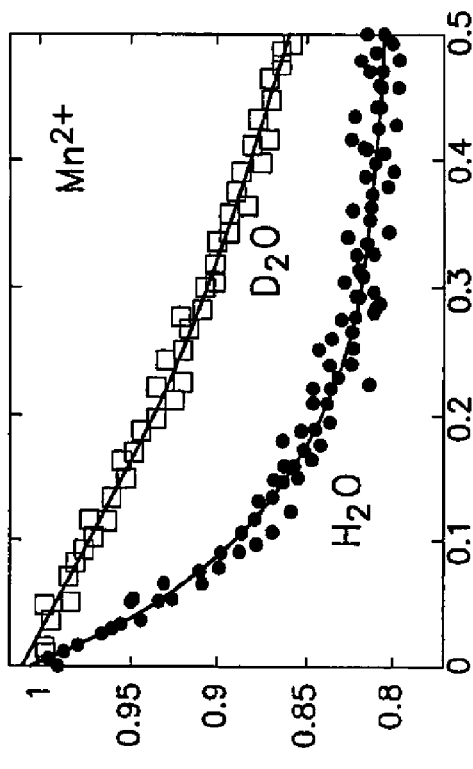
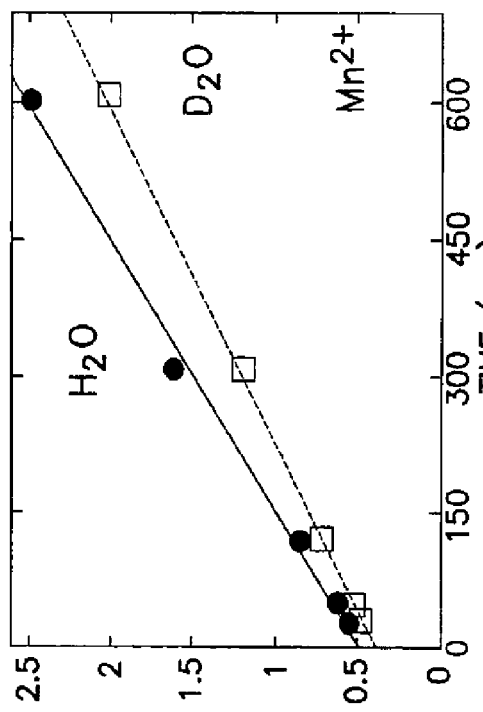
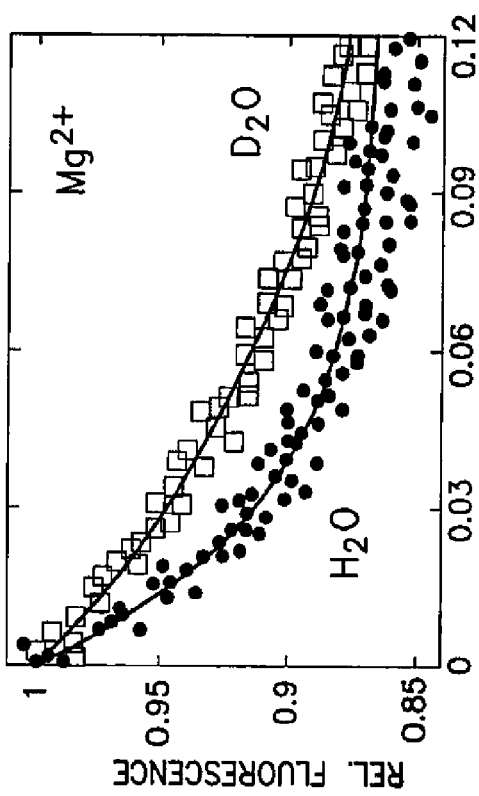
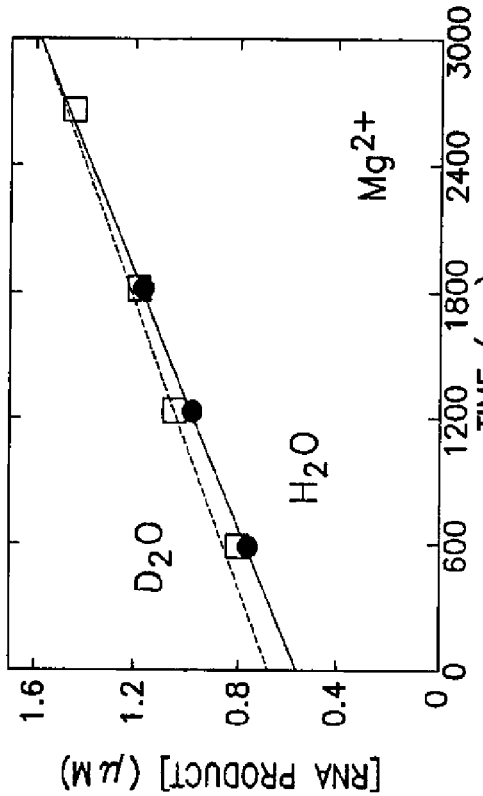

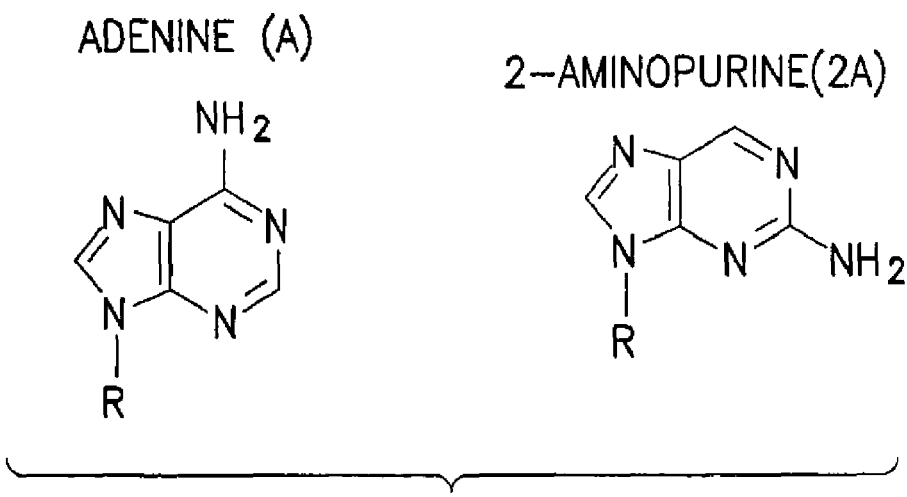
FIG.7A
```
G C U A G G G C C C
        C C C G G G A U C G
        TEMPLATING       ↑ ↑ ↑
        POSITION         0 +1 +2
```
FIG.7B
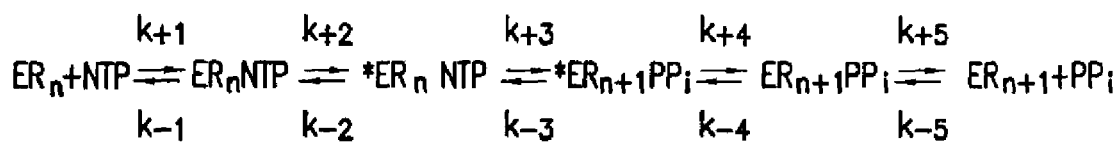
FIG.9

FIG.10C

Lys481
Ile484
Glu491
Asn464

FIG.10B

Lys359
Thr362
Glu369
Ser341

FIG.10A

| Inf-A-PB1 | 464 | NRFYRTC<u>K</u>IL<u>L</u>G<u>I</u>N<u>M</u>S-K<u>K</u>K<u>S</u>YINRTGTF<u>E</u> | 491 |
| Inf-B-PB1 | 463 | NDFYRTC<u>K</u>IL<u>L</u>G<u>I</u>N<u>M</u>S-K<u>K</u>K<u>S</u>YCNETGMF<u>E</u> | 490 |
| Inf-C-PB1 | 465 | RRFNAVC<u>K</u>LI<u>G</u>I<u>N</u>M<u>S</u>-LE<u>K</u>S<u>Y</u>GSLPELF<u>E</u> | 492 |
| PV1=3D | 341 | SLLAQSG<u>K</u>DYG<u>L</u>T<u>M</u>TPAD<u>K</u>S<u>A</u>TFETVTW<u>E</u> | 369 |

FIG.10D

MOTIF D

|  |  | HELIX | LOOP |  |
|---|---|---|---|---|
| PV | 338 | VDAS-----LLAQSG---KDYG | LTMTPAD--[K]SA-TFE | 364 |
| Cox | 338 | VDAS-----LLAQSG---KDYG | LTMTPAD--[K]SA-TFE | 364 |
| HRV14 | 337 | LDPQ-----VLATLG---KNYG | LTITPPD--[K]SE-TFT | 363 |
| RHDV | 364 | MVSL-----LPAIIENLRDYG | LSPTAAD---[K]TE-FID | 392 |
| FCV | 254 | FASV-----SDQIFANLSAYG | LKPTRVD--[K]SVGSIE | 283 |
| SARS | 770 | YAAQGLVASIKNFKAVLYYQ | NNVFMSEA-[K]CWIETD | 804 |
| MHV | 766 | FASKGYIANISAFQQVLYYQ | NNVFMSEA-[K]CWVETD | 800 |
| HCV | 328 | GTQEDEASLRAFTEAMTRYS | --APPGDPP[K]PEYDLE | 361 |
| HIVRT | 195 | IGQHR-TKIEELRQHLLRWG | LT-TP-D-K[K]HQK---- | 223 |
| QBeta | 369 | ----------PALREVFKY- | -VGFTTNTK[K]TFSE-- | 390 |

FIG.11A

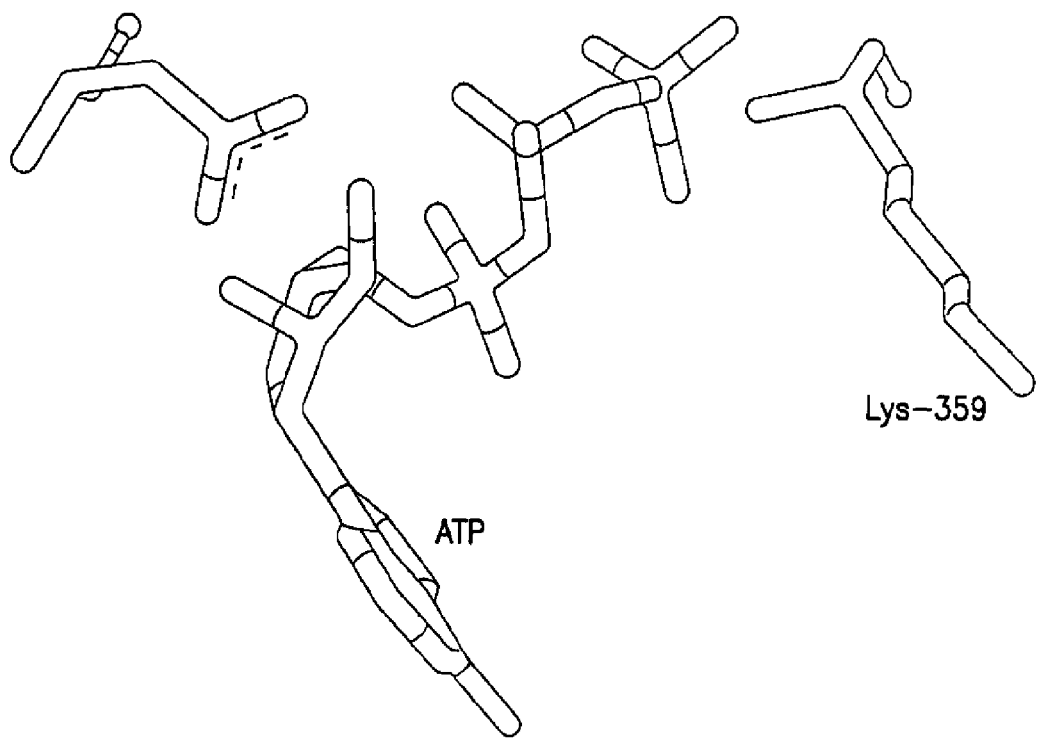

FIG.11B

HIV-1 RT RdDp

T7 DdRp

RB69 DdDp

MODIFIED POLYMERASES AND ATTENUATED VIRUSES AND METHODS OF USE THEREOF

CROSS REFERENCE TO RELATED APPLICATION

The present application claims the priority of U.S. provisional patent application No. 60/871,570 filed Dec. 22, 2006, and U.S. provisional patent application No. 60/892,086 filed Feb. 28, 2007.

STATEMENT AS TO FEDERALLY SPONSORED RESEARCH

This invention was made with government support under grant number AI45818, awarded by the National Institutes of Health. The government has certain rights in the invention.

FIELD OF THE INVENTION

The invention relates generally to the fields of molecular biology, virology and immunology. More particularly, the invention relates to viral attenuation and anti-viral vaccines.

BACKGROUND

Many successful viral vaccines use live attenuated virus strains. The rate-limiting step for live-virus vaccine development is the identification of a suitable attenuated virus. Conventional methods of developing an attenuated virus involve propagation of the virus under novel conditions, such as passage of the virus in "foreign" or non-permissive cell lines, so that it becomes less pathogenic to its original host as it evolves under the new conditions. Although this methodology has shown remarkable success, little is known about the process by which the attenuating mutations arise and evolve, and isolating an attenuated virus is a random, slow process. In addition, the outcome of an attempted attenuation is largely unpredictable, and depending on the nature of the attenuation, an attenuated virus may revert to virulence.

Some currently used attenuation methods result in virus vaccine strains that are too virulent to produce. Highly virulent strains are deleterious to the host and developing vaccines requires inactivation of the virus. This has certain drawbacks. For example, inactivated viruses as orally or nasally applied vaccines must be given in high concentrations in order to bring about a significant increase of antibodies. As another example, the administration of inactivated influenza virus or antigen in convenient commercial doses, free of side effects, with nasal or oral administration, does not produce a satisfactory immune response without the use of an adjuvant. (Chen et al., 1989, *Current Topics in Microbiology and Immunology* 146:101 106, Couch et al., 1997, *J. Infect. Dis.* 176:38 44). Thus, for example, for the optimum induction of the immune response with oral administration of an emulsion-inactivated vaccine, an antigen content between 66 µg antigen/dose and 384 µg antigen/dose is required (Avtushenko et al., 1996, *J. Biotechnol.* 44:21 28). Thus, this dose lies far above that of an inactivated vaccine for parenteral administration, which is at approximately 15 µg antigen/dose.

A cold-adapted, live attenuated influenza virus vaccine to be found in clinical studies for nasal administration is based on virus antigens from which reassortments must be produced annually by means of genetic methods, in which the genes for the hemagglutinin and neuramidase antigens of the corresponding influenza A or B strain are transferred to an attenuated, cold-adapted master virus strain. This method is very time consuming and labor intensive. In addition, there is the danger that through reversion the attenuated virus back mutates into a virulent virus and thus can trigger viremia. When immunization is carried out with living viruses there is also a further spread in the body of the immunized individual. When cold-adapted viruses are used, there is also the constant necessity of storing the virus vaccine below the freezing point, as close to $-20°$ C. as possible, which then requires the absolute maintenance of a chain of refrigeration to ensure sufficient storage life of the vaccine.

Eggs are used for the production of the live attenuated influenza virus vaccine virus reassortments and the propagation of the vaccine viruses, which entails the risk that any contaminating infectious agents that may be present may be transferred into the eggs. The purification of live viruses is also not without problems because they represent infectious material and thus a higher standard of security must be maintained.

The availability of a technique for attenuating viruses in a rapid and non-random way would eliminate the disadvantages associated with current methods.

SUMMARY

The invention relates to the development of modified viral polymerases that have an active site lysine residue substitution resulting in an altered rate of replication and altered fidelity compared to wild-type (WT) polymerases. In a typical embodiment, when incorporated into a virus, a modified polymerase as described herein exhibits a decreased rate of replication and a higher fidelity than a corresponding WT polymerase. In the experiments described herein, a poliovirus (PV) 3Dpol active site residue, Lys-359, was identified as a general acid catalyst during the phosphoryl transfer step of the nucleotide incorporation reaction. Surprisingly, subtle changes in polymerase speed and accuracy were found to have dramatic attenuation effects on the virus. Mutant PV viruses were made having a modified polymerase gene resulting in either a K359R or K359H substitution. These viruses were shown to be infectious and attenuated in cells relative to WT virus. The well-conserved residues in a polymerase active site as described herein modulate polymerase speed and/or accuracy, and are therefore targets for attenuating viruses. Active site lysine residues in polymerases from other classes were also identified and analyzed. Thus, the compositions and methods described herein can be applied to any virus, including viruses with regular intervals of antigenic shift (e.g., influenza), newly emerging and re-emerging viruses (e.g., SARS, West Nile, Dengue), and viruses used as agents of terror or biological weapons (e.g., Ebola, smallpox). Thus, the compositions and methods described herein provide a universal strategy for attenuating viruses for anti-viral vaccines. The present invention also solves the problem of generating vaccines of both highly virulent viruses and in amounts that induce either the humoral or cellular or both, immune responses.

Accordingly, the invention includes an attenuated virus including a polymerase gene that encodes a polymerase having a modification that results in a substitution of a lysine residue to a leucine, histidine, or arginine residue, the lysine residue capable of functioning as a general acid catalyst during a phosphoryl transfer step of a nucleotide incorporation reaction and located on helix O of A-family polymerases, helix P of B-family polymerases and on the loop of structural motif D of RNA-dependent RNA polymerases and reverse transcriptases. The substitution causes the polymerase to have increased fidelity compared to a polymerase encoded by a WT polymerase gene not having the modification. The polymerase can be, for example, a PV polymerase and the lysine residue at position 359 of an amino acid sequence encoded by a nucleic acid sequence having accession number V01148 (SEQ ID NO:9); an influenza polymerase and the lysine residue at position 481 of a sequence having accession number AAY44773 (SEQ ID NO:10); or an HIV-1 reverse transcriptase and the lysine residue at position 220 of a sequence having accession number 4139739 (SEQ ID NO:11). The polymerase can be, for example, an A-family polymerase, a B-family polymerase, or a DNA-dependent DNA polymerase. In a typical embodiment, the virus is infectious.

Also within the invention is a vaccine that includes (a) an attenuated virus including a polymerase gene that encodes a polymerase, the polymerase gene having a modification that results in a substitution of a lysine residue to a leucine, histidine, or arginine residue, the lysine residue capable of functioning as a general acid catalyst during a phosphoryl transfer step of a nucleotide incorporation reaction and located on helix O of A-family polymerases, helix P of B-family polymerases and on the loop of structural motif D of RNA-dependent RNA polymerases and reverse transcriptases, and a pharmaceutically acceptable carrier. The substitution causes the polymerase to have increased fidelity compared to a polymerase encoded by a WT polymerase gene not having the modification. The polymerase can be, for example, a PV polymerase and the lysine residue at position 359 of an amino acid sequence encoded by a nucleic acid sequence having accession number V01148; an influenza polymerase and the lysine residue at position 481 of a sequence having accession number AAY44773; or an HIV-1 reverse transcriptase and the lysine residue at position 220 of a sequence having accession number 4139739. The polymerase can be an A-family polymerase, a B-family polymerase, or a DNA-dependent DNA polymerase. The vaccine can further include an adjuvant.

In another embodiment, the invention includes a purified nucleic acid including a polymerase gene that encodes a polymerase, the polymerase gene having a modification that results in a substitution of a lysine residue to a leucine, histidine, or arginine residue, the lysine residue capable of functioning as a general acid catalyst during a phosphoryl transfer step of a nucleotide incorporation reaction and located on helix O of A-family polymerases, helix P of B-family polymerases and on the loop of structural motif D of RNA-dependent RNA polymerases and reverse transcriptases. The substitution causes the polymerase to have increased fidelity compared to a polymerase encoded by a WT polymerase gene not having the modification. The nucleic acid can be within a vector.

In still a further embodiment, the invention includes a method of attenuating a virus including modifying a viral polymerase gene that encodes a polymerase, such that the modification results in a substitution of a lysine residue to a leucine, histidine, or arginine residue, the lysine residue capable of functioning as a general acid catalyst during a phosphoryl transfer step of a nucleotide incorporation reaction and located on helix O of A-family polymerases, helix P of B-family polymerases and on the loop of structural motif D of RNA-dependent RNA polymerases and reverse transcriptases. The substitution causes the polymerase to have increased fidelity compared to a polymerase encoded by a WT polymerase gene not having the modification.

Unless otherwise defined, all technical terms used herein have the same meaning as commonly understood by one of ordinary skill in the art to which this invention belongs.

As used herein, the term "attenuated" means a virus that is modified to be less virulent (disease-causing) than WT virus.

As used herein, "vaccine" includes all prophylactic and therapeutic vaccines. According to one embodiment the vaccine contains an avirulent or attenuated infectious virus, the viral polymerase having amino acid changes in the conserved regions of the polymerase. These changes include for example, substituted amino acids, analogs, deletions and the like.

The vaccine compositions of the invention are suitable for administration to subjects in a biologically compatible form in vivo. The expression "biologically compatible form suitable for administration in vivo" as used herein means a form of the substance to be administered in which any toxic effects are outweighed by the therapeutic effects. The substances may be administered to any animal, preferably humans.

By the terms "RNA-dependent polymerase" and "RDP" is meant a viral polymerase that transcribes either RNA or DNA from an RNA template. RNA viruses described herein produce an RNA-dependent RNA polymerase (RDRP), and retroviruses described herein produce an RNA-dependent DNA polymerase, also referred to as a "reverse transcriptase."

By the term "DNA-dependent DNA polymerase" is meant a viral polymerase that transcribes DNA from a DNA template.

As used herein, a "nucleic acid," "nucleic acid molecule," or "polynucleotide" means a chain of two or more nucleotides such as RNA (ribonucleic acid) and DNA (deoxyribonucleic acid). A "purified" nucleic acid molecule is one that has been substantially separated or isolated away from other nucleic acid sequences in a cell or organism in which the nucleic acid naturally occurs (e.g., 30, 40, 50, 60, 70, 80, 90, 95, 96, 97, 98, 99, 100% free of contaminants). The term includes, e.g., a recombinant nucleic acid molecule incorporated into a vector, a plasmid, a virus, or a genome of a prokaryote or eukaryote.

As used herein, "protein" or "polypeptide" are used synonymously to mean any peptide-linked chain of amino acids, regardless of length or post-translational modification, e.g., glycosylation or phosphorylation.

When referring to a nucleic acid molecule, polypeptide, or virus, the term "native" refers to a naturally-occurring (e.g., a WT) nucleic acid, polypeptide, or virus.

As used herein, the term "vector" refers to a nucleic acid molecule capable of transporting another nucleic acid to which it has been linked. Vectors capable of directing the expression of genes to which they are operatively linked are referred to herein as "expression vectors."

A first sequence is "operably" linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked nucleic acid sequences are contiguous and, where necessary to join two protein coding regions, in reading frame.

Although compositions and methods similar or equivalent to those described herein can be used in the practice or testing of the present invention, suitable compositions and methods are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

FIG. 1 is a pair of schematic illustrations of polymerase-catalyzed phosphoryl transfer.

FIG. 3 is a series of graphs showing solvent deuterium isotope effect on the kinetics of nucleotide incorporation in the pre-steady-state. Pre-steady-state incorporation of AMP into S/S-+1 in $H_2O$ (●) or $D_2O$ (■) in $Mg^{2+}$ (FIG. 3A) or $Mn^{2+}$ (FIG. 3B). The solid line is the fit of the data to equation 1, yielding rate constants, $k_{obs}$, in Mg2+ of 30±4 s−1 and 10±1 s−1 for $H_2O$ and $D_2O$, respectively; and of 10±1 s$^{-1}$ and 1.4±0.3 s$^{-1}$ in $Mn^{2+}$. Steady state incorporation of AMP into S/S-+1 in $H_2O$ (●) or $D_2O$ (■) in $Mg^{2+}$ (FIG. 3C) or $Mn^{2+}$ (FIG. 3D). The lines are the fit of the data to a line, yielding rates in $Mg^{2+}$ of $3.4\times10^{-4}\pm1\times10^{-5}$ μMs$^{-1}$ and $2.9\times10^{-4}\pm3\times10^{-5}$ μMs$^{-1}$ in $H_2O$ and $D_2O$, respectively; and of 0.5±0.1 μMs$^{-1}$ and 0.3±0.1 μMs$^{-1}$ in $Mn^{2+}$.

FIG. 5 is a series of graphs showing that two protons are transferred during phosphodiester bond formation catalyzed by all polymerases.

FIG. 7 illustrates 2-Aminopurine as a fluorescent probe for $3D^{pol}$-catalyzed nucleotide incorporation reactions. FIG. 7A is a schematic illustration showing the 2-Aminopurine (2A) base which is fluorescent and has the capacity to form two basepairs with uracil, however, incorporation of UMP opposite 2A is never as efficient as incorporation opposite A. FIG. 7B shows a primer-template substrate used herein. It is a 10-nt self-complementary RNA, referred to as sym/sub. The templating positions have been designated as indicated: S/S-0, S/S-+1 and S/S-+2. SEQ ID NO:1 in the 5' to 3' direction is hybridized to SEQ ID NO:1 shown in the 3' to 5' direction.

FIG. 8 is a pair of graphs showing that stopped-flow fluorescence assay yields the same kinetic constants as the chemical-quench-flow assay.

FIG. 9 is a schematic representation showing a kinetic mechanism for $3D^{pol}$-catalyzed nucleotide incorporation. The kinetic mechanism for the RNA dependent RNA polymerase (RdRp) from poliovirus ($3D^{pol}$) is shown as one embodiment. One of the advantages of this system is that once $3D^{pol}$ assembles onto the primer-template substrate, this complex has a half-life of greater than two hours, greatly simplifying kinetic analysis. In step one, the enzyme-nucleic acid complex ($ER_n$) binds the nucleoside triphosphate forming a ternary complex ($ER_nN$). Step two involves a conformational change ($*ER_nN$) that orients the triphosphate for catalysis. In step three, phosphoryl transfer occurs ($*ER_{n+1}$ PP$_i$), followed by a second conformational-change step (ER$_{n+1}$PP$_i$) and pyrophosphate release (ER$_{n+1}$).

FIG. 10 is a schematic representation showing the structural motif D of PV polymerase is predicted in Flu polymerases. FIG. 10A shows the palm (catalytic) domain in PV polymerase depicted as cartoon model (pdb: 1RAJ) colored in grey with motif D highlighted in red. FIG. 10B shows motif D in PV polymerase with key residues Lys359 and Thr362 shown. FIG. 10C shows the modeled structure of motif D in influenza polymerase colored in cyan. Residues Lys481 and Ile484 at equivalent positions to Lys359 and Thr362 in B are displayed. FIG. 10D shows the alignment of residues in motif D of PB1 proteins from Influenza A, B and C viruses with poliovirus 3D$^{pol}$. Conserved residues are shown in red. In FIG. 10D, SEQ ID NOs: 16-19 are shown consecutively from the top down.

FIG. 11 illustrates sequence alignments and molecular modeling that reveal that PV 3Dpol RdRp Lys-359 is in position to function as a general acid catalyst. FIG. 11A: Amino acid sequence alignments of a variety of RNA polymerases show absolute conservation of a motif D active site lysine. PV, poliovirus; Cox, coxsackievirus; HRV14, human rhinovirus 14; RHDV, rabbit haemorrhagic disease virus; FCV, feline calicivirus; SARS, severe acute respiratory syndrome coronavirus; MHV, mouse hepatitis virus; HCV, hepatitis C virus; HIVRT, human immunodeficiency virus type-1 reverse transcriptase; QBeta, bacteriophage Q-beta. In FIG. 11A. SEQ ID NOs: 20-29 are shown consecutively from the top down. FIG. 11B: Location of Lys-359, Asp-328 and bound nucleotide (ATP) in model for poliovirus 3Dpol-ternary complex. Lys-359 interacts most closely with the β-phosphate of the nucleotide triphosphate moiety. FIG. 11Ci: Lys-359 is in spatial proximity to the β-phosphate prior to phosphoryl transfer. FIG. 11Cii: As the transition state of phosphoryl transfer is approached, the primer 3'-OH proton, H$_a$, is abstracted by an unidentified base and the ε-amino group of Lys-359 donates its dissociable proton, H$_b$, to the non-bridging oxygen between the α- and β-phosphorus atoms.

FIG. 12 is a series of graphs showing pH rate profiles for PV 3Dpol WT and position 359 mutants support a role as general acid catalyst for Lys-359.

FIG. 14 is a series of graphs showing proton inventories at pD 7.5 for WT K359 3Dpol and for K359L and K359R variants revealing that Lys-359 is the source of one proton transfer during catalysis.

FIG. 15 is a series of crystal structures for HIV-1, T7 and RB69 polymerases. A conserved active site Lys is in position to function as a general acid catalyst during phosphoryl transfer in polymerases from other classes. High-resolution x-ray crystal structures reveal the conserved active site lysine to be.

FIG. 16 is a series of graphs showing proton inventories for WT polymerases and Leu mutants at the conserved active site Lys position, indicating a role as general acid catalyst for this Lys in all classes of nucleic acid polymerases. FIG. 16Aii: Proton inventory for HIV-1 RT K220L RdDp is best fit with straight line model (eq. 6) indicating that replacement of Lys by chemically inert Leu at position 220 results in loss of one rate-enhancing proton transfer during phosphoryl transfer reaction.

DETAILED DESCRIPTION

The invention encompasses compositions and methods relating to the development of modified viral polymerases that have an active site lysine residue substitution resulting in an altered rate of replication and altered fidelity compared to WT polymerases. The compositions and methods described herein provide a universal strategy for attenuating viruses for viral vaccines.

A two-metal ion mechanism has been proposed for polymerase-catalyzed nucleotidyl transfer reactions (Liu, J. & Tsai, M.-D. (2001) *Biochemistry* 40, 9014-9022; Steitz, T. A. (1993) *Current Opinion in Structural Biology* 3, 31-38). In this mechanism (FIG. 1A), metal A increases the nucleophilicity of the primer 3'-OH by lowering its $pK_a$ value, and metal B stabilizes the oxyanion that forms in the transition state and may facilitate pyrophosphate release. During nucleotidyl transfer, the proton from the 3'-OH of the primer ($H_a$ in FIG. 1B) must be removed. Although it is not known whether the pyrophosphate leaving group must be protonated ($H_b$ in FIG. 1B), pyrophosphate protonation should increase the rate of catalysis under physiological conditions given a pKa value in the 9.3 regime. Whether or not active-site residues function as acceptor or donor for these key proton transfer reactions was heretofore not known.

Figure 6:
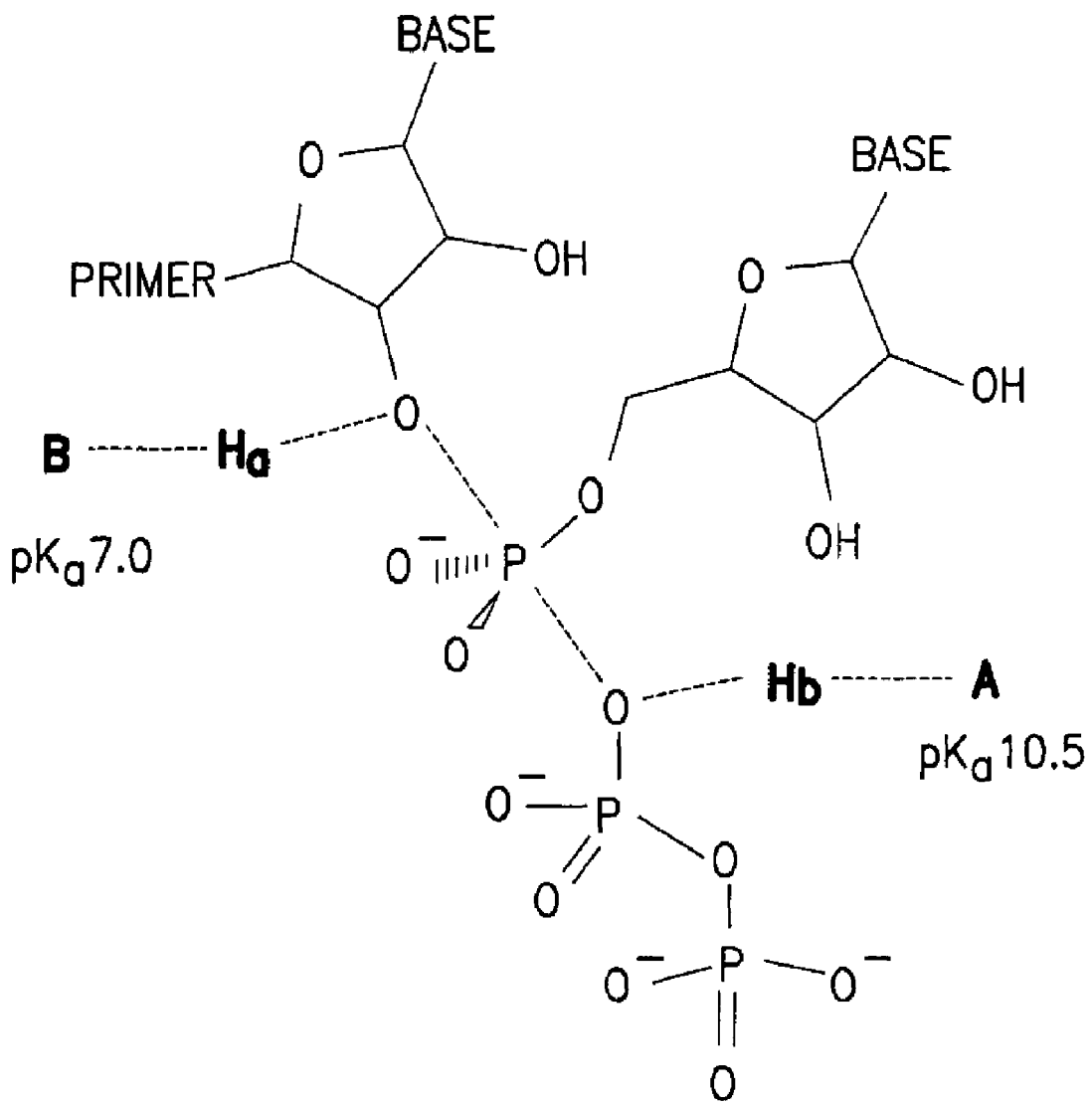
FIG. 6 is a schematic illustration of a general base and a general acid in polymerase-catalyzed nucleotidyl transfer reactions. The data are consistent with a model in which activation of the nucleophile occurs with a $pK_a$ of 7.0 and protonation of the leaving group occurs with a $pK_a$ of 10.5. The $pK_a$ of 7.0 is likely the 3'-OH as this $pK_a$ is modulated by the divalent cation employed and by the atom present at the α-position of the nucleotide substrate.

In the studies described herein, the mechanism of nucleotidyl transfer led to identification of a residue in the active site of all polymerases that facilitates nucleotide addition by protonating the pyrophosphate leaving group; this residue is Lys-359 in PV polymerase (FIG. 6). As shown in Table 1, substitution of different amino acids at this position of the polymerase yields enzymes with varying rates and fidelity of replication. Mutant PV viruses were made each having a modified polymerase gene resulting in either a K359R or K359H substitution. These viruses were shown to be infectious and attenuated in cells relative to WT virus. Because there is a functional equivalent of this residue in all viral polymerases, the capacity for one or more of the PV mutants to protect against challenge by WT PV will set the stage for establishment of a universally applicable, polymerase-mechanism-based strategy for production of virus vaccine strains.

TABLE 1

Mutation Frequency and replication rates for PV polymerase alleles

| Allele | Mutation Frequency sequencing[1] | Mutation Frequency kinetics[2] | Replication Rate[3] |
|---|---|---|---|
| WT | 1.9 | 1/6,000 | 90+/5 s$^{-1}$ |
| G64S | 0.5 | 1/8,600 | 30+/5 s$^{-1}$ |
| K359L | nd[4] | 1/450,000 | 0.50+/0.05 s$^{-1}$ |
| K359H | nd | 1/13,500 | 5.0+/0.5 s$^{-1}$ |
| K359R | nd | 1/9,000 | 5.0+/0.5 s$^{-1}$ |

[1]The calculated average number of mutations per genome based upon sequencing 36,000 nucleotides of capsid coding sequence from 18 viral isolates.
[2]The calculated transition mutation frequency based upon the ratio of the kinetic parameters for correct and incorrect nucleotide incorporation by the PV RdRp allele.
[3]The maximal observed rate constant, kpol, for correct nucleotide incorporation.
[4]Not determined.

The below described preferred embodiments illustrate adaptations of these compositions and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates). Methods of propagating viruses for vaccine production and administering viral vaccines are also generally known in the art and are described in detail, for example, in Vaccine Protocols (Methods in Molecular Medicine) by Andrew Robinson, Martin P. Cranage, and Michael J. Hudson, 2$^{nd}$ ed., Humana Press, Totowa, N.J., 2003; Vaccine Adjuvants and Delivery Systems, by Manmohan Singh, 1$^{st}$ ed., Wiley-Interscience, Hoboken, N.J., 2007; Arvin A. M. and Greenberg H. B., Virology 344:240-249, 2006; and R. Morenweiser, Gene Therapy suppl. 1:S103-S110, 2005. Viral polymerase amino acid sequences and nucleic acid sequences encoding the viral polymerases are known in the art. For example, an HIV-1 RT amino acid sequence having accession number 4139739 is described in Huang et al. (Science 282:

1669-1675, 1998). This HIV-1 RT is based upon a WT background, but has some modifications that allow for proper expression, crystallography and for trapping the enzyme in a covalent attachment with its RNA/DNA substrate. As another example, a human PV nucleic acid sequence having accession number V01148 has been described (Kitamura and Wimmer, Proc. Natl. Acad. Sci. 77:3196-3200, 1980). In yet another example, a human influenza A amino acid sequence having accession number AAY44773 has been described (Ghedin et al., Nature 437:1162-1166, 2005). These references are herein incorporated by reference.

Attenuated Virus

The invention includes attenuated viruses having at least one mutation (e.g., substitution, deletion, insertion) at a conserved amino acid residue in the active site of the viral polymerase. Typically, such a modified polymerase includes a substitution of a lysine residue in the active site of the polymerase that is capable of functioning as a general acid catalyst during a phosphoryl transfer step of a nucleotide incorporation to a leucine, histidine, or arginine residue. This lysine residue as well as neighboring conserved amino acid residues are located on helix-O of A-family polymerases, helix P of B-family polymerases, and on a loop of motif D of RNA dependent RNA polymerases (RdRps) and reverse transcriptases (RTs).

Viral RNA-dependent RNA polymerases have a conserved structure. Lys-359 of PV is present in the "palm" subdomain of the enzyme (FIG. 10A) on conserved structural motif D (FIG. 10B), a motif that has been modeled herein for flu (FIG. 10C). The structural homologue in flu to Lys-359 is Lys-481 of the PB1 subunit (FIG. 10C). This residue is found in influenza A, B and C genotypes (FIG. 10D). Together, these observations reinforce the notion that flu can be attenuated by using the polymerase-mechanism-based strategies described herein.

The comparable residue is located on helix O of A-family polymerases, helix P of B-family polymerases and on the loop of structural motif D of RdRps and RTs (Table 6). Many DNA virus polymerases are B-family polymerases, for example herpes viruses and poxviruses, and have this conserved Lys residue. These viruses can also be attenuated by using the polymerase-mechanism-based strategies described herein. In the experiments described below, PV mutant viruses K359R and K359H were found to replicate.

In some embodiments described herein, an attenuated virus is replication-deficient or non-replicating and includes a foreign nucleic acid that is expressed in a host cell. Examples of such nucleic acids include therapeutic molecules such as for example, cytokines, enzymes and the like.

Accordingly, the present invention also includes a method of preventing or treating a viral infection comprising administering a vaccine of the present invention to an animal in need thereof. For example, viral organisms which cause human diseases according to the present invention include (but are not restricted to) Filoviruses, Herpes viruses, Hepatitisviruses, Retroviruses, Orthomyxoviruses, Paramyxoviruses, Togaviruses, Picornaviruses, Papovaviruses and Gastroenteritisviruses.

In some embodiments, an attenuated virus is replication deficient or replication incompetent and is used in the manufacture of a vaccine. For example, fast replicating virulent viruses used in the preparation of vaccines, such as for example, influenza (e.g. H5N1), HIV, are deleterious to the host cells. An attenuated vaccine strain is advantageous in that the slower replication rate, and if desired, the virus is rendered non-replicating, prevents the virus strain from being lethal to the host due to a fast replication rate. Therefore, in a preferred embodiment, the replication rate is controlled by incorporating a mutation that changes the general acid from lysine to another residue (e.g., leucine, arginine, histidine). Generally, viral replication is decreased at least 24-fold compared to WT virus using the modified polymerases and methods described herein. In another embodiment, the attenuated virus strain is grown in host cells which are normally lysed by the normal virus. Examples include an attenuated HIV strain wherein the HIV strain is grown in human lymphocytes without the immediate lysis or death of these cells.

Nucleic Acids

Modified viral polymerases as described herein are encoded by a viral polymerase gene that has a modification resulting in a mutation (e.g., substitution, deletion, insertion) at an amino acid residue in the active site of the polymerase that is capable of functioning as a general acid catalyst during a phosphoryl transfer step of a nucleotide incorporation reaction. One or more mutations in the conserved region of a viral polymerase modulate the activity of the polymerase (e.g., rate of replication, fidelity, etc.).

In the experiments described below, a PV polymerase was modified to include a substitution of leucine, arginine or histidine for the lysine corresponding to position 359 of the WT PV polymerase amino acid sequence encoded by a nucleic acid sequence having accession number V01148. Corresponding residues in HIV-1 and influenza were also identified. For example, the corresponding lysine in HIV-1 RT corresponds to position 220 of HIV-1 RT amino acid sequence having accession number 4139739. Similarly, the corresponding lysine in influenza corresponds to position 481 of the WT influenza gene segment PB1 amino acid sequence having accession number AA444773.

In some embodiments, a plurality of contiguous nucleic acids in the polymerase gene can be substituted with oligonucleotides which do not code for the conserved amino acid residues. Examples of some preferred oligonucleotides envisioned for this invention include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly $CH_2$—NH—O—$CH_2$, CH, —N($CH_3$)—O—$CH_2$ [known as a methylene(methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—CH). The amide backbones disclosed by De Mesmaeker et al. *Acc. Chem. Res.* 1995, 28:366-374) are also preferred. Also preferred are oligonucleotides having morpholino backbone structures (Summerton and Weller, U.S. Pat. No. 5,034,506). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al. *Science* 1991, 254, 1497). Oligonucleotides may also comprise one or more substituted sugar moieties. Preferred oligonucleotides comprise one of the following: OH, SH, $SCH_3$, F, OCN, $OCH_3OCH_3$, $OCH_3O$ $(CH_2)_nCH_3$, $O(CH_2)_nNH_2$ or $O(CH_2)_nCH_3$ where n is from 1 to about 10; $C_1$ to $C_{10}$ lower alkyl, alkoxyalkoxy, substituted lower alkyl, alkaryl or aralkyl; Cl; Br; CN; $CF_3$; $OCF_3$; O—, S—, or N-alkyl; O—, S—, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—$CH_2CH_2OCH_3$, also known as 2'-O-(2-methoxyethyl)] (Martin et al., *Helv. Chim. Acta*, 1995, 78, 486). Other preferred modifications include 2'-methoxy (2'-O—$CH_3$), 2'-propoxy (2'-$OCH_2CH_2CH_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Oligonucleotides may also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentobiosyl HMC, as well as synthetic nucleobases, e.g., 2-aminoadenine, 2-(methylamino)adenine, 2-(imidazolylalkyl)adenine, 2-(aminoalkylamino)adenine or other heterosubstituted alkyladenines, 2-thiouracil, 2-thiothymine, 5-bromouracil, 5-hydroxymethyluracil, 8-azaguanine, 7-deazaguanine, $N_6$ (6-aminohexyl)adenine and 2,6-diaminopurine. Kornberg, A., DNA Replication, W. H. Freeman & Co., San Francisco, 1980, pp 75-77; Gebeyehu, G., et al. Nucl. Acids Res. 1987, 15:4513). A "universal" base known in the art, e.g., inosine, may be included. 5-Me-C substitutions have been shown to increase nucleic acid duplex stability by 0.6-1.2° C. (Sanghvi, Y. S., in Crooke, S. T. and Lebleu, B., eds., Antisense Research and Applications, CRC Press, Boca Raton, 1993, pp. 276-278) and are presently preferred base substitutions.

Another modification of the oligonucleotides of the invention involves chemically linking to the oligonucleotide one or more moieties or conjugates which enhance the activity or cellular uptake of the oligonucleotide. Such moieties include but are not limited to lipid moieties such as a cholesterol moiety, a cholesteryl moiety (Letsinger et al., *Proc. Natl. Acad. Sci. USA* 1989, 86, 6553), cholic acid (Manoharan et al. *Bioorg. Med. Chem. Let.* 1994, 4, 1053), a thioether, e.g., hexyl-5-tritylthiol (Manoharan et al. *Ann. N.Y. Acad. Sci.* 1992, 660, 306; Manoharan et al. *Bioorg. Med. Chem. Let.* 1993, 3, 2765), a thiocholesterol (Oberhauser et al., *Nucl. Acids Res.* 1992, 20, 533), an aliphatic chain, e.g., dodecandiol or undecyl residues (Saison-Behmoaras et al. *EMBO J.* 1991, 10, 111; Kabanov et al. *FEBS Lett.* 1990, 259, 327; Svinarchuk et al. *Biochimie* 1993, 75, 49), a phospholipid, e.g., di-hexadecyl-rac-glycerol or triethylammonium 1,2-di-O-hexadecyl-rac-glycero-3-H-phosphonate (Manoharan et al. *Tetrahedron Lett.* 1995, 36, 3651; Shea et al. *Nucl. Acids Res.* 1990, 18, 3777), a polyamine or a polyethylene glycol chain (Manoharan et al. *Nucleosides & Nucleotides* 1995, 14, 969), or adamantane acetic acid (Manoharan et al. *Tetrahedron Lett.* 1995, 36, 3651). Oligonucleotides comprising lipophilic moieties, and methods for preparing such oligonucleotides are known in the art, for example, U.S. Pat. Nos. 5,138,045, 5,218,105 and 5,459,255.

It is not necessary for all positions in a given oligonucleotide to be uniformly modified, and in fact more than one of the aforementioned modifications may be incorporated in a single oligonucleotide or even at within a single nucleoside within an oligonucleotide. The present invention also includes oligonucleotides which are chimeric oligonucleotides as hereinbefore defined.

In another embodiment, a nucleic acid molecule of the present invention is conjugated with another moiety including but not limited to abasic nucleotides, polyether, polyamine, polyamides, peptides, carbohydrates, lipid, or polyhydrocarbon compounds. Those skilled in the art will recognize that these molecules can be linked to one or more of any nucleotides comprising the nucleic acid molecule at several positions on the sugar, base or phosphate group.

RNA Interference (RNAi): RNAi is a remarkably efficient process whereby double-stranded RNA (dsRNA, also referred to herein as siRNAs, for small interfering RNAs, or ds siRNAs, for double-stranded small interfering RNAs) induces the sequence-specific degradation of homologous mRNA in animals and plant cells (Hutvagner and Zamore, Curr. Opin. Genet. Dev., 12:225-232 (2002); Sharp, Genes Dev., 15:485-490 (2001)). In mammalian cells, RNAi can be triggered by duplexes of small interfering RNA (siRNA) (Chiu et al., Mol. Cell., 10:549-561 (2002); Elbashir et al., Nature, 411:494-498 (2001)), or by micro-RNAs (miRNA), functional small-hairpin RNA (shRNA), or other dsRNAs which are expressed in vivo using DNA templates with RNA polymerase III promoters (Zeng et al., Mol. Cell, 9:1327-1333 (2002); Paddison et al., Genes Dev., 16:948-958 (2002); Lee et al., Nature Biotechnol., 20:500-505 (2002); Paul et al., Nature Biotechnol., 20:505-508 (2002); Tuschl, T., Nature Biotechnol., 20:440-448 (2002); Yu et al., Proc. Natl. Acad. Sci. USA, 99(9):6047-6052 (2002); McManus et al., RNA, 8:842-850 (2002); Sui et al., Proc. Natl. Acad. Sci. USA, 99(6):5515-5520 (2002)).

The agents described herein can include dsRNA molecules that are targeted to (i.e., bind to) regions of residues conserved between polymerases and/or structural homologous regions between different polymerases. For example, lysine at position 359 of the poliovirus polymerase. (See, also, for example, Tables 1 and 6). Structurally homologous regions are readily identifiable using various programs, such as BLAST etc.

The dsRNA molecules typically include 16-30, e.g., 16, 17, 18, 19, 20, 21, 22, 23, 24, 25, 26, 27, 28, 29, or 30 nucleotides in each strand, wherein one of the strands is substantially identical, e.g., at least 80% (or more, e.g., 85%, 90%, 95%, or 100%) identical, e.g., having 3, 2, 1, or 0 mismatched nucleotide(s), to a target region in the mRNA, and the other strand is identical or substantially identical to the first strand. Each strand can also have one or more overhanging (i.e., non-complementary) nucleotides, e.g., one, two, three, four or more overhanging nucleotides, e.g., dTdTdT.

The dsRNA molecules can be chemically synthesized, or can be transcribed in vitro from a DNA template, or in vivo from, e.g., shRNA. The dsRNA molecules can be designed using any method known in the art; a number of algorithms are known in the art, see, e.g., Tuschl et al., Genes Dev 13(24):3191-7 (1999), and many are available on the internet, e.g., on the websites of Dharmacon (Lafayette, Colo.) or Ambion (Austin, Tex.).

Negative control siRNAs should have the same nucleotide composition as the selected siRNA, but without significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

micro RNA (miRNAs) of approximately 22 nucleotides can be used to regulate gene expression at the post transcriptional or translational level. miRNAs can be excised in the cell from an approximately 70 nucleotide precursor RNA stem-loop by Dicer, an RNase III-type enzyme, or a homolog thereof. By substituting the stem sequences of the miRNA precursor with miRNA sequence complementary to the target mRNA, a vector construct that expresses the novel miRNA can be used to produce siRNAs to initiate RNAi against specific mRNA targets in mammalian cells (Zeng (2002), supra). When expressed by DNA vectors containing polymerase III promoters, micro-RNA designed hairpins can silence gene expression (McManus (2002), supra).

dsRNA can be delivered directly into cells in vivo or in vitro using methods known in the art, e.g., cationic liposome transfection, nanoparticles, and electroporation, or expressed in vivo or in vitro from recombinant DNA constructs that allow longer-term target gene suppression in cells, including mammalian Pol III promoter systems (e.g., H1 or U6/snRNA promoter systems (Tuschl (2002), supra) capable of expressing functional double-stranded siRNAs; (Bagella et al., J. Cell. Physiol. 177:206-213 (1998); Lee et al. (2002), supra; Miyagishi et al. (2002), supra; Paul et al. (2002), supra; Yu et al. (2002), supra; Sui et al. (2002), supra).

Viral-mediated delivery mechanisms can also be used to induce specific silencing of targeted genes through expression of siRNA, for example, by generating recombinant adenoviruses harboring siRNA under RNA Pol II promoter transcription control (Xia et al. (2002), supra). Transcriptional termination by RNA Pol III occurs at runs of four consecutive T residues in the DNA template, providing a mechanism to end the siRNA transcript at a specific sequence. The dsRNA thus produced is complementary to the sequence of the target gene in 5'-3' and 3'-5' orientations, and the two strands of the siRNA can be expressed in the same construct or in separate constructs. Hairpin siRNAs, driven by H1 or U6 snRNA promoter and expressed in cells, can inhibit target gene expression (Bagella et al. (1998), supra; Lee et al. (2002), supra; Miyagishi et al. (2002), supra; Paul et al. (2002), supra; Yu et al. (2002), supra; Sui et al. (2002) supra). Constructs containing siRNA sequence under the control of T7 promoter also make functional siRNAs when cotransfected into cells with a vector expression T7 RNA polymerase (Jacque (2002), supra).

In an animal, whole-embryo electroporation can efficiently deliver synthetic siRNA into post-implantation mouse embryos (Calegari et al., Proc. Natl. Acad. Sci. USA, 99(22): 14236-40 (2002)). In adult mice, efficient delivery of siRNA can be accomplished by "high-pressure" delivery technique, a rapid injection (within 5 seconds) of a large volume of siRNA containing solution into animal via the tail vein (Liu (1999), supra; McCaffrey (2002), supra; Lewis, Nature Genetics 32:107-108 (2002)). Local delivery can also be used, e.g., with a carrier such as lipiodol (iodine in oil) to facilitate delivery into cells.

Engineered RNA precursors, introduced into cells or whole organisms as described herein, can be used for the production of a desired siRNA molecule. Such an siRNA molecule can then associate with endogenous protein components of the RNAi pathway to bind to and target a specific mRNA sequence for cleavage and destruction. In this fashion, the mRNA to be targeted by the siRNA generated from the engineered RNA precursor will be depleted from the cell or organism, leading to a decrease in the concentration of the protein encoded by that mRNA in the cell or organism. Additional information regarding the use of RNAi can be found in RNA Interference Editing, and Modification: Methods and Protocols (Methods in Molecular Biology), Gott, Ed. (Humana Press, 2004);

Antisense Polynucleotides: An "antisense" nucleic acid can include a nucleotide sequence that is complementary to a "sense" nucleic acid encoding regions of residues conserved between polymerases and/or structural homologous regions between different polymerases. For example, lysine at position 359 of the poliovirus polymerase. (See, also, for example, Tables 1 and 6).

Based upon the sequences disclosed herein, one of skill in the art can easily choose and synthesize any of a number of appropriate antisense molecules for use in accordance with the present invention. For example, a "gene walk" comprising a series of oligonucleotides of 15-30 nucleotides spanning the length of regions of residues conserved between polymerases and/or structural homologous regions between different polymerases. For example, lysine at position 359 of the poliovirus polymerase. (See, also, for example, Tables 1 and 6). The nucleic acid can be prepared, followed by testing for inhibition of viral replication. Optionally, gaps of 5-10 nucleotides can be left between the oligonucleotides to reduce the number of oligonucleotides synthesized and tested. Other methods, including computational analysis, RNAse H mapping, and antisense-oligonucleotide scanning microarrays, can also be used (see, e.g., DNA Microarrays: A Practical Approach, Schena, Ed. (Oxford University Press 1999; Scherr and Rossi, *Nucl. Acids Res.,* 26(22):5079-5085 (1998)).

An antisense nucleic acid can be designed such that it is complementary to the entire coding region of a target polymerase but can also be an oligonucleotide that is antisense to only a portion of the coding or noncoding region of the target mRNA. For example, the antisense oligonucleotide can be complementary to a region surrounding the translation start site of the target mRNA, e.g., between the −10 and +10 regions of the target gene nucleotide sequence of interest. Preferably, the antisense nucleic acid is targeted to regions of residues conserved between polymerases and/or structural homologous regions between different polymerases. For example, lysine at position 359 of the poliovirus polymerase. (See, also, for example, Tables 1 and 6). An antisense oligonucleotide can be, for example, about 7, 10, 15, 20, 25, 30, 35, 40, 45, 50, 55, 60, 65, 70, 75, 80, or more nucleotides in length.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest).

Antisense nucleic acid molecules are typically administered to a subject (e.g., by direct injection at a tissue site), or generated in situ such that they hybridize with or bind to mRNA and/or DNA encoding regions of residues conserved between polymerases and/or structural homologous regions between different polymerases. For example, lysine at position 359 of the poliovirus polymerase.

Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter can be used.

In yet another embodiment, an antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al., *Nucleic Acids. Res.* 15:6625-6641 (1987)). The antisense nucleic acid molecule can also comprise a 2'-o-methylribonucleotide (Inoue et al. *Nucleic Acids Res.* 15:6131-6148 (1987)) or a chimeric RNA-DNA analogue (Inoue et al. *FEBS Lett.,* 215:327-330 (1987)).

The potential sequences that can be targeted for triple helix formation can be increased by creating a so called "switchback" nucleic acid molecule. Switchback molecules are synthesized in an alternating 5'-3',3'-5' manner, such that they base pair with first one strand of a duplex and then the other, eliminating the necessity for a sizeable stretch of either purines or pyrimidines to be present on one strand of a duplex.

Ribozymes: Ribozymes are a type of RNA that can be engineered to enzymatically cleave and inactivate other RNA targets in a specific, sequence-dependent fashion. By cleaving the target RNA, ribozymes inhibit translation, thus preventing the expression of the target gene. Ribozymes can be chemically synthesized in the laboratory and structurally modified to increase their stability and catalytic activity using methods known in the art. Alternatively, ribozyme genes can be introduced into cells through gene-delivery mechanisms known in the art. A ribozyme having specificity for regions of residues conserved between polymerases and/or structural homologous regions between different polymerases can include one or more sequences complementary to these nucleotide sequences and a sequence having known catalytic sequence responsible for mRNA cleavage (see U.S. Pat. No. 5,093,246 or Haselhoff and Gerlach, *Nature,* 334:585-591 (1988)).

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification.

All publications and patent documents cited in this application are incorporated by reference in pertinent part for all purposes to the same extent as if each individual publication or patent document were so individually denoted. By their citation of various references in this document, Applicants do not admit any particular reference is "prior art" to their invention.

Administration of Compositions The vaccine compositions, attenuated viruses and compositions including attenuated viruses described herein can be introduced into a cell or administered to a subject (e.g., a human) in any suitable formulation by any suitable method. For example, the compositions and anti-viral vaccines described herein may be injected directly into a cell, such as by microinjection. As another example, the compositions and anti-viral vaccines described herein may be directly introduced into a subject (e.g., human), including by intravenous (IV) injection, intraperitoneal (IP) injection, subcutaneous injection, intramuscular injection, or in situ injection into target tissue. For example, a conventional syringe and needle can be used to inject a suspension containing an anti-viral vaccine as described herein into a subject. Depending on the desired route of administration, injection can be in situ (i.e., to a particular tissue or location on a tissue), IM, IV, IP, or by another parenteral route. Compositions and anti-viral vaccines as described herein can also be administered by oral administration, inhalation, transdermal administration, or suppository applications.

The vaccines of the present invention may additionally contain suitable diluents, adjuvants and/or carriers. Preferably, the vaccines contain an adjuvant which can enhance the immunogenicity of the vaccine in vivo. The adjuvant may be selected from many known adjuvants in the art including the lipid-A portion of gram negative bacteria endotoxin, trehalose dimycolate of mycobacteria, the phospholipid lysolecithin, dimethyldioctadecyl ammonium bromide (DDA), certain linear polyoxypropylene-polyoxyethylene (POP-POE) block polymers, aluminum hydroxide, and liposomes. The vaccines may also include cytokines that are known to enhance the immune response including GM-CSF, IL-2, IL-12, TNF and IFNγ.

The dose of the vaccine may vary according to factors such as the disease state, age, sex, and weight of the individual, and the ability of antibody to elicit a desired response in the individual. Dosage regime may be adjusted to provide the optimum therapeutic response. For example, several divided doses may be administered daily or the dose may be proportionally reduced as indicated by the exigencies of the therapeutic situation. The dose of the vaccine may also be varied to provide optimum preventative dose response depending upon the circumstances.

EXAMPLES

The present invention is further illustrated by the following specific examples. The examples are provided for illustration only and should not be construed as limiting the scope of the invention in any way.

Example 1

Two Proton Transfer Reactions in the Rate-Limiting Transition State for Nucleotidyl Transfer Catalyzed by RNA- and DNA-Dependent RNA and DNA Polymerases Materials and Methods Materials: [γ-$^{32}$P]ATP (>7000 Ci/mmol) was purchased from ICN; [α-$^{32}$P] ATP (3000 Ci/mmol was from New England Nuclear; nucleoside 5'-triphosphates, (ultra pure solutions), were from Amersham Pharmacia Biotech, Inc; adenosine 5'-O-(1-thiotriphosphate) (ATPαS) was from Axxora Biochemicals (San Diego, Calif.); D$_2$O was purchased from Isotec (Miamisburg, Ohio); deuterated glycerol was from Cambridge Isotope Laboratories (Andover, Mass.); all RNA oligonucleotides were from Dharmacon Research, Inc. (Boulder, Colo.); all DNA oligonucleotides were from Integrated DNA Technologies (Coralville, Iowa); T4 polynucleotide kinase was from New England Biolabs, Inc; all other reagents were of the highest grade available from Sigma, Fisher, or VWR.

Abbreviations: DdRp, DNA-dependent RNA polymerase DdDp, DNA-dependent DNA polymerase; RNAp, DNA-dependent RNA polymerase; RT, reverse transcriptase; PV, poliovirus; S/S, symmetrical primer/template substrate; CQF, chemical quench flow instrument; SF, stopped-flow instrument; 2AP, 2-aminopurine; SDIE, solvent deuterium isotope effect; DTT, dithiothreitol; BME, beta-mercaptoethanol; EDTA, ethylenediamino tetra acetic acid; NP-40, nonident P-40; PMSF, phenylmethylsulfonyl fluoride; PEI, Polyethyleneimine.

PV 3D$^{pol}$-Catalyzed Nucleotide Incorporation Experiments.

Stopped-flow experiments: Stopped-flow experiments were performed using a Model SF-2001 stopped-flow apparatus (Kintek Corp., Austin, Tex.) equipped with a water-bath. All reactions were performed at 30° C. Reactions were performed in two different sets of buffers. Reactions in HEPES refer to reactions performed by incubating 1 μM enzyme with 1 μM sym/sub (0.5 μM duplex) at room temperature for 3 minutes in 50 mM HEPES, pH 7.5, 10 mM 2-mercaptoethanol, 5 mM MgCl$_2$, 60 mM ZnCl$_2$, and then allowed to equilibrate to 30° C. in the sample compartment then rapidly mixed with the nucleotide prepared by using the same buffer. Reactions in MTCN or MHCN refer to reactions performed by incubating 1 μM enzyme with 1 μM sym/sub (0.5 μM duplex) in 1 mM HEPES pH 7.5 at room temperature for 3 minutes and then allowed to equilibrate to 30° C. in the sample compartment then rapidly mixed with the nucleoside triphosphate substrate in a solution containing 2×MTCN buffer at the indicated pH. 1×MTCN buffer is: 50 mM MES, 25 mM TRIS, 25 mM CAPS and 50 mM NaCl. The other buffer components for both enzyme-sym/sub and nucleotide solutions were the same. 1×MHCN buffer is: 50 mM MES, 25 mM HEPES, 25 mM CAPS and 50 mM NaCl. 3D$^{pol}$ was diluted into enzyme buffer (50 mM HEPES, pH 7.5, 10 mM 2-mercaptoethanol, 60 μM ZnCl$_2$, and 20% glycerol) immediately prior to use. The volume of enzyme added to any reaction was always equal to one-twentieth the total reaction volume. For reactions with a final ATP concentration higher than 1 mM, the amount of free Mg$^{2+}$ was kept constant by increasing the amount of MgCl$_2$ in the reaction to 5 mM plus the ATP concentration above 1 mM. For example, in a reaction containing 5 mM ATP, the final Mg$^{2+}$ concentration was adjusted to 9 mM. The excitation wavelength used was 313 nm. Fluorescence emission was monitored by using a 370 nm cut-on filter (model E370LP, Chroma Technology Corp., Rockingham, Vt.). Reactions utilizing the nonhydrolyzable ATP analog α,β-methyleneadenosine 5'-triphosphate (AMPCPP) were done to investigate the possibility that observed changes in fluorescence resulted from alterations in the 2AP environment as a consequence of nucleotide binding. This proved not to be the case as changes in fluorescence were minimal over the time frame under investigation. The concentrations of nucleotide substrates and contents of buffers used are indicated in the appropriate figure and table legends. Rate constants for nucleotide incorporation were obtained by using the data analysis software of the instrument.

Rapid Chemical-Quench-Flow Experiments.

Rapid mixing/quenching experiments were performed by using a Model RQF-3 chemical-quench-flow apparatus (KinTek Corp., Austin, Tex.). $3D^{pol}$-sym/sub complexes and all buffer solutions were prepared in the same way as for the stopped-flow experiments described above. Reactions were quenched by addition of HCl to a final concentration of 1 M. Immediately after the addition of HCl, the solution was neutralized by addition of 1 M KOH and 300 mM Tris base (final concentration). The concentrations of nucleotide substrates and contents of buffers used are indicated in the appropriate figure and table legends.

Rapid-Quench Product Analysis: Denaturing PAGE.

An equal volume of loading/quenching dye (85% formamide, 0.025% bromophenol blue, and 0.025% xylene cyanol, 90 mM EDTA) was added to 10 μl of the quenched reaction mixtures and heated to 70° C. for 2-5 min prior to loading 5 μl on a denaturing 23% polyacrylamide gel containing 1×TBE (2 mM EDTA, 89 mM boric acid, 87 mM Tris) and 7 M urea. Electrophoresis was performed in 1×TBE at 90 W. Gels were visualized by using a phosphorimager and quantified by using the ImageQuant software (Molecular Dynamics).

Steady-State Incorporation of AMP into Sym/Sub.

Steady-state experiments were performed by incubating 1 μM $3D^{pol}$ with 30 μM sym/sub (15 μM duplex) in 1 Mm HEPES buffer at pH 7.5 for 90 seconds at 30° C. then mixed with ATP in 2×MTCN buffer at pH 7.5. Reactions were quenched at various times by mixing with an equal volume of loading/quenching dye. Product analysis was performed by using denaturing PAGE as described above. All buffers and solutions were prepared in either $H_2O$ or $D_2O$ for each experiment. The pD was used instead of pH for the solutions in $D_2O$ and was adjusted according to pD=pH+0.4.

Proton Inventory.

Enzymes, substrates and buffers for the proton-inventory experiments were prepared in 100% water or 100% $D_2O$ followed by mixing at the appropriate ratio to obtain 0, 25, 50, 75 or 100% $D_2O$. Deuterated glycerol was used in all solutions in $D_2O$. All data collection was performed in the stopped-flow instrument as indicated above. The pD was used instead of pH for the solutions in $D_2O$ as described above.

Data Analysis.

Time courses at fixed nucleotide concentrations were fit to the single exponential function:

$$[product]=A^{*}\exp(-k_{obs}{*}t)+C \quad (1)$$

where A is the amplitude of the burst, $k_{obs}$ is the observed first-order rate constant describing the burst, t is the time, and C is a constant. Time courses from the stopped-flow instrument were fit to the same equation using the instrument software. Data were fit by nonlinear regression using the program KaleidaGraph (Synergy Software, Reading, Pa.). The apparent binding constant ($K_{D,app}$) and maximal rate constant for nucleotide incorporation ($k_{pol}$) were determined using the equation:

$$k_{obs}=k_{pol}[NTP]/K_{D,app}+[NTP] \quad (2)$$

The pKa values for the pH dependence of $k_{pol}$ were obtained by fitting to a model describing two-ionizable groups (Bevilacqua, P. C. (2003) *Biochemistry* 42, 2259-65.):

$$k_{pol}=k_{ind}/(1+10^{\wedge}(pK_{a1}-pH)+(pH-pK_{a2})) \quad (3)$$

or one-ionizable group (Bevilacqua, P. C. supra.):

$$k_{pol}=k_{ind}/(1+10^{\wedge}(pK_a-pH)) \quad (4)$$

where $k_{ind}$ is the pH-independent rate constant.

The proton-inventory data were fit to the modified Gross-Butler equation for a two proton-transfer model (Schowen, R. L. & Venkatasubban, K. S. (1985) CRC Crytical reviews in Biochemistry 17, 1-44):

$$k_n/k_{H2O}=(1-n+n^{*}\phi_1)(1-n+n^{*}\phi_2) \quad (5)$$

or for a one-proton-transfer model (Schowen et al):

$$k_n/k_{H2O}=(1-n+n^{*}\phi) \quad (6)$$

where $k_n$ is the observed rate constant at the different percentages of $D_2O$, $k_{H2O}$ is the observed rate constant in water, n is the mole fraction of $D_2O$ and ϕ is the inverse of the isotope effect for each ionizable group.

Equilibrium and rate constants reported were determined independently at least twice. Error was propagated through products and quotients by using equation 6:

$$\Delta z=((\Delta x/x)^2+(\Delta y/y)^2)^{\wedge}{-1/2}{*}z \quad (7)$$

where x and y are the primary data, z is the product or quotient of x and y, and Δx, Δy and Δz are the corresponding error values (Aikens, D. A., Bailey, R. A., Moore, J. A., Giachino, G. G. & Tomkins, R. P. T. (1984) Principles and techniques for an integrated chemistry laboratory (Waveland Press, Prospect Heights, Ill.)).

Expression and Purification of RB69 DdDp.

RB69 DdDp was expressed in BL21 (DE3) cells. Frozen cells were thawed and suspended in lysis buffer (100 mM $KPO_4$ pH 8.0, 20% glycerol, 20 mM DTT, 0.5 mM EDTA pH 8.0, 2.8 μg/mL pepstatin A, 2.0 μg/mL leupeptin) and lysed by passing through a French press at 1000 psi. Immediately after lysis, NP-40 was added to 0.1% (v/v) and PMSF was added to 2 mM. Polyethyleneimine (PEI) was added drop wise at 4° C. to a final concentration of 0.25% (v/v) and stirred for 30 min. This suspension was then centrifuged at 75,000×g for 30 min at 4° C. The supernatant was decanted and collected, and ground ammonium sulfate powder was slowly added to 60% saturation at 4° C. and stirred for 30 min. The ammonium sulfate precipitate was suspended in Buffer A (50 mM Tris pH 8.0, 20% glycerol, 10 mM DTT, 0.1% NP-40) and dialyzed overnight against 1 L Buffer A containing 75 mM NaCl using a 12-14,000 Da MWCO membrane. After dialysis, the sample was diluted in Buffer A to a final NaCl concentration of 50 mM. The sample was loaded onto a phosphocellulose column (approximately 1 mL bed volume/25 mg total protein) at a flow rate of 1 mL/min. The column was washed with ten column volumes of Buffer A containing 50 mM NaCl and the protein was eluted with Buffer A containing 150 mM NaCl. Fractions were pooled based upon their purity on 8% SDS-PAGE gels. The pooled fractions were diluted in Buffer A to a final salt concentration of 50 mM. The sample was loaded onto a Q-Sepharose column (1 mL bed volume/40 mg of protein) at 1 mL/min. The column was washed with ten column volumes of Buffer A containing 50 mM NaCl and the protein eluted with Buffer A containing 150 mM NaCl. Protein-containing fractions were pooled as before. The protein was concentrated using a small (0.5 mL) Q-Sepharose column. Loading and washing of the column was as described above. Elution was performed with Buffer A containing 500 mM NaCl.

Expression and Purification of T7 DdRp.

Purification of T7 DdRp was done using the same protocol as for RB69 DdDp with the following modifications: 1. Ammonium sulfate was added to 40% saturation. 2. The phosphocellulose column was eluted using a linear gradient (6 column volumes) from 50 mM-700 mM NaCl in Buffer A. 3. The Q-Sepharose column was loaded and washed, and the protein eluted using a linear gradient (6 column volumes) from 50 mM-400 mM NaCl in Buffer A. Protein-containing fractions were pooled as before. Additional steps to concentrate the protein were not necessary.

Expression and Purification of HIV RT.

HIV RT was expressed and purified as described previously (Le Grice, S. F. & Gruninger-Leitch, F. (1990) *Eur J Biochem* 187, 307-14).

Solvent Deuterium Isotope Effect and Proton Inventory for RB69 DdDp.

Experiments were done in the stopped-flow instrument at 25° C. essentially as described (Yang, G., et al. (2002) *Biochemistry* 41, 2526-34.) with minor modifications. The assays were done in 1×MTCN pH 7.5, 10 mM $MgCl_2$, 1 mM dATP with 1 µM RB69 WT enzyme and 150 nM primer-template substrate. The DNA primer used was: 5'-CCGAC-CAGCCTTG-3' (SEQ ID NO: 1); the DNA template used was: 5'-AAAGC(2AP)TCAAGGCTGGTCGG-3' (SEQ ID NO: 2). The solvent deuterium isotope effect and proton inventory were performed as described above for $3D^{pol}$.

Solvent Deuterium Isotope Effect and Proton Inventory for T7 DdRp.

Experiments were done in the stopped-flow instrument at 30° C. essentially as described for $3D^{pol}$ with minor modifications. One µM RNA primer, 5'-UUUUGCCGCGCC-3' (SEQ ID NO: 3), was annealed to 1 µM DNA template, 5'-GGAATGC(2AP)TGGCGCGGC-3' (SEQ ID NO: 4), and then incubated with 1.6 µM T7 WT for 10 minutes at room temperature in 1×MTCN pH 7.5, 10 mM BME, and 5 mM $MgCl_2$. The reaction was started by mixing the T7-primer-template complex with 3 mM ATP in MTCN pH 7.5, 10 mM BME, 7 mM $MgCl_2$, 100 mM NaCl (additional). The solvent deuterium isotope effect and proton inventory were performed as described above for $3D^{pol}$.

Solvent Deuterium Isotope Effect and Proton Inventory for HIV-RT.

Pre steady state experiments were done in the chemical-quench-flow instrument at 37° C. essentially as described (Götte, M., et al (2000) *Journal of Virology*, 3579-3585) with some modifications: 2 µM $_{32}$P-labeled DNA primer, 5'-TTAAAAGAAAAGGGGGGACTGGA-3' (SEQ ID NO: 5), was annealed with 2.2 µM DNA template, 5'-CGTTGG-GAGTGAATTAGCCCTTCCAGTC-CCCCCTTTTCTTTTAAAAAGTGGCTAAGA-3' (SEQ ID NO: 6), and incubated with 4 µM RT in a solution containing no metals. The reaction was started by addition of 200 µM dATP in reaction buffer containing 10 mM $MgCl_2$. After mixing, reactant concentrations were reduced by 50%. Reactions were performed by using a chemical quench flow instrument. Product analysis was performed essentially as described for PV $3D^{pol}$ with the following modifications. 1. Unlabeled DNA primer was added to the loading/quenching dye at a concentration 100-fold that of the labeled primer as described previously (Arnold, J. J., Ghosh, S. K., Bevilacqua, P. C. & Cameron, C. E. (1999) *Biotechniques* 27, 450-2, 454, 456). 2. A 15% polyacrylamide gel containing 40% formamide was used.

TABLE 2

Solvent deuterium isotope effect and two proton transfer reactions are observed during nucleotidyl transfer by all polymerases.

| Enzyme | $D_2O$ Effect | Proton inventory |
|---|---|---|
| PV RdRp | 3 ± 0.5 | 2 |
| RB69 DdDp | 4 ± 0.1 | 2 |
| T7 DdRp | 5 ± 1 | 2 |
| HIV RT | 2 ± 0.5 | In progress |

Results

A rapid fluorescence assay for evaluation of $3D^{pol}$-catalyzed nucleotide incorporation was developed. This assay has been employed to evaluate the pH dependence of this reaction, providing evidence for two ionizable groups in the rate limiting step for nucleotide incorporation. Under physiological conditions, a solvent deuterium isotope effect was observed. A proton inventory experiment provided the first observation of a two-proton transfer reaction during polymerase-catalyzed nucleotide incorporation. Two proton-transfer reactions were also observed for nucleotidyl-transfer reactions catalyzed by the RB69 DNA-dependent DNA polymerase, T7 DNA-dependent RNA polymerase and HIV reverse transcriptase. Together, these data provide very compelling evidence for use of a general base and a general acid in polymerase-catalyzed nucleotidyl-transfer reactions.

Two ionizable groups are required for RdRp-catalyzed nucleotidyl transfer. Because chemistry is at least partially rate limiting for 3Dpol-catalyzed nucleotide incorporation, we reasoned that it should be possible to obtain insight into the proton transfers occurring during the rate-limiting transition state by evaluating the pH dependence of the reaction. In order to maximize the amount of kinetic data obtained, we developed and validated a stopped-flow fluorescence assay for $3D_{pol}$ that employed an RNA template containing 2-aminopurine (FIG. 7 and FIG. 8). In order to vary the pH of the reaction without varying the ionic strength, we chose the MTCN and MHCN buffer systems (Ellis, K. J. & Morrison, J. F. (1982) *Methods Enzymol* 87, 405-426). The buffers were comparable, yielding $K_{D,app}$ and $k_{pol}$ values of 200±20 µM and 50±10 $s^{-1}$, respectively, at pH 7.5 (Table 3). The higher $K_{D,app}$ value for ATP relative to previous buffer systems employed was caused by the increased ionic strength of the MTCN and MHCN buffers.

TABLE 3

Effect of buffer composition on kinetic constants for $3D^{pol}$-catalyzed nucleotide incorporation[a].

| Buffer | Device | $K_{D, app}$ (µM) | $k_{pol}$ ($s^{-1}$) |
|---|---|---|---|
| HEPES | SF | 70 ± 10 | 70 ± 10 |
| HEPES | CQF | 70 ± 10 | 80 ± 10 |
| MTCN | SF | 200 ± 20 | 50 ± 10 |
| MHCN | SF | 200 ± 20 | 50 ± 10 |

[a]Buffers are described in materials and methods. "SF" indicates that experiments were performed in a stopped flow instrument. "CQF: indicates that experiments were performed in a chemical-quench-flow instrument. Kinetic constants are reported to one significant figure.

The $K_{D,app}$ and $k_{pol}$ values for nucleotide incorporation were measured at different pH values in $Mg^{2+}$ or $Mn^{2+}$ (Table 4). Experiments were limited to pH 10 in $Mg^{2+}$ and pH 9 in $Mn^{2+}$ due to nucleotide precipitation at higher pH values. Values for $k_{pol}$ were plotted as a function of pH (FIG. 2). In $Mg^{2+}$, a bell-shaped curve was observed, indicative of two ionizable groups. The data were fit to equation 3, yielding $pK_a$ values of 7.1±0.1 and 10.5±0.1. In $Mn^{2+}$, a similar pH dependence was observed for the acidic arm of the profile, but with a shift in $pK_a$ of about one pH unit to 8.2±0.1. These data fit well to a single ionization model. However, we could not rule out a two-ionization model in $Mn^{2+}$. The pH rate profile that would be observed with $pK_a$ values of 8.2 and 10.5 is shown in FIG. 2B (dashed line). Data above pH 9 would be required to distinguish between the one and two-ionization models.

10.0, the solvent deuterium isotope effect was investigated. If proton transfers are occurring during the rate-limiting steps measured by the nucleotide incorporation assay, then an isotope effect should be apparent. In $Mg^{2+}$ at pH 7.5, an isotope effect of 3±0.5 was observed for AMP incorporation in the pre-steady-state (FIG. 3A). In $Mn^{2+}$ at pH 7.5, an isotope effect of 7±2 was observed (FIG. 3B). The dependence of the magnitude of the isotope effect on the divalent cation employed was consistent with previous observations that chemistry is partially rate limiting in $Mg^{2+}$ but solely rate

TABLE 4

Kinetic constants for AMP incorporation by PV $3D_{pol}$ in $Mg^{2+}$ and $Mn^{2+a}$.

| Metal | | pH 6.0 | pH 6.5 | pH 7.0 | pH 7.5 | pH 8.0 | pH 9.0 | pH 9.5 | pH 10.0 |
|---|---|---|---|---|---|---|---|---|---|
| $Mg^{2+}$ | $K_{D,app}{}^{b}$ | 10 ± 1 | 30 ± 5 | 80 ± 10 | 200 ± 20 | 300 ± 30 | 500 ± 50 | 900 ± 70 | 1000 ± 100 |
|  | $k_{pol}{}^{b}$ | 7 ± 1 | 10 ± 1 | 40 ± 5 | 50 ± 5 | 60 ± 10 | 70 ± 10 | 60 ± 10 | 50 ± 10 |
| $Mn^{2+}$ | $K_{D,app}$ |  | 2 ± 1 | 3 ± 1 | 5 ± 1 | 20 ± 2 | 20 ± 3 |  |  |
|  | $k_{pol}$ |  | 3 ± 1 | 7 ± 1 | 10 ± 1 | 30 ± 5 | 60 ± 10 |  |  |

$^a$Experiments were performed as described in materials and methods.
$^b$Units for $K_{D,app}$ and $k_{pol}$ are μM and $s^{-1}$ respectively. Values are reported to one significant figure.

Rate limiting steps as a function of pH. In order to determine whether rate-limiting steps were changing as a function of pH, we evaluated the phosphorothioate (thio) effect over the pH range evaluated above (Table 5). For $3D^{pol}$, chemistry is partially rate limiting in $Mg^{2+}$ at pH 7.5. Under these conditions, the observed thio effect was 3±0.3 (Table 5). At pH values lower than 7.5, chemistry was clearly at least partially rate limiting as the value for the thio effect either did not change (pH 7.0) or increased (pH 6.0) (Table 5). A thio effect was also observed at pH values of 8.0 and 9.0; however, none was observed at pH 10 (Table 5). Interestingly, the decrease in the value of the thio effect above pH 7.5 was due to a specific increase in the observed rate constant for AMPαS incorporation without any significant effect on that for AMP incorporation (Table 5). In $Mn^{2+}$ at pH 7.5, chemistry is the sole rate limiting step. From pH 6.0 to 9.0, the thio effect ranged from 7 to 5 (Table 5), consistent with chemistry remaining kinetically significant over this pH range.

limiting in $Mn^{2+}$. However, to rule out conformational perturbations as the cause of the observed isotope effects, AMP incorporation in the steady state was evaluated.

The rate-limiting step in the steady state is dissociation of enzyme from the primer template substrate. An isotope effect on this step would not be expected. As shown in FIGS. 3C and 3D, an isotope effect was not observed. It was concluded that the solvent deuterium isotope effect is a useful probe for chemistry as a rate-limiting step during nucleotide incorporation. Evaluation of the pH dependence of the solvent deuterium isotope effect in $Mg^{2+}$ showed a constant value of 2±0.2 from pH 7.5 to 10.0 (Table 5). Therefore, chemistry is partially rate limiting over the entire pH range evaluated.

Two proton-transfer reactions in the rate-limiting transition state for RdRp catalyzed nucleotidyl transfer. The existence of a solvent deuterium isotope effect on the rate constant for nucleotide incorporation permits quantitation of the number of protons transferred in the rate-limiting transition state

TABLE 5

Phosphorothioate and solvent deuterium isotope effects on AMP incorporation by PV $3D_{pol}$-catalyzed nucleotide incorporation in $Mg^{+2}$ and Mn + 2. Values are observed rate constants, AMP incorporation (in $s^{-1}$) at concentrations of ATP 6-fold greater than the $K_{D,app}$ for ATP.

| NTP/Solvent | pH 6.0 | pH 7.0 | pH 7.5 | pH 8.0 | pH 9.0 | pH 10.0 |
|---|---|---|---|---|---|---|
| Reactions in $Mg^{2+}$ | | | | | | |
| ATP | 6 ± 1 | 30 ± 3 | 30 ± 3 | 40 ± 4 | 50 ± 10 | 40 ± 4 |
| ATP-αS | 1 ± 0.2 | 10 ± 1 | 10 ± 1 | 20 ± 2 | 30 ± 3 | 40 ± 4 |
| Effect | 6 ± 2 | 3 ± 0.4 | 3 ± 0.4 | 2 ± 0.3 | 2 ± 0.4 | 1 ± 0.1 |
| $H_2O$ | 6 ± 1 | 30 ± 3 | 30 ± 4 | 40 ± 5 | 50 ± 10 | 40 ± 4 |
| $D_2O$ | 1 ± 0.2 | 6 ± 1 | 10 ± 1 | 20 ± 2 | 20 ± 3 | 20 ± 2 |
| Effect | 6 ± 2 | 5 ± 1 | 3 ± 0.5 | 2 ± 0.3 | 3 ± 0.6 | 2 ± 0.3 |
| Reactions in $Mn^{2+}$ | | | | | | |
| ATP | 0.7 ± 0.1 | 4 ± 1 | 10 ± 1 | 20 ± 2 | 50 ± 10 | |
| ATP-αS | 0.1 ± 0.05 | 0.6 ± 0.1 | 1.4 ± 0.3 | 3 ± 0.3 | 10 ± 2 | |
| Effect | 7 ± 4 | 7 ± 2 | 7 ± 2 | 7 ± 1 | 5 ± 1 | |

Solvent deuterium isotope effect as a probe for rate-limiting steps during nucleotide incorporation: Because it was difficult to interpret the loss of the thio effect in $Mg^{2+}$ at pH (proton inventory). In this experiment, the observed rate constant for nucleotide incorporation ($k_n$) is measured in reactions containing different mole fractions of $D_2O$ (n). A plot of the quotient $k_n/k_{H2O}$ ($k_{H2O}$ is the observed rate constant in H$_2$O) as a function of n will fall on the line defined by $k_{H2O}/k_{H2O}$ and $k_{H2O}/k_{H2O}$ if a single proton is transferred. The data will fit to a second-order polynomial if two protons are transferred, to a third order polynomial if three protons are transferred and so on. A proton-inventory experiment was performed for AMP incorporation by 3D$^{pol}$ in Mn$^{2+}$ (FIG. 4A) and in Mn$^{2+}$ (FIG. 4B). In neither case did the data fall on the line (dashed lines in FIGS. 4A, 4B) that would define a single proton transfer.

Figure 4A:
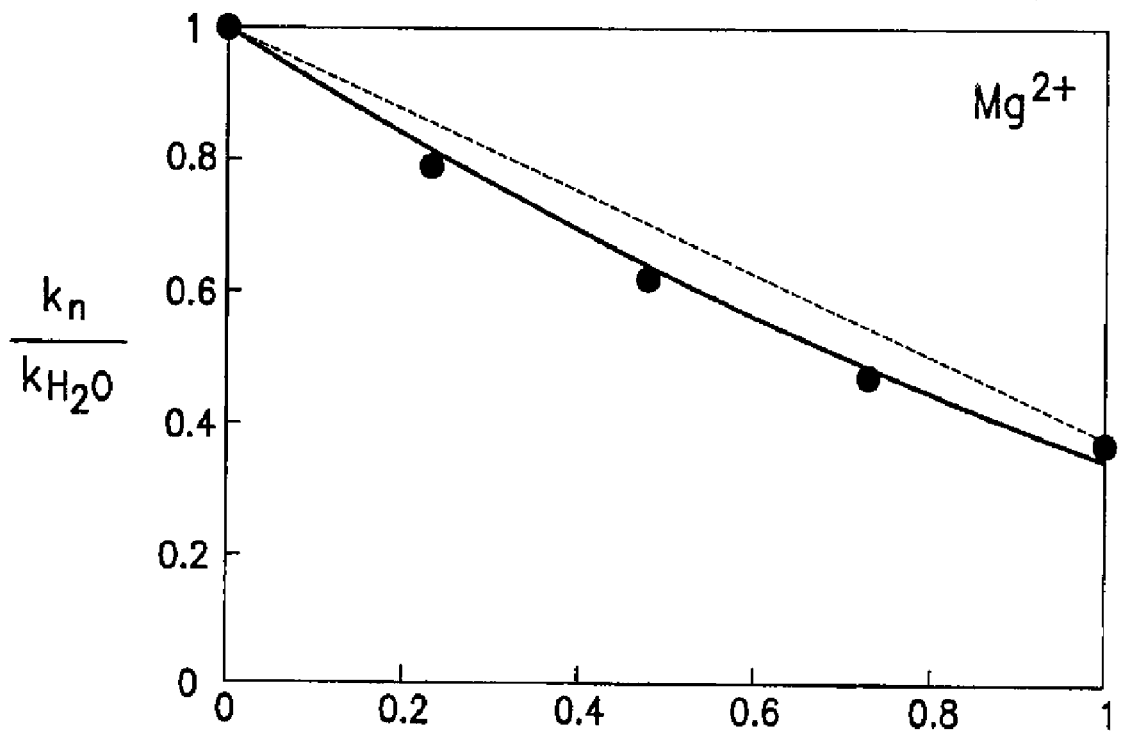
FIG. 4 is a pair of graphs showing that two protons are transferred during phosphoryl transfer. Proton inventory was performed in $Mg^{2+}$ (FIG. 4A) or $Mn^{2+}$ (FIG. 4B). $k_n$ is the observed rate constant for nucleotide incorporation at a particular mole fraction of $D_2O$. $k_{H2O}$ is the observed rate constant for nucleotide incorporation in $H_2O$. n is the mole fraction of $D_2O$. The solid line represents the fit of the data to a two-proton-transfer model (equation 5). The dashed line indicates the predicted line from a one-proton-transfer model (equation 6).
Figure 4B:
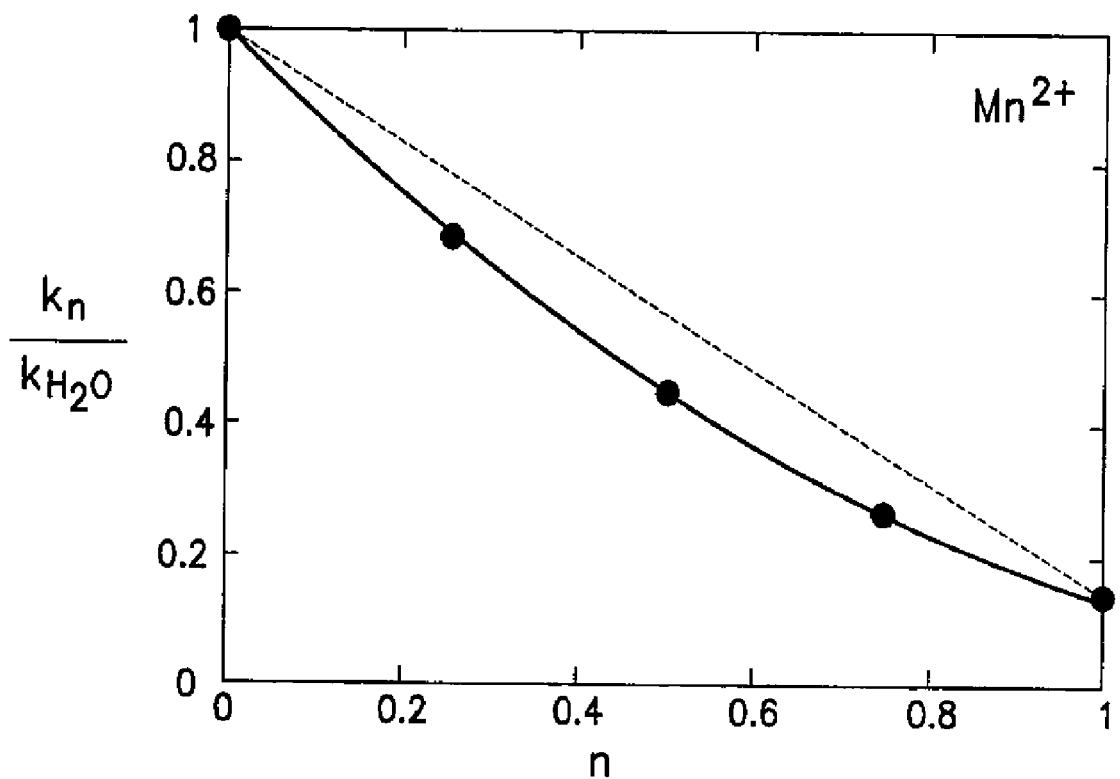

However, the data fit well to a second-order polynomial, the Gross-Butler equation (equation 5) for two-proton transfers (solid lines in FIGS. 4A, 4B). Based upon these data, we concluded that two proton transfer reactions occur in the rate-limiting transition state for phosphodiester bond formation catalyzed by the poliovirus RdRp.

Figure 5A:
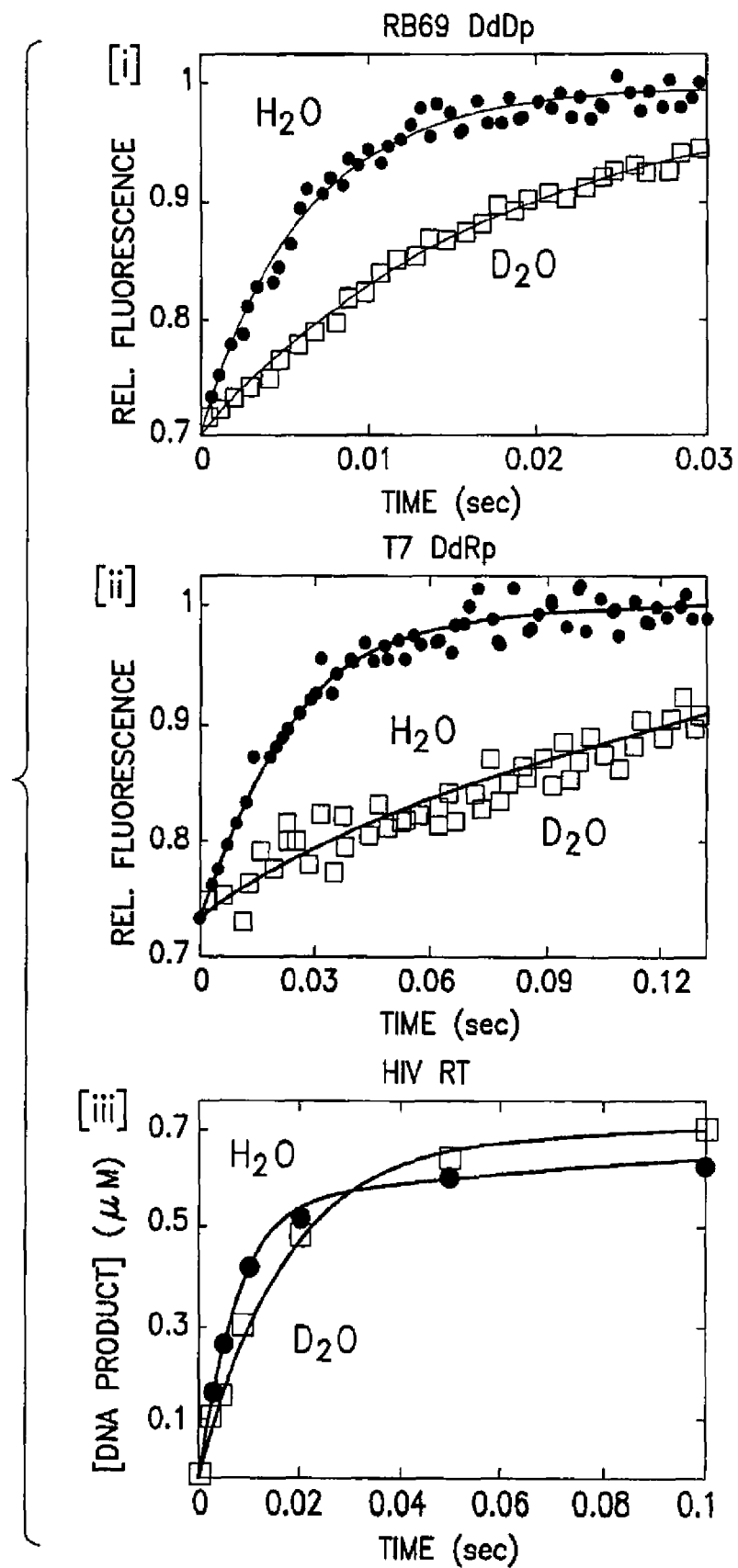
FIG. 5A shows the solvent deuterium isotope effect for other polymerases: [i] RB69 DdDp, [ii] T7 DdRp and [iii] HIV RT. Pre-steady-state rate constants for nucleotide incorporation were determined for all polymerases in $H_2O$ (●) or $D_2O$ (■). The solid lines are the fits of the data to equation 1. The rate constants were: 160±15 s$^{-1}$ and 60±6 s$^{-1}$ in $H_2O$ and $D_2O$, respectively, for RB69 DdDp; 46±5 s$^{-1}$ and 8±1 s$^{-1}$ in $H_2O$ and $D_2O$, respectively, for T7 DdRp; 140±14 s$^{-1}$ and 60±5 s$^{-1}$ in $H_2O$ and $D_2O$, respectively, for HIV RT.
Figure 5B:
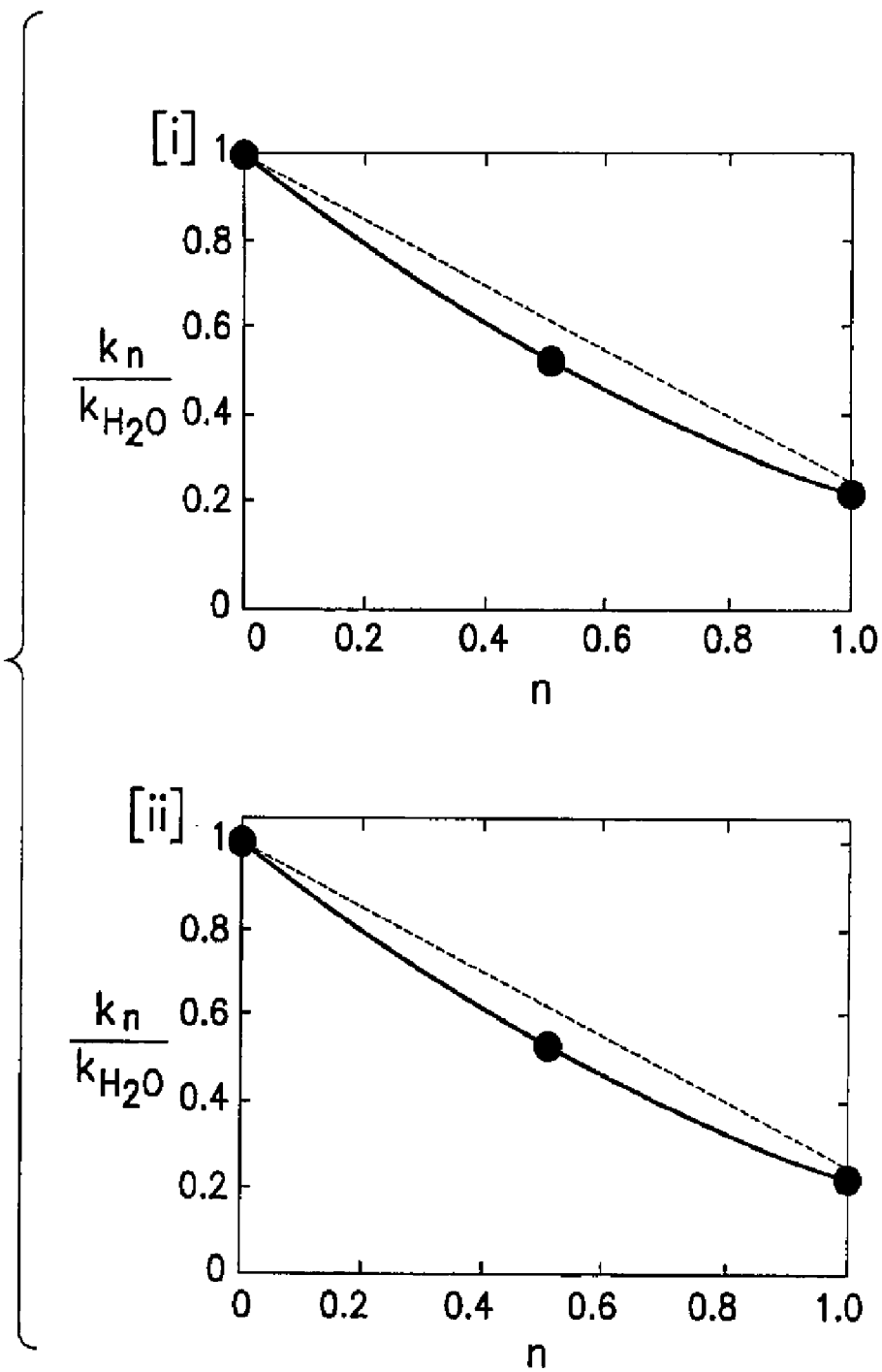
FIG. 5B shows the proton inventory for other polymerases: [i] RB69 DdDp, [ii] T7 DdRp and [iii] HIV RT. The solid lines are the fit of the data to a two-proton-transfer model (equation 5). The dashed line indicates the predicted line for a one-proton-transfer model (equation 6). In all cases, a two proton-transfer model fit the data best.

Two proton-transfer reactions in the rate-limiting transition state for nucleotidyl transfer of other classes of nucleic acid polymerases. In order to determine whether the conclusions reached here for the RdRp applied to other classes of nucleic acid polymerases, similar experiments were performed with RB69 DdDp, T7 DdRp and HIV RT. In all cases, a solvent deuterium isotope effect was observed (FIG. 5A, panels i-iii) that ranged from three to six (Table 1). Importantly, proton inventory experiments fit well to a two-proton model for these polymerases (FIG. 5B, panel i-iii and Table 2). It was concluded that two proton transfer reactions occur in the rate limiting transition state for nucleotidyl transfer catalyzed by all classes of nucleic acid polymerases.

Figure 7C:
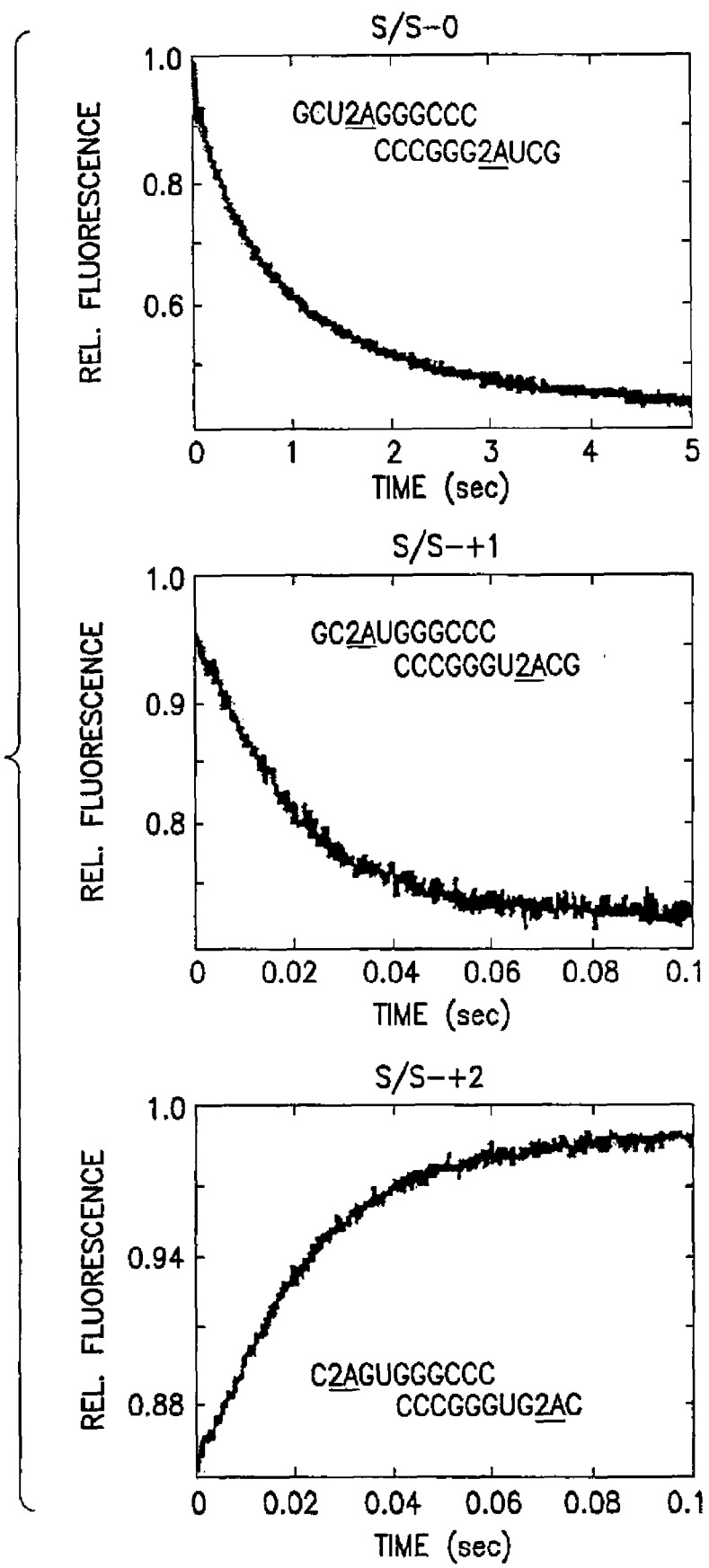
FIG. 7C is a series of graphs showing the magnitude and direction of the fluorescent transient depends on the location of 2A in the template. The actual sequences of the substrate employed for 2A at the S/S-0, S/S-+1 and S/S-+2 positions are indicated. Only the first "correct" nucleotide was evaluated: UTP (200 μM) for position 0 and ATP (200 μM) for positions +1 and +2. UMP incorporation into S/S-0 showed a 50% change in fluorescence and an observed rate constant, $k_{obs}$, of 1±0.1 s$^{-1}$. AMP incorporation into S/S-+1 showed a 25% change in fluorescence and a $k_{obs}$ of 60±8 s$^{-1}$. AMP incorporation into S/S-+2 showed a 15% change in fluorescence and a $k_{obs}$ of 50±6 s$^{-1}$. In the top graph. SEQ ID NO:13 in the 5' to 3' direction is hybridized to SEQ ID NO:13 shown in the 3' to 5' direction. In the middle graph, SEQ ID NO:14 in the 5' to 3' direction is hybridized to SEQ ID NO:14 shown in the 3' to 5' direction. In the bottom graph, SEQ ID NO:15 in the 5' to 3' direction is hybridized to SEQ ID NO:15 shown in the 3' to 5' direction.

3D$_{pol}$-catalyzed nucleotide incorporation can be monitored by using 2-aminopurine containing primer/template substrates. Previous studies of 3D$^{pol}$ mechanism revealed that the rate of nucleotide incorporation catalyzed by 3D$^{pol}$ is partially limited by both a conformational change and chemistry in the presence of Mg$^{2+}$. However, in the presence of Mn$^{2+}$, the reaction is limited solely by chemistry. The experiments leading to these conclusions employed radioactively labeled substrates and a chemical quench flow instrument (CQF). This approach is slow and provides no direct information on conformational changes that may occur during the reaction. 2-Aminopurine (2AP) has been employed to study DNA-dependent DNA and RNA polymerase-catalyzed reactions. 2AP is similar in structure to adenine, which has its amino group on the 6-position (FIG. 7A). 2AP can replace adenine in a nucleic acid duplex without significant alteration of the helical structure. We investigated the use of 2AP as a fluorescent probe for single-nucleotide addition when present at various positions in the templating strand of our class of primer-template substrates referred to as sym/sub (S/S) (FIG. 7B). Position 0 indicates that 2AP is the templating nucleotide (S/S-0). Position +1 indicates 2AP is one nt downstream of the templating nucleotide (S/S-+1), and position +2 indicates 2AP is two nts downstream of the templating nucleotide (S/S-+2). The magnitude and direction of the observed change in 2AP fluorescence (AF) was dependent on the position of 2AP relative to the templating nucleotide (FIG. 7C). Incorporation of UMP into S/S-0 (FIG. 7C) produced the largest AF and signal-to-noise ratio. However, this substrate has the undesirable feature that the incoming nucleotide is not templated by a "correct" base. In the case of 2AP, incorporation of UMP is slower than expected (1±0.1 $_{S-1}$), but on par with that observed in the chemical quench flow. As 2AP was moved downstream of the templating base, the AF and signal-to-noise ratio decreased, but the observed rate constants for incorporation (60±8 $_{S-1}$ and 50±6 $_{S-1}$ for S/S-+1 and S/S-+2, respectively) were as expected for AMP incorporation opposite UMP. The amplitude and signal-to-noise were better for 2AP in the +1 position than in the +2 position. All subsequent SF experiments utilized S/S-+1.

Validation of the SF assay. We previously determined the complete kinetic mechanism of 3D$^{pol}$-catalyzed nucleotide incorporation using radiolabeled S/S in the CQF. The values obtained in those experiments for $K_{D,app}$ and $k_{pol}$ were 130±20 µM and 90±10 s$^{-1}$, respectively. Use of S/S-+1 in CQF experiments produced values for $K_{D,app}$ and $k_{pol}$ of 70±10 µM and 80±10 $_{S-1}$, respectively (Table 3). We interpret the decrease in $K_{D,app}$ as a nearest neighbor effect caused by the 2AP. Note that the $k_{pol}$ values are the same—that is, within the error of the measurement.

Figure 8A:
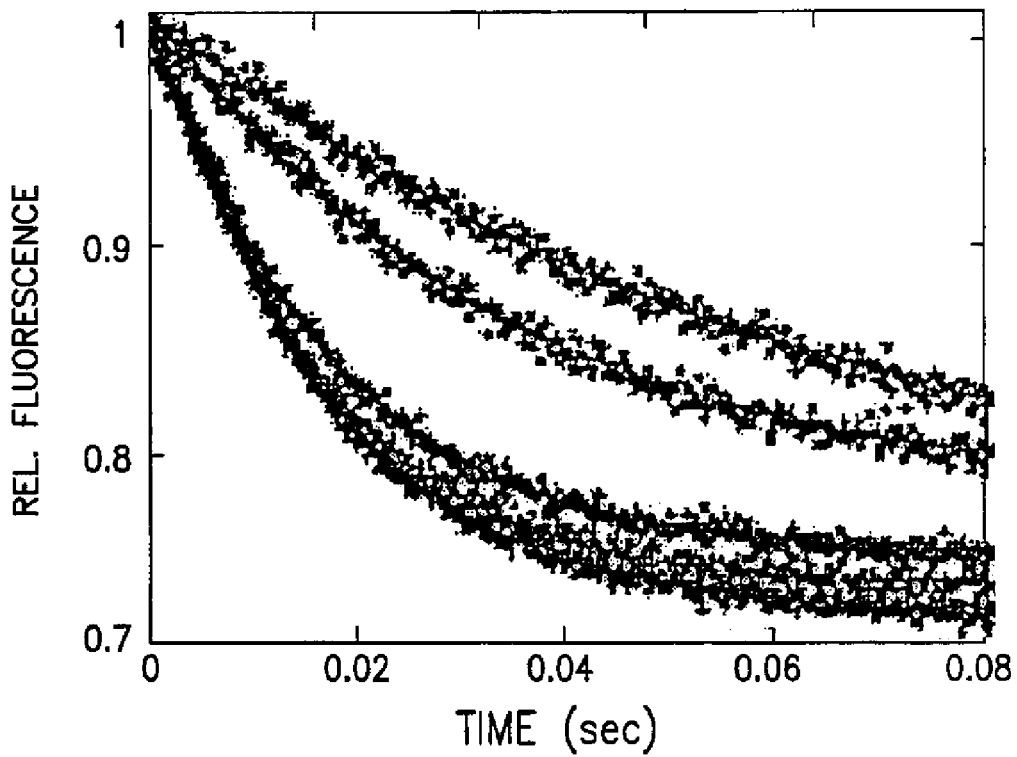
FIG. 8A shows the kinetics of AMP incorporation as a function of ATP concentration monitored by 2AP fluorescence. $3D^{pol}$ was incubated with S/S-+1 and mixed with 40-1200 μM ATP in a stopped-flow apparatus. The solid line represents the fit of the data to a single exponential equation (equation 1).
Figure 8B:
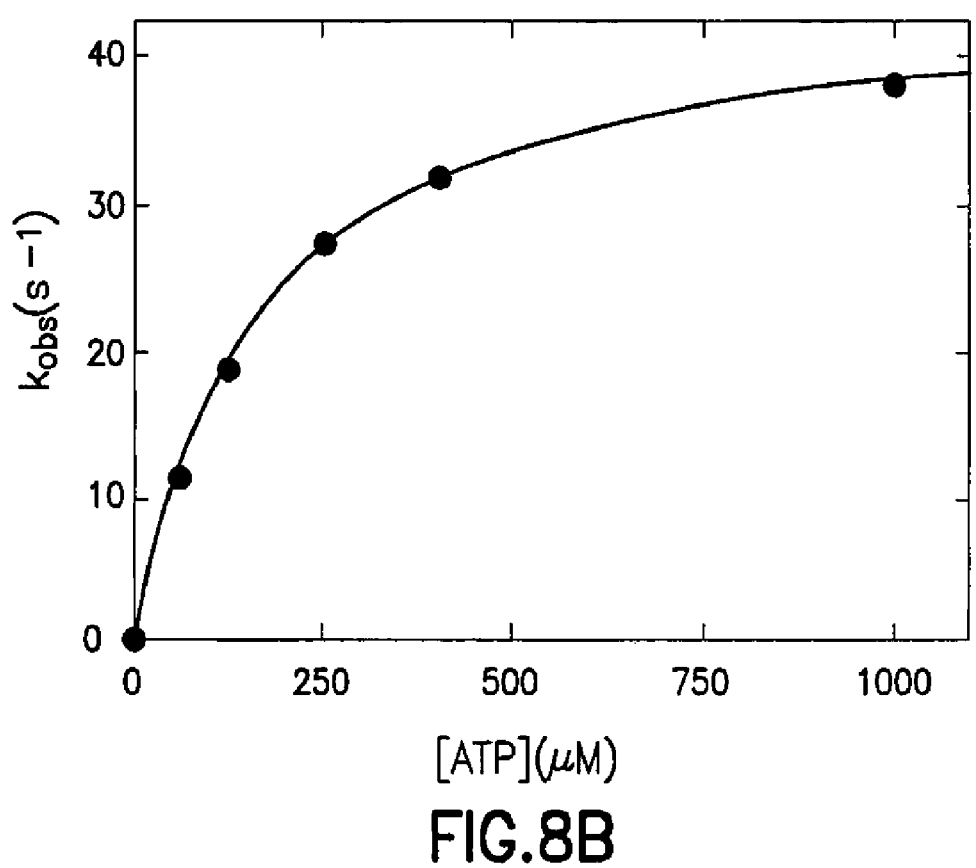
FIG. 8B shows the values obtained in FIG. 8A were plotted as a function of ATP concentration. The solid line represents the fit of the data to a hyperbolic equation (equation 2) yielding values for $K_{D,app}$ of 70±10 μM and $k_{pol}$ of 70±10 s$^{-1}$.

Experiments with S/S-+1 in the SF were performed with an excitation wavelength of 313 nm, ensuring excitation of only 2AP and guaranteeing that the observed changes in fluorescence were attributable only to changes in the environment surrounding the 2AP probe in the active site of 3Dpol. The observed change in fluorescence was measured as a function of ATP concentration (FIG. 8A). The observed rate constant, $k_{obs}$, at each ATP concentration was plotted as a function of ATP concentration and the data were fit to a hyperbola (equation 2), yielding values for $K_{D,app}$ and $k_{pol}$) of 70±10 µM and 70±10 s−1, respectively (FIG. 8B). It was concluded that the 2AP assay reports on product formation or some faster step thereafter.

Interrogation of the chemical mechanism for nucleotidyl transfer catalyzed by DNA polymerases has been thwarted by the general belief that a conformational change is rate limiting for nucleotide incorporation, a belief that has relied on interpreting the magnitude of the thio effect, a highly controversial parameter (Joyce, C. M. et al. (2004) *Biochemistry*. 43, 14317-24; Showalter, A. K. et al. (2002) *Biochemistry* 41, 10571-6). The studies described herein of the RdRp from poliovirus, however, have shown that chemistry is at least partially rate limiting for nucleotide incorporation in Mg$^{2+}$ and completely rate limiting in Mn$^{2+}$. This system permits interrogation of the chemical mechanism by employing a nucleotide incorporation assay.

Figure 1A:
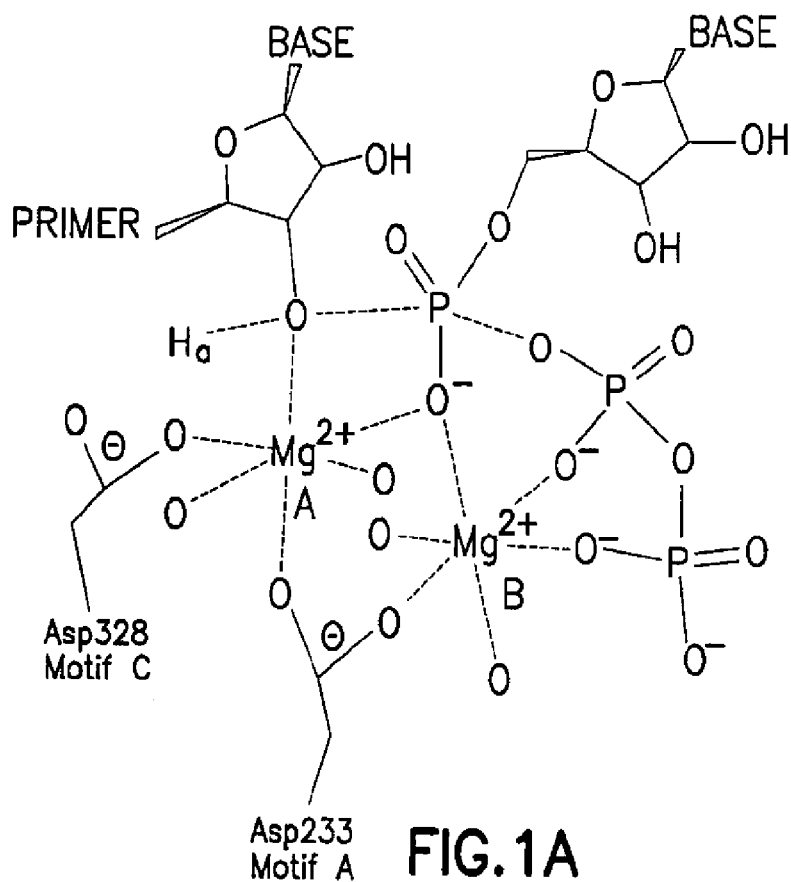
FIG. 1A depicts the two-metal-ion mechanism. The nucleoside triphosphate enters the active site with a divalent cation ($Mg^{2+}$, metal B). This metal is coordinated by the β- and γ-phosphates of the nucleotide, by an Asp residue located in structural motif A of all polymerases, the 3Dpol residue is indicated, and likely water molecules (indicated as oxygen ligands to metal without specific designation). This metal orients the triphosphate in the active site and may contribute to charge neutralization during catalysis. Once the nucleotide is in place, the second divalent cation binds ($Mg^{2+}$, metal A). Metal A is coordinated by the 3'-OH, the α-phosphate, as well as Asp residues of structural motifs A and C. This metal lowers the pKa of the 3'-OH (denoted as $H_a$) facilitating catalysis at physiological pH.
Figure 1B:
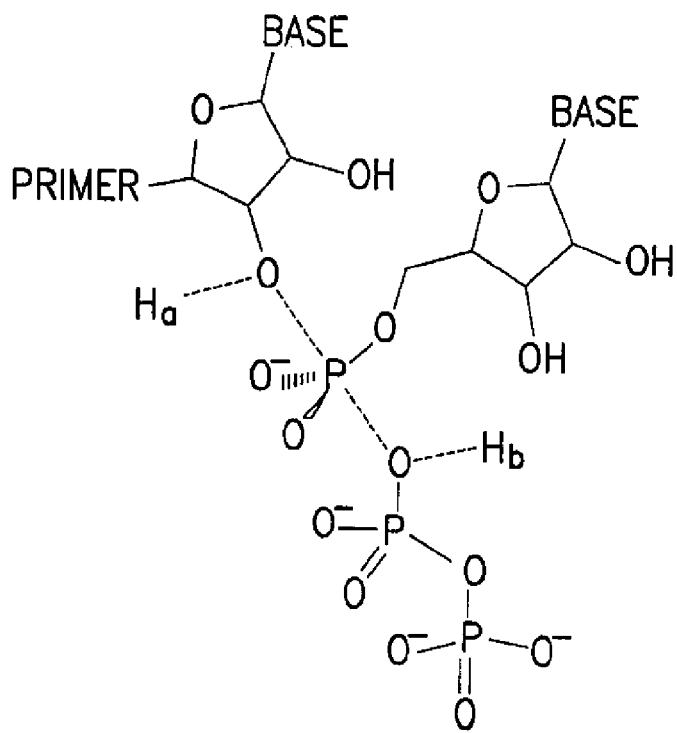
FIG. 1B shows the proton transfer reactions. During the phosphoryl transfer reaction, two proton transfer reactions may occur. The proton from the 3'-OH nucleophile ($H_a$) must be removed; a proton may be donated to the pyrophosphate leaving group ($H_b$).
Figure 2A:
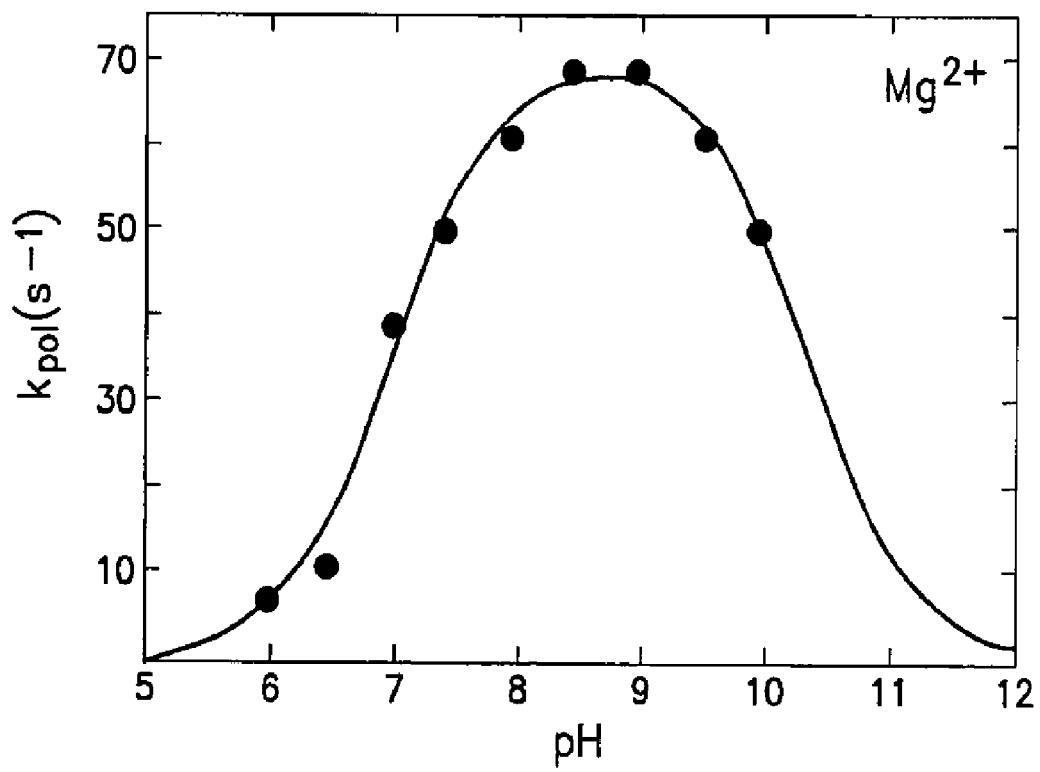
FIG. 2 is a pair of graphs showing two ionizable groups are required for phosphoryl transfer. Values for $k_{pol}$ were obtained for AMP incorporation into S/S-+1 using the stopped-flow assay in $Mg^{+2}$ (FIG. 2A) or $Mn^{+2}$ (FIG. 2B). pH values greater than 10 in $Mg^{+2}$ and in $Mn^{+2}$ caused precipitation of nucleotide. The solid lines show the fit of the data to equation 3 for $Mg^{+2}$, yielding pKa values of 7.0±0.1 and 10.5=0.1 and to equation 4 for $Mn^{+2}$, yielding a pKa value of 8.2±0.1. The dashed line in FIG. 2B shows the predicted curve should yield an ionizable group with a $pK_a$ of 10.5 exist in $Mn^{+2}$.
Figure 2B:
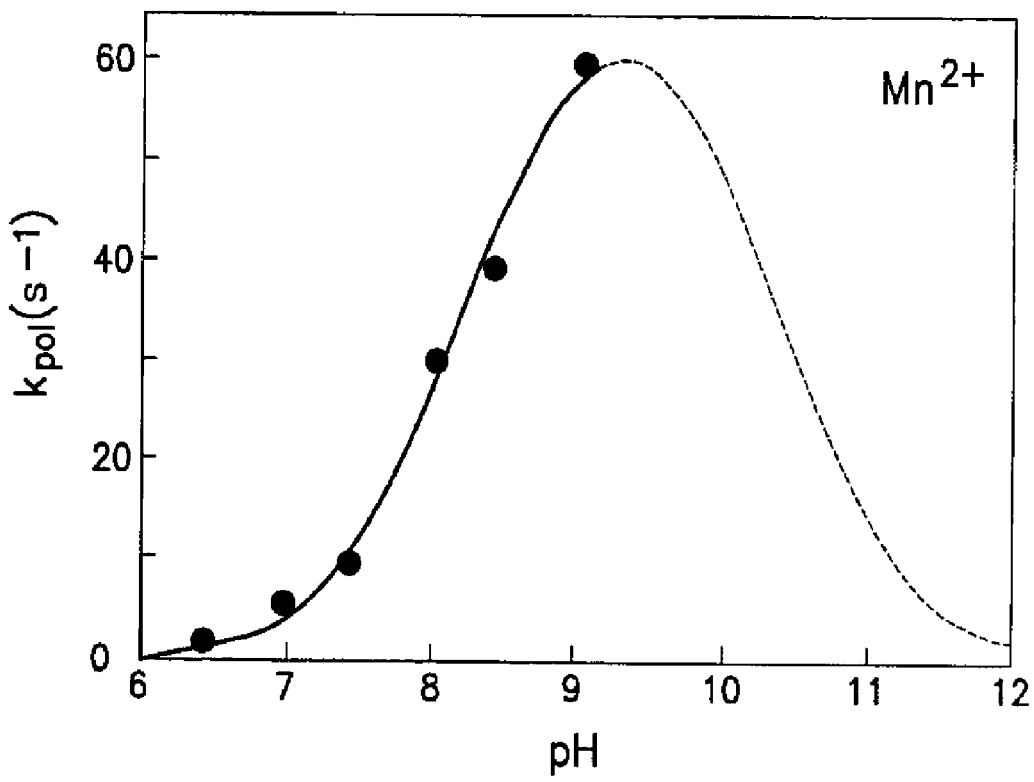

Evaluation of the pH dependence of PV polymerase-catalyzed nucleotide incorporation in Mg$^{2+}$ revealed a dependence of the reaction on two ionizable groups with pKa values of 7.0 and 10.5 (FIG. 2A). The pKa value of 7.0 was assigned to the 3'-OH because protonation of this group reduces the efficiency of nucleotide incorporation and chemistry is clearly rate limiting below pH 7.5 (Table 5). The pKa value of 10.5 was assigned to a residue on the enzyme that serves to protonate the PP$_i$ leaving group because deprotonation of this group reduces the efficiency of nucleotide incorporation and the extent to which chemistry is rate limiting in the pH range from 7.5 to 10.5 is the same (Table 5).

The observed pKa value for the 3'-OH is sensitive to the disposition of residues in the active site as distortions caused by increasing the size of the divalent cation or substituting ATPαS for ATP cause an increase in the observed pKa value (FIG. 2B and Table 5). The observed reduction in the nucleophilicity of the 3'-OH when ATPαS is employed provides an explanation for the observed reduction in the thio effect at pH values above 7.5. This observation calls into question the validity of the thio effect in polymerase systems. In order for the magnitude of the thio effect to yield information on rate-limiting steps during the nucleotide-addition cycle, the observed reduction in the rate constant for AMPαS incorporation relative to AMP incorporation should be attributable solely to the reduced electrophilicity of the α-phosphorous caused by the sulfur substitution. Extrapolating the RdRp data to other polymerase systems, the observed rate constant for AMP incorporation should not be compared directly to the observed rate constant for AMPαS incorporation at the same pH value.

The solvent deuterium isotope effect is a useful probe for chemistry in the rate limiting step for nucleotide incorporation by the RdRp (FIG. 3 and Table 5). The observed values for the solvent deuterium isotope effect ranged from two in $Mg^{2+}$ at pH 7.5 (FIG. 3A) where chemistry is only partially rate limiting (1) to seven in $Mn^{2+}$ at pH 7.5 (FIG. 3B) where chemistry is completely rate limiting. No significant isotope effect was measured in the steady state in the presence of either divalent cation (FIGS. 3C and 3D), consistent with the rate constant for polymerase dissociation being measured under these conditions. Application of the solvent deuterium isotope effect to other polymerase systems (FIG. 5A) revealed chemistry as partially rate limiting for nucleotide incorporation catalyzed by RB69 DdDp, T7 DdRp and HIV RT and validated the solvent deuterium isotope effect as a useful mechanistic probe of rate-limiting steps for all polymerases (Table 2).

The observation of a solvent deuterium isotope effect permitted the quantification of the number of proton-transfer reactions occurring during the rate-limiting transition state for nucleotide incorporation catalyzed by the RdRp (FIG. 4) and other polymerases as well (FIG. 5B). In all cases, two proton-transfer reactions were observed (Table 2). This observation would suggest that conversion of the 3'-OH to the 3'-O— does not occur as a discrete step prior to attack of the α-phosphorous of the bound nucleotide and provides the first evidence that the $PP_i$ leaving group does indeed leave protonated.

A solvent deuterium isotope effect of seven was observed for the RdRp under conditions in which chemistry is the sole rate-limiting step for nucleotide incorporation (FIG. 3), consistent with both protons being transferred simultaneously in the rate-limiting transition state. Efficient proton transfer would necessitate a suitable proton acceptor and donor. As discussed above, structural studies have not identified water molecules to serve this function. Moreover, the pKa values of 7.0 and 10.5 (FIG. 2) observed here for PV polymerase-catalyzed nucleotidyl transfer are also inconsistent with water serving as the proton acceptor or donor. The data described herein suggest that a general base and a general acid are employed in nucleotidyl-transfer reactions catalyzed by all polymerases (FIG. 6). There is a general consensus that the structural homologue of polβ Asp-256 in other systems is the evolutionarily conserved Asp residue of motif C (Table 6). In many polymerase structures, this motif C residue is often found serving as a ligand for one or both metals. This circumstance permits distance arguments to be used against this residue serving as a general base. However, in structures of a *Bacillus stearothermophilus* DNA polymerase I fragment (BF) undergoing catalysis, this motif C residue interacts with the primer 3'-OH after nucleotide binding but prior to binding of the second metal ion (metal A). In addition, computational modeling of the nucleotidyl transfer reaction catalyzed by the T7 DdDp has suggested that the conserved motif C residue, Asp-654, serves as a general base.

It is generally assumed that the $pK_a$ value for the $Mg^{2+}$-bound $PP_i$ is low enough to preclude protonation during catalysis. However, in solution the highest $pK_a$ value for $PP_i$ is on the order of 9.3. Therefore, protonation of $PP_i$ by a general acid should increase the rate of catalysis but may not be absolutely essential. Structural studies have revealed a basic amino acid, in most cases a lysine, in a position to serve as a general acid (Table 6). This residue is located on helix O of A-family polymerases, helix P of B-family polymerases and on the loop of structural motif D of RdRps and RTs. Motif D has been in search of a function other than structural scaffolding since solution of the first RT structures. In all cases in which this putative general acid has been changed, the observed rate constant for nucleotide incorporation has been diminished substantially. Particularly noteworthy is the observation that chemistry appears to become the rate-limiting step by changing the putative general acid of RB69 DNA polymerase, Lys-560, to alanine.

The RdRp from PV was used as a model in the studies described herein to produce the first comprehensive analysis of the chemical mechanism for a nucleic acid polymerase. This system has proven to be particularly attractive because of the extremely slow (0.0001 $s^{-1}$) and pH-independent nature of the rate constant for dissociation of the primer-template substrate from the enzyme. These studies have provided very compelling evidence for a highly symmetrical transition state with proton transfers from the 3'-OH and to $PP_i$ occurring coordinately. Pyrophosphate protonation was not expected. All classes of polymerase appear to have a similar transition-state structure. Coordinated proton transfer reactions necessitate a well-positioned acceptor and donor. The observed pKa values required for nucleotidyl transfer and the absence of ordered water molecules in the appropriate position in all cases force one to re-propose general-acid-base-facilitated catalysis by all polymerases.

TABLE 6

Putative general acid and general base residues for nucleic acid polymerases

| Enzyme | DNA Pol Family | PDB accession number | Motif A | Motif C[a] (general base) | Putative general acid |
|---|---|---|---|---|---|
| T7 DdDP | A | 1t7p | D475 | D654, E655 | K522 |
| E. coli DNA Pol I DdDP (KF) | A | | D705 | D882, E883 | K578 |
| Bacillus stear. DNA Pol I DdDP (BF) | A | 4bdp | D653 | D830, E831 | K706 |
| Therm. aquat. DNA Pol I DdDP (Klentaq) | A | 3ktq | D610 | D785, E786 | K663 |
| RB69 DdDP | B | 1ig9 | D411 | D621, D623 | K560 |
| Human Pol β DdDP | X | 2fms | D190, D192 | D256 | R183 |
| HIV-1 RT RdDP | RT | 1rtd | D110 | D185, D186 | K220 |
| T7 DdRP | — | 1mws | D537 | D812 | K631 |
| PV 3D Pol RdRP | — | 1ra7 | D233 | D328, D329 | K359 |

[a]Putative general base indicated in bold-faced type.

Example 2

General Acid Catalysis is Important in the Phosphoryl Transfer Reaction of Nucleic Acid Polymerases The experiments described herein show that poliovirus RNA-dependent RNA polymerase (3Dpol) active site Lys-359 enhances the rate of phosphoryl transfer by acting as a catalytic general acid. This finding was extended to conserved active site lysine residues in polymerases from other classes by the demonstration of a role as catalytic general acid for the conserved active site lysine of HIV-1 RT RdDp and RB69 DdDp. General acid catalysis by a conserved active site residue capable of proton donation may therefore be a universal feature of the nucleic acid polymerase phosphoryl transfer reaction, adding an additional 2-3 orders of magnitude of rate enhancement to that already supplied by the two metal cations, and bringing rates of nucleotide incorporation to a level of biological sufficiency.

Nucleic acid polymerases are the primary agents of genome replication, maintenance and expression in all organisms and viruses. To fulfill this role, these enzymes must not only assemble nucleic acid chains at biologically sufficient rates but must also achieve a level of accuracy of nucleotide selection (fidelity) that is optimal for fitness.

Nucleic acid polymerases vary widely in their nucleic acid tasks. They require DNA or RNA as template. In most situations, they add nucleotides to a DNA, RNA or peptide primer-terminus 3'-OH. However, in some cases a primer-terminus requirement is lacking and nucleotide addition occurs de novo. Polymerase fidelity likewise varies widely. Misincorporation frequencies range from as low as $10^{-8}$ errors per incorporation in some genome-replicating DNA polymerases, to $10^{-5}$ for certain viral RNA polymerases to $10^{-2}$ or higher for some repair enzymes. In all cases, misincorporation rates are thought to reflect biological need. Enzyme size and architectural complexity also vary widely, ranging from small, single-subunit enzymes having only polymerase activity to large, multi-subunit macromolecule assemblages possessing additional activities.

The broad range in biological roles, incorporation accuracies and overall architecture thus impose multiple functional constraints on the polymerase nucleotide incorporation mechanism. Yet in spite of this complexity, the most basic underlying polymerase active site structural features are highly conserved. In addition, all nucleic acid polymerases accomplish the same fundamental chemical reaction of phosphoryl transfer and use essentially the same five-step mechanism in the single nucleotide incorporation cycle. In step one an incoming nucleotide binds to the enzyme-primer/template binary complex. In step two this ternary complex undergoes a conformational change, aligning reactive functional groups for phosphoryl transfer, which occurs in step three. A post-chemistry conformational change occurs in step four. Pyrophosphate release occurs in step five, resetting the cycle to start the next incorporation.

Polymerase amino acid sequence alignments in combination with a growing list of high-resolution x-ray crystal structures of polymerase-primer/template-nucleotide ternary complexes reveal the universal presence of an active site positively charged amino acid residue, usually Lys but sometimes Arg or His, in the precise location of covalent bond cleavage and leaving group formation during step three, phosphoryl transfer, of the nucleotide incorporation cycle. Conservation of a residue capable of proton donation at this specific location suggests a direct role as general acid catalyst during phosphoryl transfer for this active site amino acid. However, a long-standing experimental limitation of some well-studied nucleic acid polymerase model systems has been the inability to interrogate the phosphoryl transfer step directly and conveniently because of a rate-limiting conformational change immediately prior to chemistry. This limitation was removed with findings described herein that for PV polymerase (3Dpol), an RNA-dependent RNA polymerase (RdRp), phosphoryl transfer is partially or completely rate-limiting in $Mg^{2+}$ or $Mn^{2+}$, respectively, and therefore accessible to mechanistic examination.

One proton transfer during the chemistry step of nucleotide incorporation is the removal of the proton from the primer-terminus 3'-OH (and acceptance by an undetermined recipient) during creation of the attacking nucleophile. As described above, universal conservation of a positively charged amino acid residue capable of proton donation at the precise site of bond cleavage and pyrophosphate leaving group formation during phosphoryl transfer suggests that the second catalytically-important proton transfer may involve this active site amino acid residue in a role as general acid catalyst.

Materials and Methods

Materials: Materials were purchased and prepared as described in Example 1.

Expression and purification of polymerases: 3Dpol RdRp, HIV-1 RT, RB69 DdDp and T7 DdRp were expressed in *E. coli* and purified as described previously (Castro et al, Proc. Natl. Acad. Sci., 104:4267-4272, 2007) except for the following. Construction of the RB69 DdDp K560L mutant—The K560L mutant was constructed using the pSP72-RB69-pol template and introducing the K560L-encoding mutation into the polymerase gene (gp43) by Quick Change PCR using the forward oligonucleotide RB69-DdDp-K560L-fwd 5'-GCA-CAAATTAATCGTCTGTTGCTTATCAACTCAC-3' (SEQ ID NO:7) and reverse oligonucleotide RB69-DdDp-K560L-rev 5'-GTGAGTTGATAAGCAACAGACGAT-TAATTTGTGC-3' (SEQ ID NO:8). The expression vector for RB69 K560A was kindly provided by Dr. William Konigsberg, Yale University.

PV 3D$^{pol}$-catalyzed nucleotide incorporation experiments: PV 3Dpol stopped-flow and chemical-quench-flow experiments were accomplished as described previously (Castro et al, Proc. Natl. Acad. Sci., 104:4267-4272, 2007). Enzymes, substrates and buffers for proton-inventory experiments were prepared in 100% water or 100% $D_2O$ followed by mixing at the appropriate ratio to obtain 0, 25, 50, 75 or 100% $D_2O$. Deuterated glycerol was used in all solutions in $D_2O$. All data collection was performed in the stopped-flow instrument. The pD was used instead of pH for the solutions in $D_2O$ as described above.

Solvent deuterium isotope effect and proton inventory for WT and a K220A HIV-RT were performed essentially as described in Example 1.

RB69 WT DdDp stopped-flow and chemical-quench-flow experiments: RB69 DdDp WT solvent deuterium isotope effect and proton inventory chemical-quench-flow experiments were done essentially as described in Example 1, with reactions quenched in 1 M HCl, neutralized and analyzed as described in Example 1.

Stopped-flow $K_{d,app}$ and $k_{pol}$, solvent deuterium isotope effect and proton inventories for RB69 K560A: Experiments were done using reaction conditions and DNA primer and template essentially as described for WT (Castro et al, Proc. Natl. Acad. Sci., 104:4267-4272, 2007). For $K_{d,app}$ and $k_{pol}$ determinations, $k_{obs}$ was obtained using [dATP] of 0.5, 1, 2.5, 5 and 10 mM. For 2.5 and 10 mM dATP reactions, $MgSO_4$ was supplemented to maintain free $Mg^{2+}$ at 10 mM. Plots of $k_{obs}$ vs. [dATP] were fit with a hyperbola (eq. 2). Solvent deuterium isotope effect and proton inventory experiments were conducted as for WT except [dATP] was 10 mM and $MgSO_4$ was increased to provide 10 mM free $Mg^{2+}$ over that bound to dATP. Chemical-quench-flow solvent deuterium isotope effect for RB69 K560A—Experiments were done as described above in the stopped-flow except [dATP] was 5 mM. Reactions were quenched with 0.25 M EDTA as described in Example 1.

Chemical-quench-flow $K_{d,app}$, $k_{pol}$, solvent deuterium isotope effect and proton inventories for RB69 K560L: Experiments were done using reaction conditions and DNA primer and template essentially as described for WT (Castro et al, Proc. Natl. Acad. Sci., 104:4267-4272, 2007). For $K_{d,app}$ and $k_{pol}$ determinations, $k_{obs}$ was obtained using [dATP] of 0.3, 1, 3, 6 and 12 mM. For 3, 6 and 12 mM dATP reactions, MgSO$_4$ was supplemented to maintain free Mg$^{2+}$ at 10 mM. Plots of $k_{obs}$ vs. [dATP] were fit with a hyperbola (eq. 2). Solvent deuterium isotope effect and proton inventory experiments were conducted as for WT except [dATP] was 5 mM and MgSO$_4$ was increased to provide 10 mM free Mg$^{2+}$ over that bound to dATP. Chemical-quench-flow RB69 K560L reactions were quenched with 0.25 mM EDTA as described in Example 1.

Data analysis: Data analysis was performed as described in Example 1.

Results

Figure 11C:
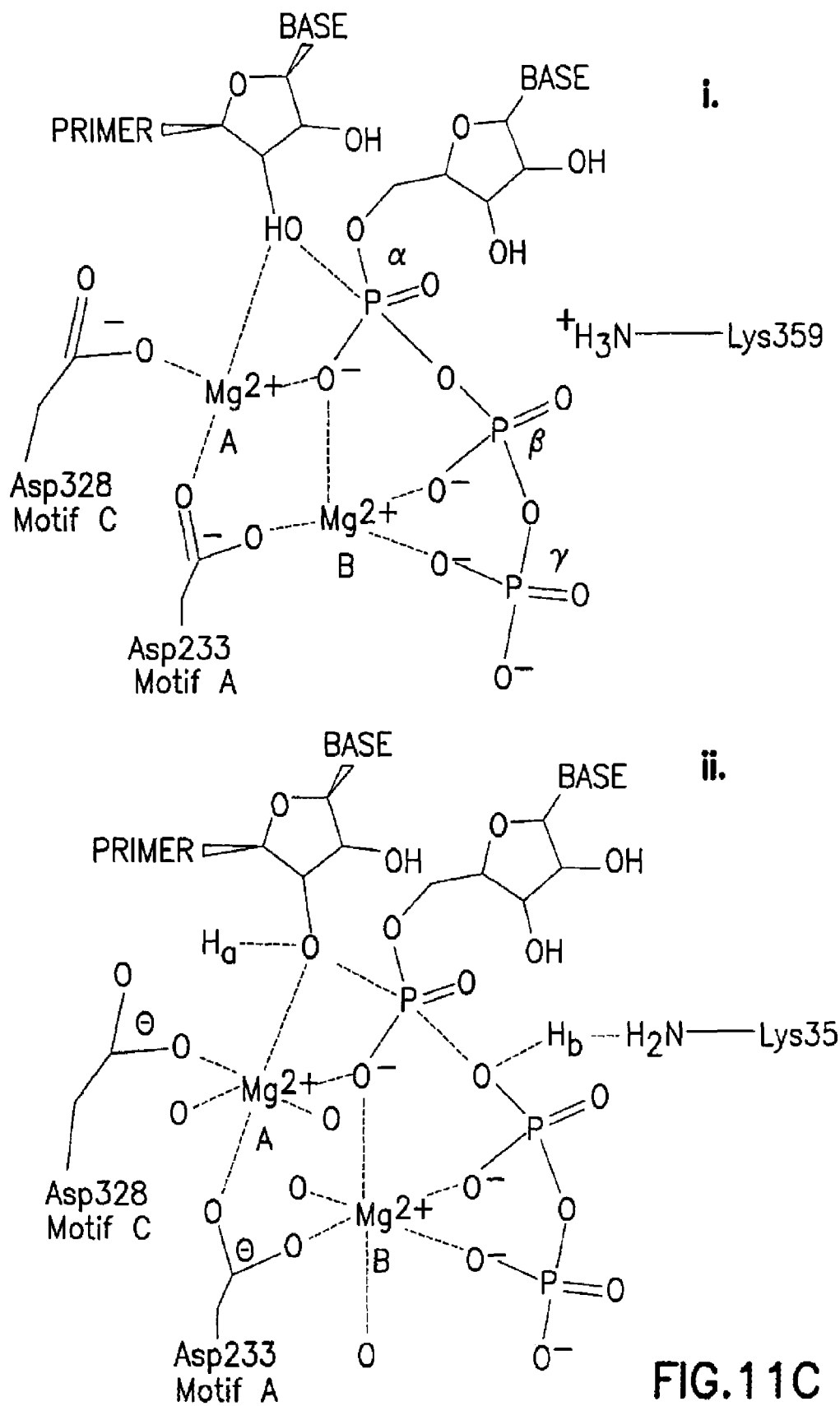
FIG. 11C: Lys-359 is positioned to function as a general acid catalyst during phosphoryl transfer.

The conserved active site positively charged amino acid residue in PV 3Dpol is Lys-359: Nucleic acid polymerase architecture resembles a cupped right hand consisting of palm, thumb and fingers subdomains. Conserved structural motifs comprise the palm subdomain, the location of the polymerase active site. Alignment of RNA polymerase palm structural motif D amino acid residues shows absolute conservation of a lysine residue (FIG. 11A). In PV 3Dpol, this conserved active site residue is Lys-359 (FIG. 11A). Molecular modeling based on PV 3Dpol crystal structures suggest that 3Dpol Lys-359 interacts intimately with the triphosphate moiety of the bound nucleotide at a site between the α- and β-phosphorus atoms (FIGS. 11B and 11Ci). Experimental data summarized below indicate that the PV 3Dpol Lys-359 serves as a general acid catalyst during the phosphoryl transfer step of nucleotide incorporation by donating its dissociable proton at the site of bond cleavage to the pyrophosphate leaving group (FIG. 11Cii).

Kinetic parameters for 3Dpol position-359 mutants suggest a catalytic role for Lys-359: To evaluate the influence of PV 3Dpol Lys-359 on the phosphoryl transfer step, this residue was changed to Leu, H is or Arg (Table 7). K359L 3Dpol with Mg$^{2+}$ as metal-ion co-factor showed a 50-fold reduction in single nucleotide incorporation catalytic rate ($k_{pol}$) relative to WT K359 and a 3-fold weakening in nucleotide binding, as reported by $K_{d,app}$. These data suggest a profound role for Lys-359 in catalysis and a lesser role in nucleotide binding. The reduced catalytic performance of K359L 3Dpol is consistent with lack of ability to donate a proton by the chemically inert Leu side chain. The reduction, albeit small, in nucleotide binding is consistent with absence of a positive charge on the Leu side chain, presumably important for binding interactions with the negatively-charged nucleotide triphosphate moiety.

TABLE 7

Summary of poliovirus 3Dpol RdRp kinetic parameters

| Enzyme P | Metal co-factor | $K_{d, app}$ (μM)[a] | $k_{pol}$ (s$^{-1}$) | SDKIE[b] |
|---|---|---|---|---|
| WT Lys 359 | Mg$^{2+}$ | 200 ± 20 | 50 ± 5 | 3 ± 1 |
| WT Lys 359 | Mn$^{2+}$ | 5 ± 1 | 10 ± 1 | 7 ± 1 |
| K359L | Mg$^{2+}$ | 700 ± 80 | 1 ± 0.1 | 2 ± 1 |
| K359L | Mn$^{2+}$ | 2 ± 0.1 | 1 ± 0.1 | 3 ± 1 |
| K359H | Mg$^{2+}$ | 339 ± 12 | 5 ± 0.1 | nd[c] |
| K359R | Mg$^{2+}$ | 139 ± 1 | 5 ± 0.1 | nd |

[a]$K_{d, app}$ is for ATP.
[b]SDKIE is solvent deuterium kinetic isotope effect, calculated as $k_{obs}$ in H$_2$O/$k_{obs}$ in D$_2$O at saturating [ATP].
[c]nd means not determined.

The solvent deuterium kinetic isotope effect (SDKIE) for WT K359 3Dpol was 2-fold larger in the presence of Mn$^{2+}$ than in Mg$^{2+}$, consistent with chemistry being completely rate-limiting in Mn$^{2+}$ and partially rate-limiting in Mg$^{2+}$. In contrast, identical and low $k_{pol}$ values and indistinguishable SDKIE values in Mg$^{2+}$ and Mn$^{2+}$ for K359L 3Dpol point to the importance of Lys-359 in catalysis and indicate that chemistry is completely rate-limiting with either metal ion co-factor for this mutant enzyme (Table 7).

Catalytic rates for the K359H and K359L 3Dpol variants were 5-fold faster than for K359L 3Dpol, but 10-fold slower than the WT K359 polymerase (Table 7). Nucleotide binding interactions for the K359H and K359L enzymes were similar to that of WT, consistent with retention of ability of the positively charged His and Arg side chains to bind a negatively-charged incoming nucleotide. However, while both His and Arg have exchangeable protons theoretically available to assist catalysis, their 10-fold diminished catalytic rates relative to the WT K359 enzyme suggests that the active site environment during phosphoryl transfer is not chemically (i.e. matching of pKas, etc.) and/or spatially optimized to make efficient catalytic use of these non-biological residues when at position 359.

Figure 12A:
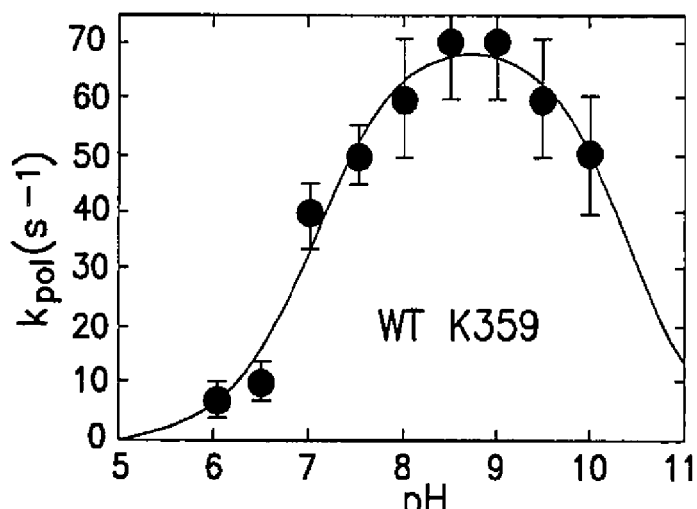
FIG. 12A: pH-rate profile for WT K359 3Dpol shows that two ionizable groups influence the rate of phosphoryl transfer. Estimated pKas of the two groups are 7.0, believed to correspond to the 3'-OH proton, and 10.5, hypothesized to correspond to the Lys-359 proton.
Figure 12B:
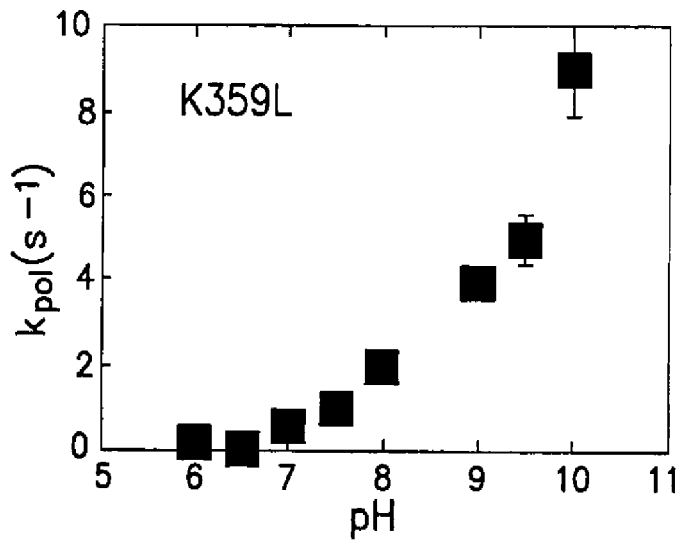
FIG. 12B: The basic arm of the pH-rate profile is lost in the 3Dpol K359L enzyme, indicating loss of one chemistry-influencing ionizable group.
Figure 12C:
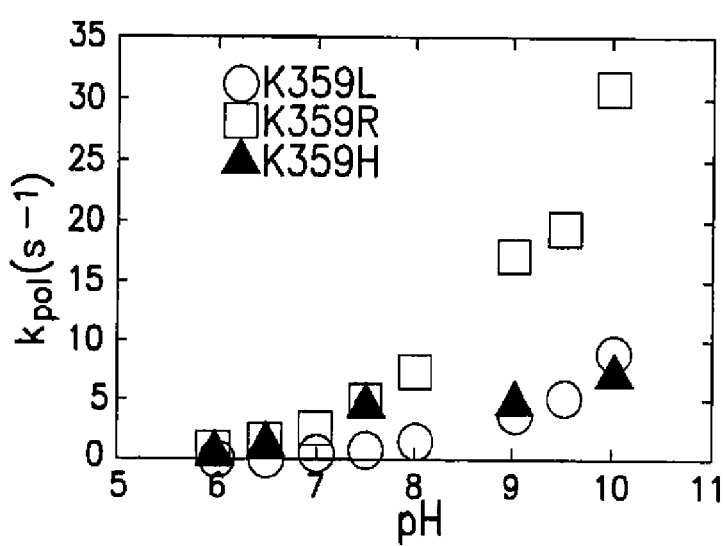
FIG. 12C: pH-rate profiles of K359H and K359R 3Dpols are superimposed over that for the K359L enzyme. The K359H polymerase is 5-fold kinetically superior to K359L at pH 7.5, approximately the pKa of the His imidazole group dissociable proton, but then converges toward K359L kinetic performance at higher pHs. The K359R polymerase is 5-fold kinetically superior to K359L at pH 7.5 but at higher pHs, as the pKa of the Arg side chain is approached, the catalytic ability of K359R approaches that of the WT K359 3Dpol.
Figure 13:
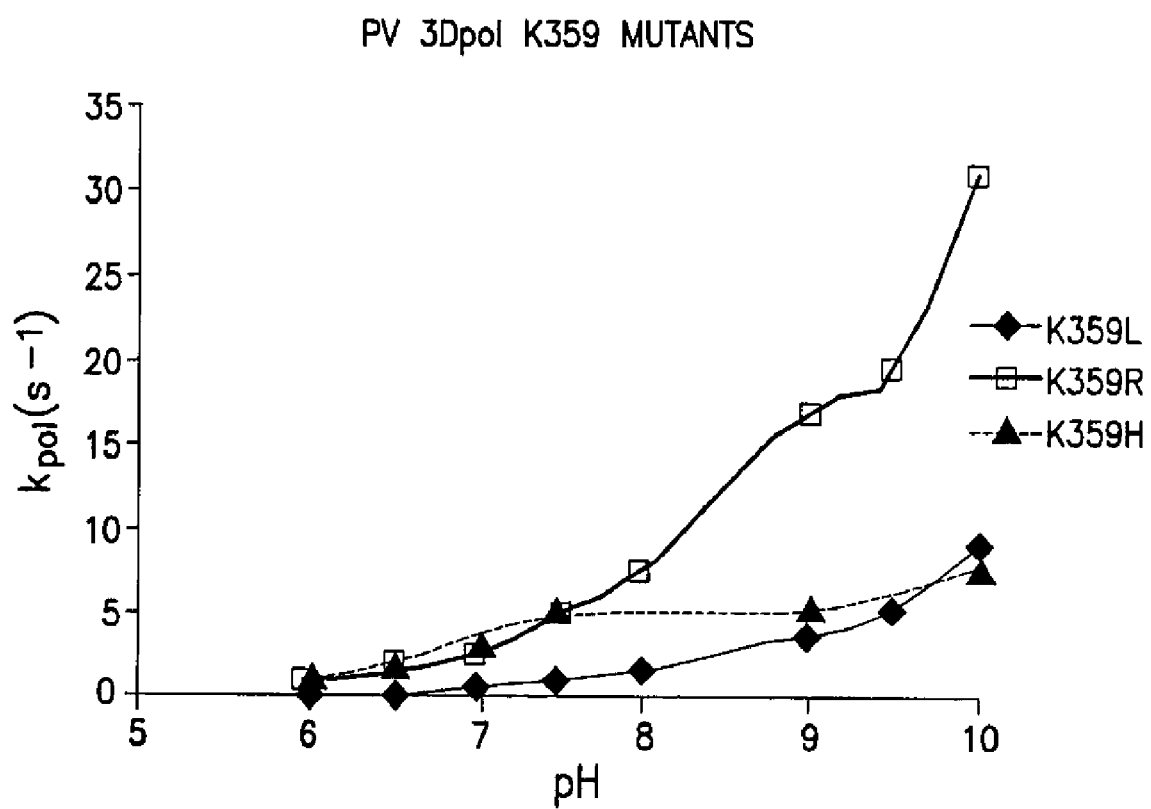
FIG. 13 is an enlarged version of the graph shown in FIG. 12C.

As shown in FIG. 12B, the basic arm of the pH-rate profile for the K359L enzyme has been lost, leaving only one ionizable group influencing phosphoryl transfer. This finding is consistent with proton donation by Lys-359 in a role as a general acid catalyst. The pH-rate profiles for K359H and K359R 3Dpols, superimposed over the profile for the K359L enzyme further support a role for Lys-359 as a proton-donating catalyst (FIG. 13). The K359H enzyme was kinetically superior to K359L at lower pHs, was maximally superior near its pKa of approximately 7.5 (Table 7 and FIG. 13), and then converged in kinetic performance toward that of K359L at higher pHs. The pH-rate behavior of K359H suggests some ability of its dissociable imidazole-group proton to enhance catalysis up to and somewhat beyond its pKa. However, the ability to enhance catalysis beyond that of Leu at position-359 is lost in K359H at higher pH values as the His imidazole becomes completely deprotonated. The K359H pH-rate profile (FIG. 13) lacks a descending basic arm (as seen for WT K359 3Dpol in FIG. 2A) because the pKa associated with transfer of the primer-template 3'-OH proton and the pKa associated with the His imidazole are likely similar enough that they are nearly superimposed on the same region of the pH-rate profile and thus unresolved.

The kinetic behavior of the K359R 3Dpol was similar to that of K359H at lower pH values (FIG. 13). However, at higher and higher pH values the K359R enzyme increasingly exceeded the kinetic performance of K359H and K359L 3Dpols, approaching that of the WT K359 polymerase at pH 10. The K359R 3Dpol pH-rate behavior is consistent with the high pKa of the Arg side chain. At lower pHs, the Arg dissociable proton is minimally unavailable to assist catalysis via proton donation. However, as its pKa is approached, the Arg dissociable proton becomes increasingly available and functions increasingly efficiently as a general acid catalyst. As expected, a basic arm for the K359R pH-rate profile was not observed up to pH 10. Reactions through at least pH 12, an experimental impossibility due to precipitation, would likely be required to observe the basic arm, given that the pKa of the Arg side chain is in the pH 12 range.

Figure 14A:
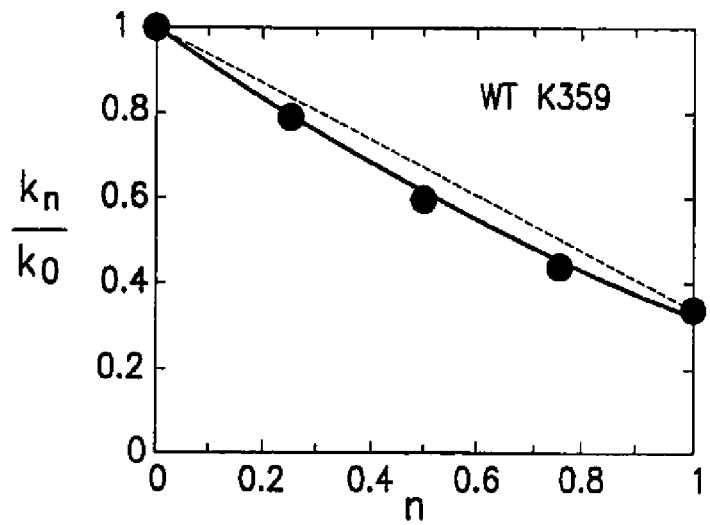
FIG. 14A: WT K359 proton inventory plot is bowl-shaped, indicating more than one rate-enhancing proton transfer during the transition state of phosphoryl transfer. The solid line is fit to a two-proton model (eq. 5) with a dashed straight line added as a visual reference.

Proton inventories reveal general-acid catalysis by PV 3Dpol Lys-359: Proton inventories for PV WT Lys-359 3Dpol were bowl-shaped, indicating transfer of more than one proton in the transition state of the phosphoryl transfer step of nucleotide incorporation (FIG. 14A). In contrast, proton inventories for the K359L mutant polymerase produced a straight-line plot indicating transfer of only one proton in the transition state. This observation is strong evidence that Lys- 359 is the donor of a catalysis-enhancing proton and thus serves as a general-acid catalyst. Consistent with this, proton inventories for the K359R 3Dpol variant were bowl-shaped, indicating some ability for Arg at position-359 position to facilitate catalysis by proton donation, as suggested above by kinetic data (Table 7) and pH-rate behavior (FIG. 13).

Figure 15A:
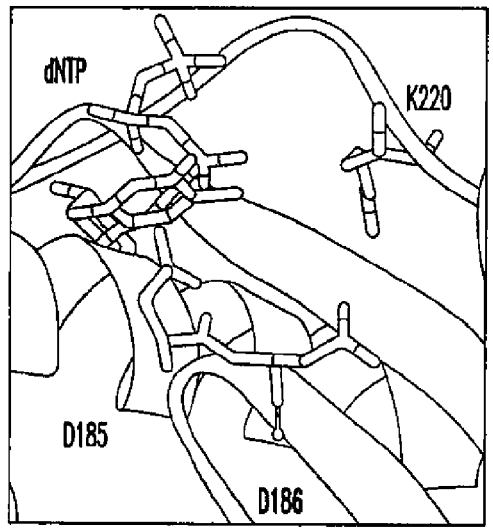
FIG. 15A: Lys-220 of HIV-1 RT RdDp.
Figure 15B:
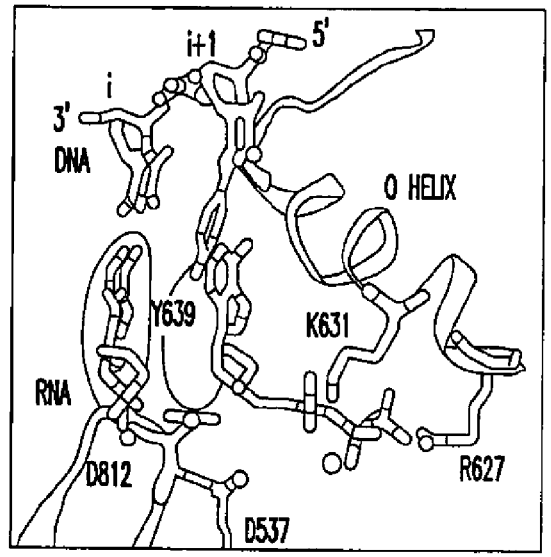
FIG. 15B: Lys-631 of T7 DdRp
Figure 15C:
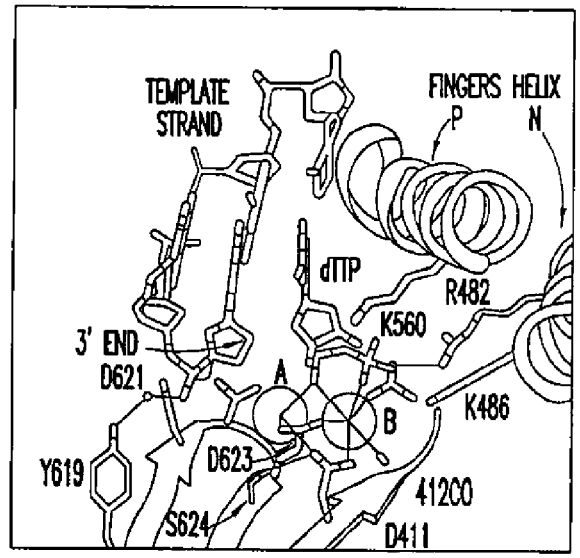
FIG. 15C: Lys-560 of RB69 DdDp. In each case the conserved Lys is believed to interact closely with the bridging oxygen between the α- and β-phosphorus atoms of the nucleotide triphosphate moiety.

A conserved active site Lys is a general acid catalyst in other polymerase classes: Sequence alignments and high resolution crystal structures permit identification of a conserved Lys residue occupying the same active site functional position as PV 3Dpol Lys-359 in nucleic acid polymerases from other classes. HIV-1 RT RdDp Lys-220 (FIG. 15A), RB69 DdDp Lys-560 (FIG. 15B) and T7 DdRp (often termed RNAP, for RNA polymerase) Lys-631 (FIG. 15C) were investigated. Consistent with findings described above for PV 3Dpol Lys-359 (Table 7), kinetic data suggest a catalytic role for the conserved active site Lys residues in these other polymerases (Table 8). Mutation of the conserved active site Lys to Leu resulted in decreased catalytic rates ranging from approximately two orders of magnitude for HIV-1 RT RdDp K220L and T7 DdRp K631L to over three orders of magnitude for RB69 DdDp K560L. While the impact of the Lys to Leu change on catalytic rates in these enzymes was consistent and severe, the influence on nucleotide binding, as reported by $K_{d,app}$, was highly variable. Little or no change was seen in HIV-1 RT K220L, a 25-fold decrease in binding affinity was seen in RB69 K560L and a devastating loss of ability to bind nucleotide substrate was seen in T7 DdRp K631L (Table 8). For the latter enzyme, saturation with nucleotide could not be accomplished experimentally. Even 75 mM ATP did not produce catalytic rates in the plateau region of a $k_{obs}$ vs. [ATP] plot. Of interest in the case of RB69 DdDp was the finding that the K560A enzyme was 10-fold kinetically superior to K560L (but still 250-fold inferior to the WT RB69 K560 polymerase). In contrast, nucleotide binding affinity for K560A and K560L were indistinguishable.

TABLE 8

Summary of kinetic parameters for HIV-1 RT RdDp, RB69 DdDp and T7 DdRp

| Polymerase | Variant | $K_{D, app}$ (μM)$^a$ | $k_{pol}$ (s$^{-1}$) | SDKIE$^b$ |
|---|---|---|---|---|
| HIV-1 RT RdDp | WT K220 | 7 ± 0.5 | 63 ± 1.2 | 2 ± 0.5 |
| HIV-1 RT RdDp | K220L | 5 ± 2 | 0.3 ± 0.3 | 2 ± 0.5 |
| RB69 DdDp | WT K560 | 38 ± 5 | 223 ± 8 | 4 ± 1 |
| RB69 DdDp | K560L | 972 ± 14 | .09 ± .003 | 2 ± 0.5 |
| RB69 DdDp | K560A | 891 ± 4 | 1.3 ± .02 | 2 ± 0.5 |
| T7 DdRp | WTK631 | 297 ± 26 | 58 ± 2 | 5 ± 1 |
| T7 DdRp | K631R | 6400 ± 0.7 | 23 ± 0.9 | nd$^d$ |
| T7 DdRp | KK631L | >83000$^c$ | >0.67 $^c$ | 3 ± 0.5$^c$ |

Figure 14B:
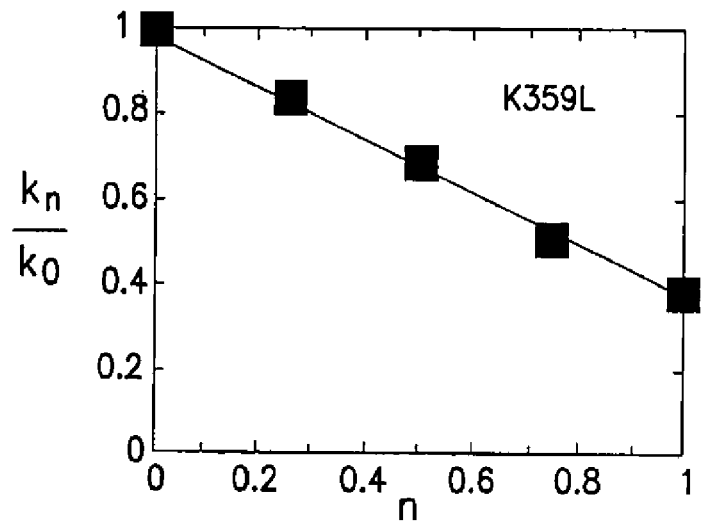
FIG. 14B: Proton inventory data for K359L 3Dpol are best fit with a one-proton, straight-line model (eq. 6) indicating that change of Lys-359 to chemically inert Leu resulted in loss of one rate-enhancing proton transfer during the phosphoryl transfer reaction.
Figure 16A:
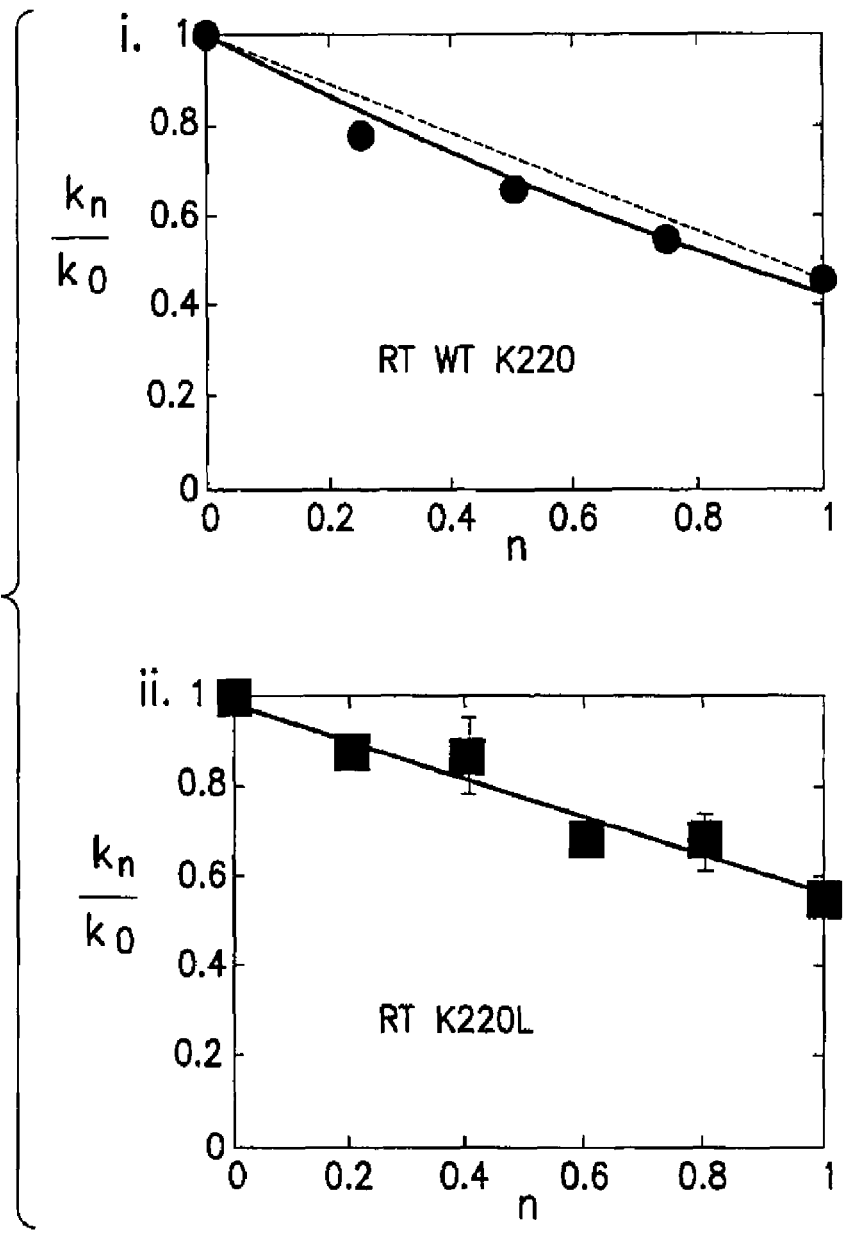
FIG. 16Ai: Proton inventory plot for HIV-1 RT WT Lys-220 RdDp is bowl-shaped indicating transfer of more than one proton in the transition state. Solid line is fit to a two-proton model (eq. 5) with dashed straight line added as a visual reference.
Figure 16B:
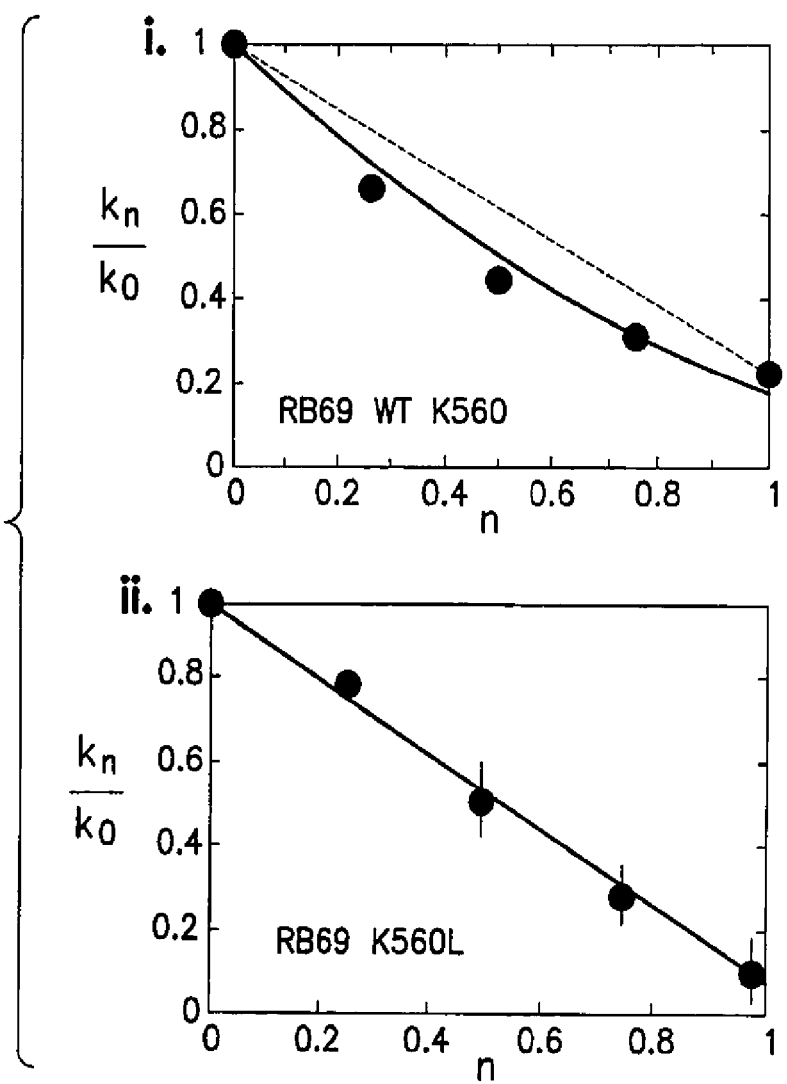
FIG. 16Bi: Similarly, WT RB69 Lys-560 DdDp proton inventory is bowl-shaped, indicating that more than one proton transfer enhances catalysis whereas Bii: proton inventory data for RB69 K560L are best fit by a straight line, indicating that only one proton transfer enhances catalysis in this variant.
Figure 16C:
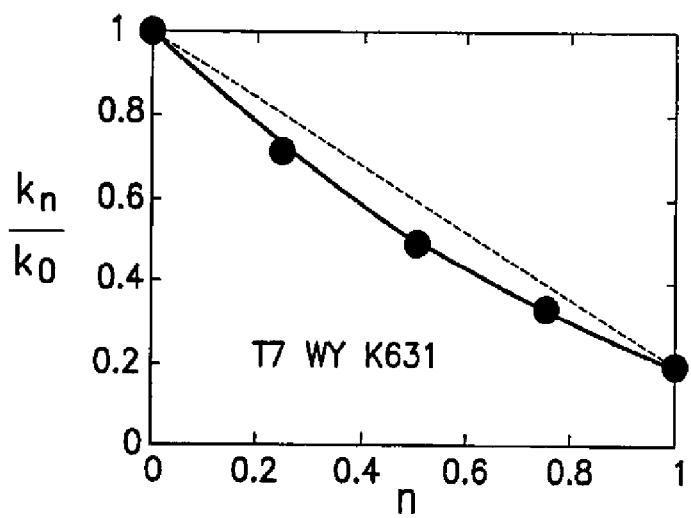
FIG. 16C: T7 DdRp WT Lys-631 proton inventory plot is bowl-shaped, indicating more than one proton transfer influencing the rate of the phosphoryl transfer step of nucleotide incorporation.
Figure 17:
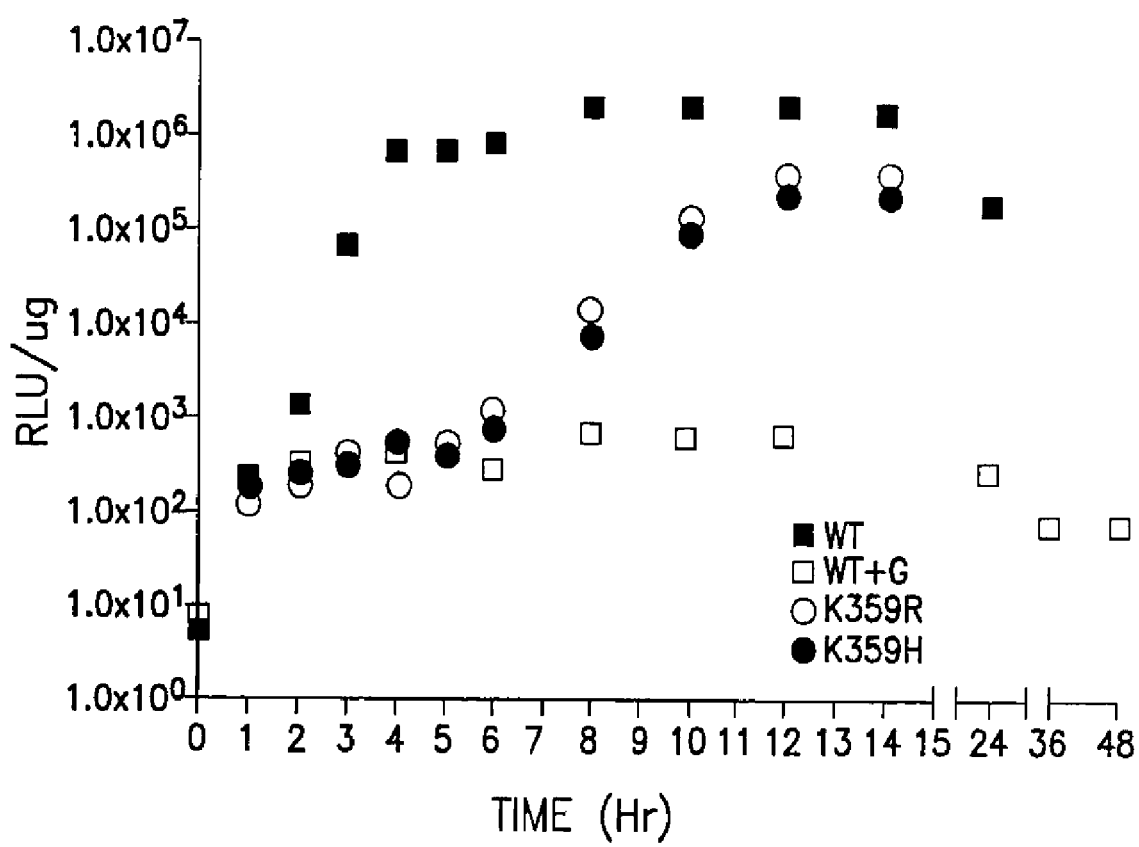
FIG. 17 is a graph illustrating that PV K359R,H subgenomic replicons replicate slower than the WT replicon.

$^a K_{d, app}$ is for ATP.
$^b$SDKIE is solvent deuterium kinetic isotope effect, calculated as $k_{obs}$ in H$_2$O/$k_{obs}$ in D$_2$O at saturating [ATP].
$^c$Values listed for T7 K631L are not actual $K_{d,app}$ and $k_{pol}$ but rather represent lower limits for these values because it was impossible to achieve saturation of reactions with ATP. Likewise, the SDKIE was obtained under sub-saturating ATP concentrations.
$^d$nd means not determined As described above for PV 3Dpol RdRp (FIG. 14), proton inventory plots for HIV-1 RT RdDp and RB69 DdDp reveal a role as catalytic general acid for the conserved active site Lys in these latter two polymerases. Proton inventory plots for WT HIV-RT K220 RdDp, T7 K631 DdRp and RB69 K560 DdDp were bowl-shaped, indicating transfer of more than one rate-influencing proton in the transition state of the phosphoryl transfer reaction during nucleotide incorporation (FIGS. 16Ai, 16Bi and 16C). In contrast, proton inventory plots for HIV-1 RT K220L (FIG. 16Aii) and RB69 K560L (FIG. 16Bii) were linear, indicating transfer of only one rate-influencing proton in the transition state. These data strongly implicate the HIV-RT RdDp and RB69 DdDp conserved active site Lys residues as general-acid catalysts.

A proton inventory for the T7 DdRp K531L polymerase could not be accomplished because, as described above, mutation of Lys to Leu in this enzyme abolished the ability to saturate the enzyme-primer/template binary complex with nucleotide experimentally.

In spite of wide diversity in the biological roles fulfilled by nucleic acid polymerases as agents of DNA and RNA replication and maintenance, the underlying active site architecture and mechanistic steps used to accomplish single nucleotide incorporation are highly conserved. In particular, the catalytic role during phosphoryl transfer has been assigned nearly exclusively to the two active site Mg$^{2+}$ ions. These metal ions position reacting functional groups, facilitate deprotonation of the primer-terminus 3'-OH to create the attacking nucleophile and alleviate negative charge build-up during the transition state.

However, the finding that two transition-state proton transfers influence the rate chemistry reveals the importance of protonic catalysis in the phosphoryl transfer reaction of nucleic acid polymerases. Abstraction of the primer-terminus 3'-OH proton likely comprises one critical proton transaction. Numerous lines of experimental evidence described in this paper converge upon the conclusion that the other critical proton exchange is proton donation by a conserved active site positively charged amino acid residue, usually lysine, acting as a general-acid catalyst. Recent high-resolution x-ray crystal structures reveal that presence of this positively charged active site residue is absolutely conserved and, even more significantly, also conserved is its spatial position near the bridging oxygen between the α- and β-phosphorus atoms of the bound nucleotide triphosphate moiety, the ideal location to facilitate bond cleavage and pyrophosphate leaving group departure. Such specific conservation demands consideration of an extremely important function. Direct participation of a conserved active site basic residue in catalysis has been largely overlooked because 1) metal ion catalysis is clearly profoundly important, 2) a role in nucleotide binding was thought to explain presence of the conserved basic residue and 3) the ability to clearly interrogate the phosphoryl transfer step has been lacking in many model polymerase systems.

In PV 3Dpol RdRp, sequence alignments and molecular modeling identified Lys-359 as the putative active site general acid (FIG. 11). pH-rate profiles of WT K359 3Dpol indicated that two ionizable functional groups influence the rate of phosphoryl transfer (FIG. 12A). Proton inventory assays further supported the transfer of two protons in the transition state for WT 3Dpol (FIG. 14A). Mutation of Lys-359 to chemically inert Leu led to a pH-rate profile lacking a basic arm (FIG. 12B), indicating only one ionizable group influencing chemistry in the K359L enzyme. Consistent with this, proton inventories of K359L 3Dpol showed transfer of only one proton in the transition state (FIG. 12B). Whereas mutation of Lys to Leu at position 359 of PV 3Dpol resulted in only a three-fold reduction in nucleotide binding affinity (the historical role ascribed to this conserved residue before its structural location was revealed), a much more profound 50-fold reduction in catalytic rate was seen (Table 7).

Figure 14C:
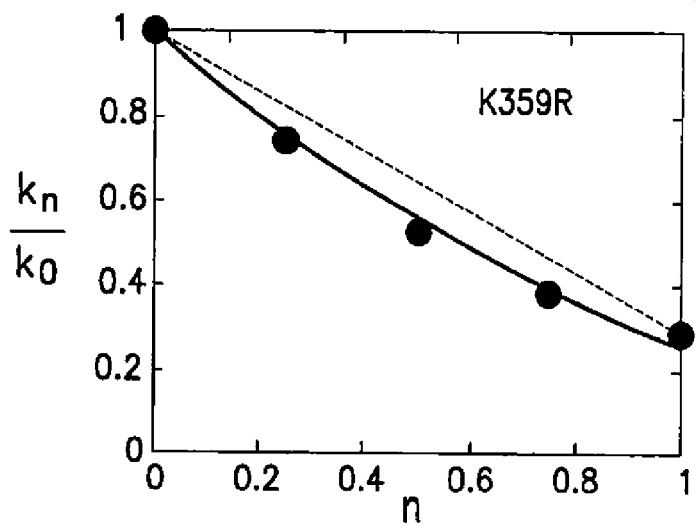
FIG. 14C: Proton inventory for K359R 3Dpol is bowl-shaped, indicating that more than one proton is transferred in the transition state when Arg occupies the 3Dpol 359 position.

Studies with K359H and K359R 3Dpols are also supportive of a role as catalytic general acid for PV 3Dpol Lys-359. The pH-rate profile of K359H 3Dpol revealed this enzyme to be kinetically superior to the K359L enzyme up to approximately one pH unit beyond the pKa of the His imidazole moiety but to then converge toward the catalytic inefficiency of K359L 3Dpol at higher pHs (FIG. 13). The pH-rate profile of K359R 3Dpol showed this enzyme to be kinetically similar to K359H 3Dpol at lower pHs, but at higher and higher pHs the K359R polymerase performed catalytically better and better until, by pH 10, catalytic rates of K359R approached those of the WT K359 enzyme (FIG. 13). Also consistent with a role as general acid catalyst of 3Dpol Lys-359 was the finding that proton inventories for K359R 3Dpol revealed two proton transfers in the transition state for this polymerase variant (FIG. 14c). Mutation of Lys-359 to His or Arg left nucleotide binding essentially unaffected relative to the WT 3Dpol enzyme but resulted in catalytic rates 10-fold slower than WT K359 and five-fold faster than K359L 3Dpol (Table 7). In summary, experimental data for the PV 3Dpol K359H and K359R polymerase variants suggest that some residual general acid catalytic function exits when His or Arg occupy position 359 but that protonic catalysis occurs with substantially reduced efficiency compared to WT Lys-359. This is likely the result of proton donation limitations due to pKa mismatches between proton donor and acceptor groups and/or spatial misalignments between interacting atoms when the non-biological His or Arg occupy this active site position in PV 3Dpol.

In further support of a role as catalytic general acid for the conserved polymerase active site positively charged amino acid residue is extension of this conclusion described above for PV 3Dpol RdRp to other classes of polymerases. The combination of sequence alignments and high-resolution x-ray crystal structures permitted identification of a conserved active site lysine putative general acid in HIV-1 RT RdDp (K220) (FIG. 15A), RB69 DdDp (K560) (FIG. 15B) and T7 DdRp (K631) (FIG. 15C). In each of these polymerases, mutation of the conserved active site Lys to Leu resulted in large decreases in catalytic rate of approximately two-three orders of magnitude (Table 8). Of interest in the case of RB69 DdDp is the finding that K560A polymerase was an order of magnitude kinetically superior to the K560L variant (but still two orders of magnitude inferior to the WT Lys-560 enzyme) in terms of catalytic rate, whereas the K560A and K560L enzymes were equivalent in nucleotide binding (Table 8). A possible explanation for the kinetic superiority of K560A over K560L is that the small Ala side chain may provide space for stable insertion of a structural water molecule which can contribute catalytically at the site, albeit inefficiently.

Proton inventory plots for WT HIV-1 RT RdDp, RB69 DdDp and T7 DdRp were clearly bowl-shaped, revealing transfer of more than one rate-influencing proton in the transition state of phosphoryl transfer (FIGS. 16Ai, 16Bi and 16C). In contrast, proton inventory plots for the HIV-1 RT K220L and RB69 K560L polymerases were linear, indicating that only one proton was being transferred in the transition state (FIGS. 16Aii and 16Bii). These proton inventory findings were similar to those described above for PV 3Dpol RdRp (FIGS. 14A and 14B). Therefore, in PV 3Dpol RdRp, HIV-1 RT RdDp and RB69 DdDp mutation of the conserved active site Lys to protonically inert Leu eliminated one rate-influencing proton transfer in the transition state of the phosphoryl transfer step and reduced the catalytic rate two-three orders of magnitude.

How nucleic acid polymerases enforce fidelity is currently highly controversial. Lack of ability to saturate T7 DdRp K631L reactions with nucleotide substrate experimentally appears consistent with the observation that in yeast, RNAP II nucleotide binding and catalysis may be coupled by an active site basic residue, His-1085. It has been further suggested that coupling of substrate selection and catalysis may enforce fidelity in RNA polymerases. The T7 RNAP O-helix, which bears Lys-631, may be functionally analogous to the yeast RNAP II trigger loop, which bears His-1085; both are mobile structural elements involved in nucleotide entry into the polymerase active site. The findings reported here that mutation of RB69 Lys-560 to Leu resulted in a 25-fold reduction in $K_{d,app}$ (to go along with a 2500-fold reduction in $k_{pol}$) with dATP as substrate (Table 8) suggests a significant role for this residue in nucleotide binding and a possible coupling with catalysis. However, lack of substantial changes in nucleotide binding upon mutation of the catalytic Lys to Leu in PV 3Dpol RdRp and HIV-1 RdDp, in spite of decreases of approximately two orders of magnitude in catalytic rate (Tables 7 and 8) suggest that coupling of substrate binding and catalysis may not be a feature of these polymerases.

The mechanistic model favored here involves donation of a proton from the active site general acid to the pyrophosphate leaving group to facilitate bond cleavage and leaving group departure. However, it should be noted that complete physical donation of the proton may not be a requirement for successful catalysis and that proton sharing may be sufficient. In summary, multiple lines of evidence described herein collectively argue that a conserved active site positively charged amino acid residue serves an important function as general acid catalyst in nucleic acid polymerases. Proton donation/sharing is the simplest, most fundamental means of dissipating energetically unfavorable negative charge development in enzyme active-site reactions. The findings reported here are important because they reveal a more complete picture of how the catalysis of phosphoryl transfer is accomplished by this universally important group of enzymes. While two-metal-ion catalysis is clearly profoundly important and provides the primary basis for acceleration of nucleotide incorporation, rates imparted by metal-ion-catalysis alone may be inadequate. The additional two-three orders of magnitude of catalytic-rate enhancement supplied by the active site general acid may be necessary to bring nucleotide incorporation rates to a level of biological sufficiency. Indeed, cell culture studies of 3Dpol K359H and K359R mutant polioviruses show substantially-slowed plaque formation by these variants, suggesting that infectivity and pathogenesis may prove to be attenuated due to inadequate rates of viral genome replication.

Example 3

Mutant PVs

PV mutant viruses K359R and K359H were made and shown to replicate (FIG. 17), and to be infectious and attenuated in cells relative to WT virus. HeLa cells were transfected with wild-type PV RNA, RNA containing the indicated mutations in 3Dpol, or no RNA (mock transfection), diluted 100-fold in PBS, then plated onto a monolayer of untransfected HeLa cells. Plates were covered with agar media and incubated at 37° C. for two days. FIG. 17 illustrates that PV K359R,H subgenomic replicons replicate slower than WT. The subgenomic replicon employed had the capsid-coding region replaced by a luciferase reporter gene. HeLa cells were transfected with a subgenomic replicon RNA containing the WT sequence in the presence of 2 mM GdnHCL (+G) or WT sequence in the absence of GdnHCL. GdnHCL is a reversible inhibitor of PV RNA replication; therefore, the luciferase activity measured in the presence of GdnHCL is the result of translation of the input RNA. In the absence of GdnHCL, transfections were also performed using replicons containing the K359R,H mutations. Transfection reactions were incubated at 37° C. At various times after transfection, cells were processed and luciferase activity evaluated.

OTHER EMBODIMENTS

Any improvement may be made in part or all of the compositions and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Although modified polymerases are described herein having a substitution at a lysine residue in the active site of the polymerase, a modified polymerase as described herein includes mutations, deletions, and substitutions of proton-accepting and proton-donating amino acid residues. Any molecule that changes the activity (e.g., rate of replication, fidelity, etc.) of the polymerase can be utilized. Moreover, any combination of the above-described elements in all possible variations thereof is encompassed by the invention unless otherwise indicated herein or otherwise clearly contraindicated by context.

What is claimed is:

1. An attenuated poliovirus comprising a polymerase gene that encodes a poliovirus RNA-dependent RNA polymerase, the polymerase gene having a modification that results in a substitution of a lysine residue to a histidine or arginine residue, the lysine residue capable of functioning as a general acid catalyst during a phosphoryl transfer step of a nucleotide incorporation reaction and located on the loop of structural motif D of the RNA-dependent RNA polymerase, wherein the substitution causes the polymerase to have increased fidelity compared to a polymerase encoded by a wild-type poliovirus polymerase gene not having the modification.

2. The attenuated poliovirus of claim 1, wherein the lysine residue is at position 359 of an amino acid sequence encoded by the nucleic acid sequence of SEQ ID NO: 9.

3. The attenuated poliovirus of claim 1, wherein the virus is infectious.

4. A vaccine comprising: (a) an attenuated poliovirus comprising a polymerase gene that encodes a poliovirus RNA-dependent RNA polymerase, the polymerase gene having a modification that results in a substitution of a lysine residue to an arginine residue, the lysine residue capable of functioning as a general acid catalyst during a phosphoryl transfer step of a nucleotide incorporation reaction and located on the loop of structural motif D of the RNA-dependent RNA polymerase, wherein the substitution causes the polymerase to have increased fidelity compared to a polymerase encoded by a wild-type poliovirus polymerase gene not having the modification; and (b) a pharmaceutically acceptable carrier.

5. The vaccine of claim 4, wherein the lysine residue is at position 359 of an amino acid sequence encoded by the nucleic acid sequence of SEQ ID NO: 9.

6. The vaccine of claim 4, wherein the vaccine further comprises an adjuvant.

7. A purified nucleic acid comprising a polymerase gene that encodes a poliovirus RNA-dependent RNA polymerase, the polymerase gene having a modification that results in a substitution of a lysine residue to a histidine or arginine residue, the lysine residue capable of functioning as a general acid catalyst during a phosphoryl transfer step of a nucleotide incorporation reaction and located on the loop of structural motif D of the RNA-dependent RNA polymerase, wherein the substitution causes the polymerase to have increased fidelity compared to a polymerase encoded by a wild-type poliovirus polymerase gene not having the modification.

8. A vector comprising the nucleic acid of claim 7.

9. A method of attenuating a poliovirus comprising modifying a viral polymerase gene that encodes a poliovirus RNA-dependent RNA polymerase, such that the modification results in a substitution of a lysine residue to a histidine or arginine residue, the lysine residue capable of functioning as a general acid catalyst during a phosphoryl transfer step of a nucleotide incorporation reaction and located on the loop of structural motif D of the RNA-dependent RNA polymerase, wherein the substitution causes the polymerase to have increased fidelity compared to a polymerase encoded by a wild-type poliovirus polymerase gene not having the modification.

10. A composition comprising: (a) an attenuated poliovirus comprising a polymerase gene that encodes a poliovirus RNA-dependent RNA polymerase, the polymerase gene having a modification that results in a substitution of a lysine residue to a histidine or arginine residue, the lysine residue capable of functioning as a general acid catalyst during a phosphoryl transfer step of a nucleotide incorporation reaction and located on the loop of structural motif D of the RNA-dependent RNA polymerase, wherein the substitution causes the polymerase to have increased fidelity compared to a polymerase encoded by a wild-type poliovirus polymerase gene not having the modification; and (b) a pharmaceutically acceptable carrier.

11. The composition of claim 10, wherein the lysine residue is at position 359 of an amino acid sequence encoded by the nucleic acid sequence of SEQ ID NO: 9.

* * * * *

SEQUENCE LISTING

```
<160> NUMBER OF SEQ ID NOS: 29

<210> SEQ ID NO 1
<211> LENGTH: 13
<212> TYPE: DNA
<213> ORGANISM: ARTIFICIAL
<220> FEATURE:
<223> OTHER INFORMATION: OLIGONUCLEOTIDE

<400> SEQUENCE: 1
ccgaccagcc ttg                                                      13

<210> SEQ ID NO 2
<211> LENGTH: 19
<212> TYPE: DNA
<213> ORGANISM: ARTIFICIAL
<220> FEATURE:
<223> OTHER INFORMATION: OLIGONUCLEOTIDE
<220> FEATURE:
<221> NAME/KEY: modified_base
<222> LOCATION: (5)..(5)
<223> OTHER INFORMATION: 2ap

<400> SEQUENCE: 2
aaagctcaag gctggtcgg                                                19

<210> SEQ ID NO 3
<211> LENGTH: 12
<212> TYPE: RNA
<213> ORGANISM: ARTIFICIAL
<220> FEATURE:
<223> OTHER INFORMATION: OLIGONUCLEOTIDE

<400> SEQUENCE: 3
uuuugccgcg cc                                                       12

<210> SEQ ID NO 4
<211> LENGTH: 16
<212> TYPE: DNA
<213> ORGANISM: ARTIFICIAL
<220> FEATURE:
<223> OTHER INFORMATION: OLIGONUCLEOTIDE
<220> FEATURE:
<221> NAME/KEY: modified_base
<222> LOCATION: (7)..(7)
<223> OTHER INFORMATION: 2AP

<400> SEQUENCE: 4
```

-continued ggaatgctgg cgcggc 16

<210> SEQ ID NO 5
<211> LENGTH: 23
<212> TYPE: DNA
<213> ORGANISM: ARTIFICIAL
<220> FEATURE:
<223> OTHER INFORMATION: OLIGONUCLEOTIDE

<400> SEQUENCE: 5
ttaaaagaaa agggggact gga 23

<210> SEQ ID NO 6
<211> LENGTH: 57
<212> TYPE: DNA
<213> ORGANISM: ARTIFICIAL
<220> FEATURE:
<223> OTHER INFORMATION: OLIGONUCLEOTIDE

<400> SEQUENCE: 6
cgttgggagt gaattagccc ttccagtccc cccttttctt ttaaaaagtg gctaaga 57

<210> SEQ ID NO 7
<211> LENGTH: 34
<212> TYPE: DNA
<213> ORGANISM: ARTIFICIAL
<220> FEATURE:
<223> OTHER INFORMATION: OLIGONUCLEOTIDE

<400> SEQUENCE: 7
gcacaaatta atcgtctgtt gcttatcaac tcac 34

<210> SEQ ID NO 8
<211> LENGTH: 34
<212> TYPE: DNA
<213> ORGANISM: ARTIFICIAL
<220> FEATURE:
<223> OTHER INFORMATION: OLIGONUCLEOTIDE

<400> SEQUENCE: 8
gtgagttgat aagcaacaga cgattaattt gtgc 34

<210> SEQ ID NO 9
<211> LENGTH: 7433
<212> TYPE: DNA
<213> ORGANISM: Human Poliovirus

<400> SEQUENCE: 9
ttaaaacagc tctggggttg tacccacccc agaggcccac gtggcggcta gtactccggt 60
attgcggtac ccttgtacgc ctgttttata ctcccttccc gtaacttaga cgcacaaaac 120
caagttcaat agaagggggt acaaaccagt accaccacga acaagcactt ctgtttcccc 180
ggtgatgtcg tatagactgc ttgcgtggtt gaaagcgacg gatccgttat ccgcttatgt 240
acttcgagaa gcccagtacc acctcggaat cttcgatgcg ttggttagca ctcaacccca 300
gagtgtagct taggctgatg agtctggaca tccctcaccg gtgacggtgt tccaggctgc 360
gttggcggcc tacctatggc taacgcatgg gacgctagtt gtgaacaagg tgtgaagagc 420
ctattgagct acataagaat cctccggccc ctgaatgcgg ctaatcccaa cctcggagca 480
ggtggttcac aaaccagtga ttggcctgtc gtaacgcgca agtccgtggc ggaaccgact 540
actttgggtg tccgtgtttc cttttatttt attgtggctg cttatggtga caatcacaga 600
ttgttatcat aaagcgaatt ggattggcca tccggtgaaa gtgagactca ttatctatct 660

-continued

```
gtttgctgga tccgctccat tgagtgtgtt tactctaagt acaatttcaa cagttatttc     720
aatcagacaa ttgtatcata atgggtgctc aggtttcatc acagaaagtg ggcgcacatg     780
aaaactcaaa tagagcgtat ggtggttcta ccattaatta caccaccatt aattattata     840
gagattcagc tagtaacgcg gcttcgaaac aggacttctc tcaagaccct ccaagttca      900 ccgagcccat caaggatgtc ctgataaaaa cagccccaat gctaaactcg ccaaacatag     960
aggcttgcgg gtatagcgat agagtactgc aattaacact gggaaactcc actataacca    1020
cacaggaggc ggctaattca gtagtcgctt atgggcgttg gcctgaatat ctgagggaca    1080
gcgaagccaa tccagtggac cagccgacag aaccagacgt cgctgcatgc aggttttata    1140
cgctagacac cgtgtcttgg acgaaagagt cgcgagggtg gtggtggaag ttgcctgatg    1200
cactgaggga catgggactc tttgggcaaa atatgtacta ccactaccta ggtaggtccg    1260
ggtacaccgt gcatgtacag tgtaacgcct ccaaattcca ccaggggca ctaggggtat     1320 tcgccgtacc agagatgtgt ctggccgggg atagcaacac cactaccatg cacaccagct    1380
atcaaaatgc caatcctggc gagaaaggag gcactttcac gggtacgttc actcctgaca    1440
acaaccagac atcacctgcc cgcagttctg cccggtggat tacctccttg gaaatggcac    1500
gttgttgggg aatgcctttg tgttccgcac agataataaa cttacggacc aacaactgtg    1560
ctacactggt actaccttac gtgaactccc tctcgctaga tagtatggta aagcacaata    1620 attgggaat tgcaatatta ccattggccc cattaaattt tgttagtgag tcctccccag     1680
agattccaat caccttgacc atagcccta tgtgctgtga gttcaatgga ttaagaaaca    1740
tcaccctgcc acgcttacag ggcctgccgg tcatgaacac ccctggtagc aatcaatatc    1800
ttactgcaga caacttccag tcaccgtgtg cgctgcctga atttgatgtg accccaccta    1860
ttgacatacc cggtgaagta aagaacatga tggaattggc agaaatcgac accatgattc    1920
cctttgactt aagtgccaca aaaaagaaca ccatggaaat gtatagggtt cggttaagtg    1980
acaaaccaca tacagccgcc tccatactct gcctgtcact ctctccagcc tcagatccta    2040
ggttgtcaca tactatgctt ggagaaatcc taaattacta cacacactgg gcaggatccc    2100
tgaagttcac gtttctgttc tgtggatcca tgatggcaac tggcaaactg ttggtgtcat    2160
acgcgcctcc tggagccgac ccaccaaaga agcgtaagga ggcgatgttg gaacacatg     2220 tgatctggga cataggactg cagtcctcat gtactatggt agtgccatgg attagcaaca    2280
gcacgtatcg gcaaaccata gatgatagtt tcaccgaagg cggatacatc agcgtcttct    2340
accaaactag aatagtcgtc cctctttcga cacccagaga gatggacatc cttggttttg    2400
tgtcagcgtg taatgacttc agcgtgcgct tgttgcgaga taccacacat atagagcaaa    2460
aagcgctagc acaggggtta ggtcagatgc ttgaaagcat gattgacaac acagtccgtg    2520
aaacggtggg ggcggcaaca tctagagacg ctctcccaaa cactgaagcc agtggaccaa    2580
cacactccaa ggaaattccg gcactcaccg cagtggaaac tgggccaca aatccactag     2640 tcccttctga tacagtgcaa accagacatg ttgtacaaca taggtcaagg tcagagtcta    2700
gcatagagtc tttcttcgcg cggggtgcat gcgtgaccat tatgaccgtg ataacccag     2760 cttccaccac gaataaggat aagctatttg cagtgtggaa gatcacttat aaagatactg    2820
tccagttacg gaggaaattg gagttcttca cctattctag atttgatatg gaacttacct    2880
ttgtggttac tgcaaatttc actgagacta acaatgggca tgccttaaat caagtgtacc    2940
aaattatgta cgtaccacca ggcgctccag tgcccgaaaa atgggacgac tacacatggc    3000
```

```
aaacctcatc aaatccatca atcttttaca cctacgggac agctccagcc cggatctcgg    3060
taccgtatgt tggtatttcg aacgcctatt cacactttta cgacggtttt tccaaagtac    3120
cactgaagga ccagtcggca gcactaggtg actcccttta tggtgcagca tctctaaatg    3180
acttcggtat tttggctgtt agagtagtca atgatcacaa cccgaccaag gtcacctcca    3240
aaatcagagt gtatctaaaa cccaaacaca tcagagtctg gtgcccgcgt ccaccgaggc    3300
agctggcgta ctacggccct ggagtggatt acaaggatgg tacgcttaca ccctctcca    3360 ccaaggatct gaccacatat ggattcggac accaaaacaa agcggtgtac actgcaggtt    3420
acaaaatttg caactaccac ttggccactc aggatgattt gcaaaacgca gtgaacgtca    3480
tgtggagtag agacctctta gtcacagaat caagagccca gggcaccgat tcaatcgcaa    3540
ggtgcaattg caacgcaggg gtgtactact gcgagtctag aaggaaatac tacccagtat    3600
ccttcgttgg cccaacgttc cagtacatgg aggctaataa ctattaccca gttaggtacc    3660
agtcccatat gctcattggc catggattcg aatctccagg ggattgtggt ggcatactca    3720
gatgtcacca cggggtgata gggatcatta ctgctggtgg agaagggttg gttgcatttt    3780
cagacattag agacttgtat gcctacgaag aagaagccat ggaacaaggc atcaccaatt    3840
acatagagtc acttggggcc gcatttggaa gtggatttac tcagcagatt agcgacaaaa    3900
taacagagtt gaccaatatg gtgaccagta ccatcactga aaagctactt aagaacttga    3960
tcaagatcat atcctcacta gttattataa ctaggaacta tgaagacacc acaacagtgc    4020
tcgctaccct ggcccttctt gggtgtgatg cttcaccatg gcagtggctt agaaagaaag    4080
catgcgatgt tctggagata ccttatgtca tcaagcaagg tgacagttgg ttgaagaagt    4140
ttactgaagc atgccaacga gctaagggcc tggagtgggt gtcaaacaaa atctcaaaat    4200
tcattgattg gctcaaggag aaaattatcc cacaagctag agataagttg gaatttgtaa    4260
caaaacttag acaactagaa atgctggaaa accaaatctc aactatacac caatcatgcc    4320
ctagtcagga acaccaggaa attctattca ataatgtcag atggttatcc atccagtcta    4380
agaggtttgc ccctctttac gcagtggaag ccaaaagaat acagaaacta gagcatacta    4440
ttaacaacta catacagttc aagagcaaac accgtattga accagtatgt ttgctagtac    4500
atggcagccc cggaacaggt aaatctgtag caaccaacct gattgctaga gccatagctg    4560
aaagagaaaa cacgtccacg tactcgctac ccccggatcc atcacacttc gacggataca    4620
aacaacaggg agtggtgatt atggacgacc tgaatcaaaa cccagatggt gcggacatga    4680
agctgttctg tcagatggta tcaacagtgg agtttatacc acccatggca tccctggagg    4740
agaaaggaat cctgtttact tcaaattacg ttctagcatc cacaaactca agcagaattt    4800
ccccccccac tgtggcacac agtgatgcat tagccaggcg ctttgcgttc gacatggaca    4860
ttcaggtcat gaatgagtat tctagagatg ggaaattgaa catggccatg gctactgaaa    4920
tgtgtaagaa ctgtcaccaa ccagcaaact taagagatg ctgtccttta gtgtgtggta    4980
aggcaattca attaatggac aaatcttcca gagttagata cagtattgac cagatcacta    5040
caatgattat caatgagaga acagaagat ccaacattgg caattgtatg gaggctttgt    5100
ttcaaggccc actccagtat aaagacttga aaattgacat caagacgagt cccctcctg    5160 aatgtatcaa tgcttgctc caagcagttg actcccagga ggtgagagat tactgtgaga    5220
agaagggttg gatagtcaac atcaccagcc aggttcaaac agaaaggaac atcaacaggg    5280
caatgacaat tctacaagcg gtgacaacct tcgccgcagt ggctgagtt gtctatgtca    5340 tgtataaaact gtttgctgga caccagggag catacactgg tttaccaaac aaaaaaccca    5400
```

```
acgtgcccac cattcggaca gcaaaggtac aaggaccagg gttcgattac gcagtggcta     5460
tggctaaaag aaacattgtt acagcaacta ctagcaaggg agagttcact atgttaggag     5520
tccacgacaa cgtggctatt ttaccaaccc acgcttcacc tggtgaaagc attgtgatcg     5580
atggcaaaga agcggagatc ttggatgcca agtgtttga agatcaagca ggaaccaatt     5640
ttgaaatcac tataatcact ctaaagagaa atgaaaagtt cagagacatt agaccacata     5700
tacctactca aatcactgag acaaatgatg gagtcttgat cgtgaacact agcaagtacc     5760
ccaatatgta tgttcctgtc cgtgctgtga ctgaacaggg atatctaaat ctcggtgggc     5820
gccaaactgc tcgtactcta atgtacaact ttccaaccag agcaggacag tgtggtggag     5880
tcatcacatg tactgggaag tcatcgggat gcatgttggt ggacggttca cacgggtttg     5940
cagcggccct gaagcgatca ttattcactc agagtcaagg tgaaatcccg tggatgagac     6000
cttcgaagga cgcgggatat ccaatcataa atgccccgtc caaaaccaag cttgaaccca     6060
gtgctttcca ctatgtgttt gaaggggtga aggaaccagc agtcctcact aaaaacgatc     6120
ccaggcttaa gacagacttt gaggaggcaa ttttctccaa gtacgtgggt aacaaaatta     6180
ctgaagtgga tgagtacatg aaagaggcag tagaccacta tgctggccag ctcatgtcac     6240
tagacatcaa catagaacaa atgtgcttgg aggatgccat gtatggcact gatggtctag     6300
aagcacttga tttgtccacc agtgctggct acccttatgt agcaatggga aagaagaaga     6360
gagacatctt gaacaaacaa accagagaca ctaaggaaat gcaaaaactg ctcgacacat     6420
atggaatcaa cctcccactg gtgacttatg taaaggatga acttagatcc aaaacaaagg     6480
ttgagcaggg gaaatccaga ttaattgaag cttctagttt gaatgactca gtggcaatga     6540
gaatggcttt tgggaaccta tatgctgctt tcacaaaaaa cccaggagtg ataacaggtt     6600
cagcagtggg gtgcgatcca gatttgtttt ggagcaaaat tccggtattg atggaagaga     6660 agctgttgc ttttgactac acagggtatg atgcatctct cagccctgct tggttcgagg     6720
cactaaagat ggtgcttgag aaaatcggat tcggagacag agttgactac atcgactacc     6780
taaaccactc acaccacctg tacaagaata aaacatactg tgtcaaggc ggtatgccat     6840 ctggctgctc aggcacttca attttaact caatgattaa caacttgatt atcaggacac     6900
tcttactgaa aacctacaag gcatagatt tagaccacct aaaaatgatt gcctatggtg     6960
atgatgtaat tgcttcctac ccccatgaag ttgacgctag tctcctagcc caatcaggaa     7020
aagactatgg actaactatg actccagctg acaaatcagc tacatttgaa acagtcacat     7080
gggagaatgt aacattcttg aagagattct tcagggcaga cgagaaatac ccatttctta     7140
ttcatccagt aatgccaatg aaggaaattc atgaatcaat tagatggact aaagatccta     7200
ggaacactca ggatcacgtt cgctctctgt gccttttagc ttggcacaat ggcgaagaag     7260
aatataacaa attcctagct aaaatcagga gtgtgccaat ggaagagct ttattgctcc     7320 cagagtactc aacattgtac cgccgttggc ttgactcatt ttagtaaccc tacctcagtc     7380
gaattggatt gggtcatact gctgtagggg taaattttc tttaattcgg agg            7433
```

<210> SEQ ID NO 10
<211> LENGTH: 757
<212> TYPE: PRT
<213> ORGANISM: Influenza A virus

<400> SEQUENCE: 10

Met Asp Val Asn Pro Thr Leu Leu Phe Leu Lys Val Pro Ala Gln Asn
1               5                   10                  15

```
Ala Ile Ser Thr Thr Phe Pro Tyr Thr Gly Asp Pro Tyr Ser His
            20                  25                  30

Gly Thr Gly Thr Gly Tyr Thr Met Asp Thr Val Asn Arg Thr His Gln
                35                  40                  45

Tyr Ser Glu Lys Gly Lys Trp Thr Thr Asn Thr Glu Thr Gly Ala Pro
 50                  55                  60

Gln Leu Asn Pro Ile Asp Gly Pro Leu Pro Glu Asp Asn Glu Pro Ser
 65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
                100                 105                 110

Val Val Gln Gln Thr Arg Val Asp Lys Leu Thr Gln Gly Arg Gln Thr
                115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Asp Lys
                165                 170                 175

Glu Glu Met Glu Ile Thr Thr His Phe Gln Arg Lys Arg Arg Val Arg
                180                 185                 190

Asp Asn Met Thr Lys Lys Met Val Thr Gln Arg Thr Ile Gly Lys Lys
                195                 200                 205

Lys Gln Arg Val Asn Lys Arg Gly Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
                260                 265                 270

Val Gly Gly Asn Glu Lys Lys Ala Lys Leu Ala Asn Val Val Arg Lys
    275                 280                 285

Met Met Thr Asn Ser Gln Asp Thr Glu Leu Ser Phe Thr Ile Thr Gly
                290                 295                 300

Asp Asn Thr Lys Trp Asn Glu Asn Gln Asn Pro Arg Met Phe Leu Ala
305                 310                 315                 320

Met Ile Thr Tyr Ile Thr Lys Asn Gln Pro Glu Trp Phe Arg Asn Ile
                325                 330                 335

Leu Ser Ile Ala Pro Ile Met Phe Ser Asn Lys Met Ala Arg Leu Gly
                340                 345                 350

Lys Gly Tyr Met Phe Glu Ser Lys Arg Met Lys Leu Arg Thr Gln Ile
    355                 360                 365

Pro Ala Glu Met Leu Ala Asn Ile Asp Leu Lys Tyr Phe Asn Glu Ser
    370                 375                 380

Thr Arg Lys Lys Ile Glu Lys Ile Arg Pro Leu Leu Ile Asp Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Lys Tyr Thr
                420                 425                 430
```

```
Lys Thr Thr Tyr Trp Asp Gly Leu Gln Ser Ser Asp Phe Ala
        435                 440                 445

Leu Ile Val Asn Ala Pro Asn His Glu Gly Ile Gln Ala Gly Val Asp
        450                 455                 460

Arg Phe Tyr Arg Thr Cys Lys Leu Val Gly Ile Asn Met Ser Lys Lys
465                 470                 475                 480

Lys Ser Tyr Ile Asn Lys Thr Gly Thr Phe Glu Phe Thr Ser Phe Phe
                485                 490                 495

Tyr Arg Tyr Gly Phe Val Ala Asn Phe Ser Met Glu Leu Pro Ser Phe
                500                 505                 510

Gly Val Ser Gly Ile Asn Glu Ser Ala Asp Met Ser Ile Gly Val Thr
                515                 520                 525

Val Ile Lys Asn Asn Met Ile Asn Asn Asp Leu Gly Pro Ala Thr Ala
        530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Asp Gln Thr Gln Ser Arg Ala Gly Leu Leu Val Ser
                580                 585                 590

Asp Gly Gly Pro Asn Leu Tyr Asn Ile Arg Asn Leu His Ile Pro Glu
                595                 600                 605

Val Cys Leu Lys Trp Glu Leu Met Asp Glu Asn Tyr Arg Gly Arg Leu
        610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Ala Thr Thr His Ser Trp Ile Pro Lys Arg Asn Arg
                660                 665                 670

Ser Ile Leu Asn Thr Ser Gln Arg Gly Ile Leu Glu Asp Glu Gln Met
                675                 680                 685

Tyr Gln Lys Cys Cys Asn Leu Phe Glu Lys Phe Phe Pro Ser Ser Ser
        690                 695                 700

Tyr Arg Arg Pro Ile Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ser Glu Ile Met Lys Ile Cys Ser Thr Ile Glu Glu
                740                 745                 750

Leu Arg Arg Gln Lys
        755

<210> SEQ ID NO 11
<211> LENGTH: 554
<212> TYPE: PRT
<213> ORGANISM: Human immunodeficiency virus type 1

<400> SEQUENCE: 11

Lys Ile Ser Pro Ile Glu Thr Val Pro Val Lys Leu Lys Pro Gly Met
1               5                   10                  15

Asp Gly Pro Lys Val Lys Gln Trp Pro Leu Thr Glu Glu Lys Ile Lys
                20                  25                  30

Ala Leu Val Glu Ile Cys Thr Glu Met Glu Lys Glu Gly Lys Ile Ser
        35                  40                  45
```

```
Lys Ile Gly Pro Glu Asn Pro Tyr Asn Thr Pro Val Phe Ala Ile Lys
 50                  55                  60

Lys Lys Asp Ser Thr Lys Trp Arg Lys Leu Val Asp Phe Arg Glu Leu
 65                  70                  75                  80

Asn Lys Arg Thr Gln Asp Phe Trp Glu Val Gln Leu Gly Ile Pro His
                 85                  90                  95

Pro Ala Gly Leu Lys Lys Lys Ser Val Thr Val Leu Asp Val Gly
                100                 105                 110

Asp Ala Tyr Phe Ser Val Pro Leu Asp Glu Asp Phe Arg Lys Tyr Thr
                115                 120                 125

Ala Phe Thr Ile Pro Ser Ile Asn Asn Glu Thr Pro Gly Ile Arg Tyr
        130                 135                 140

Gln Tyr Asn Val Leu Pro Gln Gly Trp Lys Gly Ser Pro Ala Ile Phe
145                 150                 155                 160

Gln Ser Ser Met Thr Lys Ile Leu Glu Pro Phe Arg Lys Gln Asn Pro
                165                 170                 175

Asp Ile Val Ile Tyr Gln Tyr Met Asp Asp Leu Tyr Val Gly Ser Asp
                180                 185                 190

Leu Glu Ile Gly Gln His Arg Thr Lys Ile Glu Glu Leu Arg Gln His
        195                 200                 205

Leu Leu Arg Trp Gly Leu Thr Thr Pro Asp Lys His Gln Lys Glu
210                 215                 220

Pro Pro Phe Leu Trp Met Gly Tyr Glu Leu His Pro Asp Lys Trp Thr
225                 230                 235                 240

Val Gln Pro Ile Val Leu Pro Glu Lys Asp Ser Trp Thr Val Asn Asp
                245                 250                 255

Ile Cys Lys Leu Val Gly Lys Leu Asn Trp Ala Ser Gln Ile Tyr Pro
                260                 265                 270

Gly Ile Lys Val Arg Gln Leu Cys Lys Leu Leu Arg Gly Thr Lys Ala
        275                 280                 285

Leu Thr Glu Val Ile Pro Leu Thr Glu Glu Ala Glu Leu Glu Leu Ala
290                 295                 300

Glu Asn Arg Glu Ile Leu Lys Glu Pro Val His Gly Val Tyr Tyr Asp
305                 310                 315                 320

Pro Ser Lys Asp Leu Ile Ala Glu Ile Gln Lys Gln Gly Gln Gly Gln
                325                 330                 335

Trp Thr Tyr Gln Ile Tyr Gln Glu Pro Phe Lys Asn Leu Lys Thr Gly
                340                 345                 350

Lys Tyr Ala Arg Met Arg Gly Ala His Thr Asn Asp Val Lys Gln Leu
        355                 360                 365

Thr Glu Ala Val Gln Lys Ile Thr Thr Glu Ser Ile Val Ile Trp Gly
        370                 375                 380

Lys Thr Pro Lys Phe Lys Leu Pro Ile Gln Lys Glu Thr Trp Glu Thr
385                 390                 395                 400

Trp Trp Thr Glu Tyr Trp Gln Ala Thr Trp Ile Pro Glu Trp Glu Phe
                405                 410                 415

Val Asn Thr Pro Pro Leu Val Lys Leu Trp Tyr Gln Leu Glu Lys Glu
                420                 425                 430

Pro Ile Val Gly Ala Glu Thr Phe Tyr Val Asp Gly Ala Ala Asn Arg
        435                 440                 445

Glu Thr Lys Leu Gly Lys Ala Gly Tyr Val Thr Asn Lys Gly Arg Gln
450                 455                 460
```

```
Lys Val Val Pro Leu Thr Asp Thr Thr Asn Gln Lys Thr Gln Leu Gln
465                 470                 475                 480

Ala Ile Tyr Leu Ala Leu Gln Asp Ser Gly Leu Glu Val Asn Ile Val
                485                 490                 495

Thr Asp Ser Gln Tyr Ala Leu Gly Ile Ile Gln Ala Gln Pro Asp Glu
            500                 505                 510

Ser Glu Ser Glu Leu Val Asn Gln Ile Ile Glu Gln Leu Ile Lys Lys
        515                 520                 525

Glu Lys Val Tyr Leu Ala Trp Val Pro Ala His Lys Gly Ile Gly Gly
    530                 535                 540

Asn Glu Gln Val Asp Lys Leu Val Ser Ala
545                 550
```

```
<210> SEQ ID NO 12
<211> LENGTH: 10
<212> TYPE: RNA
<213> ORGANISM: ARTIFICIAL SEQUENCE
<220> FEATURE:
<223> OTHER INFORMATION: synthetic construct

<400> SEQUENCE: 12
gcuagggccc                                                                10
```

```
<210> SEQ ID NO 13
<211> LENGTH: 10
<212> TYPE: RNA
<213> ORGANISM: ARTIFICIAL SEQUENCE
<220> FEATURE:
<223> OTHER INFORMATION: synthetic construct
<220> FEATURE:
<221> NAME/KEY: misc_feature
<222> LOCATION: (4)..(4)
<223> OTHER INFORMATION: n is 2-aminopurine

<400> SEQUENCE: 13 gcungggccc                                                                10
```

```
<210> SEQ ID NO 14
<211> LENGTH: 10
<212> TYPE: RNA
<213> ORGANISM: ARTIFICIAL SEQUENCE
<220> FEATURE:
<223> OTHER INFORMATION: synthetic construct
<220> FEATURE:
<221> NAME/KEY: misc_feature
<222> LOCATION: (3)..(3)
<223> OTHER INFORMATION: n is 2-aminopurine

<400> SEQUENCE: 14 gcnugggccc                                                                10
```

```
<210> SEQ ID NO 15
<211> LENGTH: 10
<212> TYPE: RNA
<213> ORGANISM: ARTIFICIAL SEQUENCE
<220> FEATURE:
<223> OTHER INFORMATION: synthetic construct
<220> FEATURE:
<221> NAME/KEY: misc_feature
<222> LOCATION: (2)..(2)
<223> OTHER INFORMATION: n is 2-aminopurine

<400> SEQUENCE: 15 cnugggccc                                                                 10
```

```
<210> SEQ ID NO 16
<211> LENGTH: 28
<212> TYPE: PRT
<213> ORGANISM: Influenza A virus

<400> SEQUENCE: 16

Asn Arg Phe Tyr Arg Thr Cys Lys Leu Leu Gly Ile Asn Met Ser Lys
1               5                   10                  15

Lys Lys Ser Tyr Ile Asn Arg Thr Gly Thr Phe Glu
            20                  25

<210> SEQ ID NO 17
<211> LENGTH: 28
<212> TYPE: PRT
<213> ORGANISM: Influenza B virus

<400> SEQUENCE: 17

Asn Asp Phe Tyr Arg Thr Cys Lys Leu Leu Gly Ile Asn Met Ser Lys
1               5                   10                  15

Lys Lys Ser Tyr Cys Asn Glu Thr Gly Met Phe Glu
            20                  25

<210> SEQ ID NO 18
<211> LENGTH: 28
<212> TYPE: PRT
<213> ORGANISM: Influenza C virus

<400> SEQUENCE: 18

Arg Arg Phe Asn Ala Val Cys Lys Leu Ile Gly Ile Asn Met Ser Leu
1               5                   10                  15

Glu Lys Ser Tyr Gly Ser Leu Pro Glu Leu Phe Glu
            20                  25

<210> SEQ ID NO 19
<211> LENGTH: 29
<212> TYPE: PRT
<213> ORGANISM: Poliovirus

<400> SEQUENCE: 19

Ser Leu Leu Ala Gln Ser Gly Lys Asp Tyr Gly Leu Thr Met Thr Pro
1               5                   10                  15

Ala Asp Lys Ser Ala Thr Phe Glu Thr Val Thr Trp Glu
            20                  25

<210> SEQ ID NO 20
<211> LENGTH: 27
<212> TYPE: PRT
<213> ORGANISM: Poliovirus

<400> SEQUENCE: 20

Val Asp Ala Ser Leu Leu Ala Gln Ser Gly Lys Asp Tyr Gly Leu Thr
1               5                   10                  15

Met Thr Pro Ala Asp Lys Ser Ala Thr Phe Glu
            20                  25

<210> SEQ ID NO 21
<211> LENGTH: 27
<212> TYPE: PRT
<213> ORGANISM: coxsackievirus

<400> SEQUENCE: 21

Val Asp Ala Ser Leu Leu Ala Gln Ser Gly Lys Asp Tyr Gly Leu Thr
1               5                   10                  15
```

-continued

```
Met Thr Pro Ala Asp Lys Ser Ala Thr Phe Glu
            20                  25

<210> SEQ ID NO 22
<211> LENGTH: 27
<212> TYPE: PRT
<213> ORGANISM: human rhinovirus 14

<400> SEQUENCE: 22

Leu Asp Pro Gln Val Leu Ala Thr Leu Gly Lys Asn Tyr Gly Leu Thr
1               5                   10                  15

Ile Thr Pro Pro Asp Lys Ser Glu Thr Phe Thr
            20                  25

<210> SEQ ID NO 23
<211> LENGTH: 29
<212> TYPE: PRT
<213> ORGANISM: rabbit haemorrhagic disease virus

<400> SEQUENCE: 23

Met Val Ser Leu Leu Pro Ala Ile Ile Glu Asn Leu Arg Asp Tyr Gly
1               5                   10                  15

Leu Ser Pro Thr Ala Ala Asp Lys Thr Glu Phe Ile Asp
            20                  25

<210> SEQ ID NO 24
<211> LENGTH: 30
<212> TYPE: PRT
<213> ORGANISM: feline calicivirus

<400> SEQUENCE: 24

Phe Ala Ser Val Ser Asp Gln Ile Phe Ala Asn Leu Ser Ala Tyr Gly
1               5                   10                  15

Leu Lys Pro Thr Arg Val Asp Lys Ser Val Gly Ser Ile Glu
            20                  25                  30

<210> SEQ ID NO 25
<211> LENGTH: 35
<212> TYPE: PRT
<213> ORGANISM: severe acute respiratory syndrome coronavirus

<400> SEQUENCE: 25

Tyr Ala Ala Gln Gly Leu Val Ala Ser Ile Lys Asn Phe Lys Ala Val
1               5                   10                  15

Leu Tyr Tyr Gln Asn Asn Val Phe Met Ser Glu Ala Lys Cys Trp Ile
            20                  25                  30

Glu Thr Asp
        35

<210> SEQ ID NO 26
<211> LENGTH: 35
<212> TYPE: PRT
<213> ORGANISM: mouse hepatitis virus

<400> SEQUENCE: 26

Phe Ala Ser Lys Gly Tyr Ile Ala Asn Ile Ser Ala Phe Gln Gln Val
1               5                   10                  15

Leu Tyr Tyr Gln Asn Asn Val Phe Met Ser Glu Ala Lys Cys Trp Val
            20                  25                  30

Glu Thr Asp
        35
```

```
<210> SEQ ID NO 27
<211> LENGTH: 34
<212> TYPE: PRT
<213> ORGANISM: hepatitis C virus

<400> SEQUENCE: 27

Gly Thr Gln Glu Asp Glu Ala Ser Leu Arg Ala Phe Thr Glu Ala Met
1               5                   10                  15

Thr Arg Tyr Ser Ala Pro Pro Gly Asp Pro Pro Lys Pro Glu Tyr Asp
            20                  25                  30

Leu Glu

<210> SEQ ID NO 28
<211> LENGTH: 29
<212> TYPE: PRT
<213> ORGANISM: human immunodeficiency virus type-1

<400> SEQUENCE: 28

Ile Gly Gln His Arg Thr Lys Ile Glu Glu Leu Arg Gln His Leu Leu
1               5                   10                  15

Arg Trp Gly Leu Thr Thr Pro Asp Lys Lys His Gln Lys
            20                  25

<210> SEQ ID NO 29
<211> LENGTH: 22
<212> TYPE: PRT
<213> ORGANISM: bacteriophage Q-beta

<400> SEQUENCE: 29

Pro Ala Leu Arg Glu Val Phe Lys Tyr Val Gly Phe Thr Thr Asn Thr
1               5                   10                  15

Lys Lys Thr Phe Ser Glu
            20
```